(12) United States Patent
Chatelain et al.

(10) Patent No.: US 8,637,259 B1
(45) Date of Patent: Jan. 28, 2014

(54) METHODS OF IDENTIFYING MODULATORS OF OLFACTORY RECEPTORS INVOLVED IN THE PERCEPTION OF SWEAT CARBOXYLIC ACIDS

(75) Inventors: Pierre Chatelain, Brussels (BE); Alex Veithen, Genappe (BE)

(73) Assignee: ChemCom S.A., Brussels (BE)

( * ) Notice: Subject to any disclaimer, the term of this patent is extended or adjusted under 35 U.S.C. 154(b) by 0 days.

(21) Appl. No.: 13/024,325

(22) Filed: Feb. 9, 2011

(51) Int. Cl.
*G01N 33/53* (2006.01)
*G01N 33/567* (2006.01)

(52) U.S. Cl.
USPC ............ 435/7.1; 435/7.2; 435/7.21; 435/810; 435/975

(58) Field of Classification Search
None
See application file for complete search history.

(56) References Cited

U.S. PATENT DOCUMENTS

2008/0299586 A1   12/2008   Han et al.

FOREIGN PATENT DOCUMENTS

WO   2012/029922   3/2012

OTHER PUBLICATIONS

Laska M, et al. Chem. Senses 29:101-109, 2004.*
Krautwurst B, Chemistry & Biodiversity. 5:842-852, 2008.*
Idan Menashe, et al., Genetic Elucidation of Human Hyperosmia to Isovaleric Acid, PloS Biology, Nov. 2007, vol. 5, Issue 11, p. 2462.

* cited by examiner

*Primary Examiner* — Robert Landsman
(74) *Attorney, Agent, or Firm* — Edwards Wildman Palmer LLP; Ralph A. Loren; Daniel W. Clarke

(57) ABSTRACT

The invention relates to the identification of carboxylic acids, present in human sweat, as natural ligands of a specific subgroup of seven olfactory receptor (OR) belonging to class 1 within the OR classification. The invention encompasses the use of the interaction of OR polypeptides and carboxylic acids as the basis of screening assays for agents that specifically modulate the activity of the seven ORs of the invention.

33 Claims, 13 Drawing Sheets

Figure 1A

SEQ ID NO: 1 OR52L1 DNA

Atgactttggtttctttttctctttcctctccaagccattgataatgctccttagcaattcaagctggaggctatcccagccttctttctcctggtagggattc
caggtttagaggaaagccagcactggattgcactgcccctgggcatccttacctccttgctttagtgggcaatgttaccattctcttcatcatctggatgg
acccatccttgcaccaatctatgtacctcttcctgtccatgctagctgccatcgacctggttctggcctcctccactgcacccaaagcccttgcagtgctcct
ggttcatgcccacgagattgggtacatcgtctgcctgatccagatgttcttcatccatgcattctcctccatggagttaggggtacttgtggccatggctct
ggattgctatgtagccatttgtcaccccttgcaccattccacaatcctgcatccagggtcatagggcgcatcggaatggtggtgctggtgaggggatta
ctactccttatcccctttccccattttgttgggaacacttatcttctgccaagccaccatcataggccatgcctattgtgaacatatggctgttgtgaaacttgc
ctgctcagaaaccacagtcaatcgagcttatgggctgactatggccttgcttgtgattgggctggatgttctggccattggtgtttcctatgcccacatcct
ccaggcagtgctgaaggtaccagggagtgaggcccgacttaaggcgtttagcacatgtggctctcatatttgtgtcatcctggtcttctatgtccctgga
attttctccttcctcactcaccgctttggtcatcatgtaccccatcatgtccatgttcttctggccacacggtatctcctcatgccacctgcgctcaatcctcttg
tctatggagtgaagactcagcagatccgccagcgagtgctcagagtgtttacacaaaaggattaa SEQ ID NO: 2 OR52L1 Polypeptide MTLVSFFSFLSKPLIMLLSNSSWRLSQPSFLLVGIPGLEESQHWIALPLGILYLLALVGNVTILFIIWMDPSLHQSMYLFLS
MLAAIDLVLASSTAPKALAVLLVHAHEIGYIVCLIQMFFIHAFSSMELGVLVAMALDCYVAICHPLHHSTILHPGVIGRIGM
VVLVRGLLLLIPFPILLGTLIFCQATIIGHAYCEHMAVVKLACSETTVNRAYGLTMALLVIGLDVLAIGVSYAHILQAVLKVP
GSEARLKAFSTCGSHICVILVFYVPGIFSFLTHRFGHHVPHHVHVLLATRYLLMPPALNPLVYGVKTQQIRQRVLRVFTQK
D

SEQ ID NO: 3 OR52E8 DNA

Atggcaggaagaatgtctacgtctaatcacacccagttccatccttcttcattcctactgctgggtatcccagggctagaagatgtgcacatttggattgg
tgtccctttttttctttgtgtatcttgttgcactcctgggaaacactgctctcttgtttgtgatccagactgagcagagtctccatgagcctatgtactacttcctg
gccatgttggattccattgacctgggcttgtctacagccaccatccccaaaatgttgggcatcttctggttcaataccaaagaaatatcttttggaggctgc
ctttctcacatgttcttcatccatttcttcactgctatggagagcattgtgttggtggccatggccttgaccgctacattgccatttgcaaacctcttcggtac
accatgatcctcaccagcaaaatcatcagcctcattgcaggcattgctgtcctgaggagcctgtacatggttgttccactggtgtttctccttctgaggctg
ccttctgtgggcatcgtatcatccctcatacttattgtgagcacatgggcattgccgtctggcctgtgccagcatcaaagtcaacattaggtttggcctt
ggcaacatatctctcttgttactggatgttatccttattattctcctcctatgtcaggatcctgtatgctgtcttctgcctgccctcctgggaagctcgactcaaa
gctctcaacacctgtggtctcatattggtgttatcttagccttttttacaccagcatttttttcattcttgacacatcgtttggccataatatcccacagtatat
acatattatattagccaacctgtatgtggttgtcccaccagccctcaatcctgtaatctatggagtcaggacaaagcagattcgagagagagtgctgag
gattttctcaagaccaatcactaa SEQ ID NO: 4 OR52E8 Polypeptide MAGRMSTSNHTQFHPSSFLLLGIPGLEDVHIWIGVPFFFVYLVALLGNTALLFVIQTEQSLHEPMYYFLAMLDSIDLGLST
ATIPKMLGIFWFNTKEISFGGCLSHMFFIHFFTAMESIVLVAMAFDRYIAICKPLRYTMILTSKIISLIAGIAVLRSLYMVVPL
VFLLLRLPFCGHRIIPHTYCEHMGIARLACASIKVNIRFGLGNISLLLLDVILIILSYVRILYAVFCLPSWEARLKALNTCGSH
IGVILAFFTPAFFSFLTHRFGHNIPQYIHIILANLYVVVPPALNPVIYGVRTKQIRERVLRIFLKTNH

SEQ ID NO: 5 OR52B2 DNA

Atgagtcacaccaatgttaccatcttccatcctgcagttttgtccttcctggcatccctgggttggaggcttatacatttggctgtcaatacctctttgcctc
atttacatcactgcagtcctgggaaacagcatcctgatagtggttattgtcatggaacgtaacctcatgtgcccatgtattcttcctctcaatgctggccg
tcatggacatcctgctgtctaccaccactgtgcccaaggccctagccatctttggcttcaagcacataacattgctttgatgcctgtgtcacccaaggctt
ctttgtccatatgatgtttgtggggagtcagctatcctgttagccatggcctttgatcgctttgtggccatttgtgccccactgagatatacaacagtgcta
acatggcctgttgtggggaggattgctctggccgtcatcacccgaagcttctgcatcatcttcccagtcatattcttgctgaagcggctgccctctgccta
accaacattgttcctcactcctactgtgagcatattggagtggctcgtttagcctgtgctgacatcactgttaacatttggtatggcttctcagtgccattgt
catggtcatcttggatgttatcctcatcgctgtgtcttactcactgatcctccgagcagtgtttcgtttgccctcccaggatgctcggcacaaggccctcagc
acttgtggctcccacctctgtgtcatccttatgtttatgttccatccttcttaccttattgacccatcattttgggcgtaatattcctcaacatgtccatatcttg
ctggccaatctttatgtggcagtgccaccaatgctgaaccccattgtctatggtgtgaagactaagcagatacgtgagggtgtagcccaccggttctttg
acatcaagacttggtgctgtacctcccctctgggctcataa

Figure 1B

SEQ ID NO: 6 OR52B2 Polypeptide

MSHTNVTIFHPAVFVLPGIPGLEAYHIWLSIPLCLIYITAVLGNSILIVVIVMERNLHVPMYFFLSMLAVMDILLSTTTVPKAL
AIFWLQAHNIAFDACVTQGFFVHMMFVGESAILLAMAFDRFVAICAPLRYTTVLTWPVVGRIALAVITRSFCIIFPVIFLLK
RLPFCLTNIVPHSYCEHIGVARLACADITVNIWYGFSVPIVMVILDVILIAVSYSLILRAVFRLPSQDARHKALSTCGSHLC
VILMFYVPSFFTLLTHHHFGRNIPQHVHILLANLYVAVPPMLNPIVYGVKTKQIREGVAHRFFDIKTWCCTSPLGS

SEQ ID NO:7 OR51I2 DNA

Atggggttgttcaatgtcactcaccctgcattcttcctcctgactggtatccctggtctggagagctctcactcctggctgtcagggcccctctgcgtgatgt
atgctgtggcccttgggggaaatacagtgatcctgcaggctgtgcgagtggagcccagcctccatgagcccatgtactacttcctgtccatgttgtccttc
agtgatgtggccatatccatggccacactgcccactgtactccgaaccttctgcctcaatgcccgcaacatcacttttgatgcctgtctaattcagatgtttc
ttattcacttcttctccatgatggaatcaggtattctgctggccatgagttttgaccgctatgtggccatttgtgaccccttgcgctatgcagctgtgctcacc
actgaagtcattgctgcaatgggtttaggtgcagctgctcgaagcttcatcaccctttccctcttccctttcttattaagaggctgcctatctgcagatcca
atgttctttctcactcctactgcctgcacccagacatgatgaggcttgcctgtgctgatatcagtatcaacagcatctatggactctttgttcttgtatccacc
tttggcatggacctgtttttatcttcctctcctatgtgctcattctgcgttctgtcatggccactgcttcccgtgaggaacgcctcaaagctctcaacacatgt
gtgtcacatatcctggctgtacttgcattttatgtgccaatgattgggtgtccacagtgcaccgctttgggaagcatgtcccatgctacatacatgtcctc
atgtcaaatgtgtacctatttgtgcctcctgtgctcaaccctctcatttatagcgccaagacaaaggaaatccgccgagccattttccgcatgtttcaccac
atcaaaatatga SEQ ID NO: 8 OR51I2 Polypeptide MGLFNVTHPAFFLLTGIPGLESSHSWLSGPLCVMYAVALGGNTVILQAVRVEPSLHEPMYYFLSMLSFSDVAISMATLPT
VLRTFCLNARNITFDACLIQMFLIHFFSMMESGILLAMSFDRYVAICDPLRYAAVLTTEVIAAMGLGAAARSFITLFPLPFLI
KRLPICRSNVLSHSYCLHPDMMRLACADISINSIYGLFVLVSTFGMDLFFIFLSYVLILRSVMATASREERLKALNTCVSHI
LAVLAFYVPMIGVSTVHRFGKHVPCYIHVLMSNVYLFVPPVLNPLIYSAKTKEIRRAIFRMFHHIKI

SEQ ID NO: 9 OR52E1 DNA

Atgaataccactctatttcatccttactcttccttcttctgggaattcctgggctggaaagtatgcatctctgggttggttttccttttcttttgctgtgttcctgac
agctgtccttgggaatatcaccatcttttttgtgattcagactgacagtagtctccatcatcccatgttctacttcctggccattctgtcatctattgacccgg
gcctgtctacatccaccatccctaaaatgcttggcaccttctggtttaccctgagagaaatctcctttgaaggatgccttacccagatgttcttcatccacct
gtgcactggcatggaatcagctgtgcttgtggccatggcctatgattgctatgtggccatctgtgaccctctttgctacacgttggtgctgacaaacaagg
tggtgtcagttatggcactggccatctttctgagacccctagtctttgtcataccctttgtctatttatcctaaggcttccattttgtggacaccaaattattcc
tcatacttacggtgagcacatgggcattgcccgcctgtcttgtgccagcatcagggttaacatcatctatggcttatgtgccatctctatcctggtctttgac
atcatagcaattgtcatttcctatgtacagatcctttgtgctgtattcactctcttcacatgatgcacgactcaaggcattcagcacctgtggctctcatgt
gtgtgtcatgttgactttctatatgcctgcattgttctcattcatgacccataggtttggtcggaatatacctcactttatccacattcttctggctaatttctgt
gtagtcattccacctgctctcaactctgtaatttatggtgtcagaaccaaacagattagagcacaagtgctgaaaatgttttcaataaataa SEQ ID NO: 10 OR52E1 Polypeptide MNTTLFHPYSFLLLGIPGLESMHLWVGFPFFAVFLTAVLGNITILFVIQTDSSLHHPMFYFLAILSSIDPGLSTSTIPKMLGT
FWFTLREISFEGCLTQMFFIHLCTGMESAVLVAMAYDCYVAICDPLCYTLVLTNKVVSVMALAIFLRPLVFVIPFVLFILRLP
FCGHQIIPHTYGEHMGIARLSCASIRVNIIYGLCAISILVFDIIAIVISYVQILCAVFLLSSHDARLKAFSTCGSHVCVMLTF
YMPALFSFMTHRFGRNIPHFIHILLANFCVVIPPALNSVIYGVRTKQIRAQVLKMFFNK

SEQ ID NO: 11 OR52A5 DNA

Atgccgacattcaatggctcagtcttcatgccctctgcgtttatactaattgggattcctggtctggagtcagtgcagtgttggattgggattcctttctctg
ccatgtatcttattggtgtgattggaaattccctaattttagttataatcaaatatgaaaacagcctccatataccatgtacattttttggccatgttggca
gccacagacattgcacttaacacctgcattcttcccaaatgttaggcatcttctggtttcatttgccagagatttcttttgatgcctgtctttttcaaatgtgg
cttattcactcattccaggcaattgaatcgggtatccttctggcaatggccctggatcgctatgtggccatctgtatccccttgagacatgccaccatcttt
cccagcagttcttaactcatattggacttggggtgacactcagggctgccattcttataatacctccttagggctcatcaaatgctgtctgaaacactatc
gaactacagtcatctctcactcttactgtgagcacatggccatcgtgaagctggctactgaagatatccgagtcaacaagatatatggcctatttgttgcc
tttgcaatcctaggggtttgacataatatttataaccttgtcctatgtccaaattttttatcactgtctttcagctgccccagaaggaggcacgattcaaggcctt
taatacatgcattgcccacatttgtgtcttcctacagttctaccttcttgccttcttctctttcttcacacacaggtttggttcacacataccaccatatattcata
tcctccttgtcaaatcttacctgttagtcccaccttttctcaaccctattgtctatggagtgaagaccaagcaaattcgtgaccatattgtgaaagtgtttttct
tcaaaaagtaa

Figure 1C

SEQ ID NO: 12 OR52A5 Polypeptide

MPTFNGSVFMPSAFILIGIPGLESVQCWIGIPFSAMYLIGVIGNSLILVIIKYENSLHIPMYIFLAMLAATDIALNTCILPKML
GIFWFHLPEISFDACLFQMWLIHSFQAIESGILLAMALDRYVAICIPLRHATIFSQQFLTHIGLGVTLRAAILIIPSLGLIKCC
LKHYRTTVISHSYCEHMAIVKLATEDIRVNKIYGLFVAFAILGFDIIFITLSYVQIFITVFQLPQKEARFKAFNTCIAHICVFL
QFYLLAFFSFFTHRFGSHIPPYIHILLSNLYLLVPPFLNPIVYGVKTKQIRDHIVKVFFFKK

SEQ ID NO: 13 OR56A5 DNA

Atgacattacccagcaacaactccacttcccagtctttgaattcttcctcatttgtttccccagtttccagagctggcagcactggctgtctctgcccctca
gcctcctcttcctcctggccatgggggccaatgccacccttctgatcaccatctatctggaagcctctctgcaccagcccctgtactacctgctcagcctcct
ctccctgctggacatcgtactctgcctcaccgtcatccccaaggtcctggccatcttctggtttgacctcagatcaatcagcttccctgcctgcttccttcaga
tgttcatcatgaacagttttctgactatggagtcctgcacattcatgatcatggcctatgaccgctatgtggccatctgcaagcccctacagtactcatcca
tcatcactgatcaatttgttgctagggctgccatctttgttgtggccaggaatggccttcttactatgcctatccccatactttcttctcgactcagatactgtg
caggacacatcatcaagaactgcatctgtactaacgtgtctgtgtctaaactctcttgtgatgacatcaccttgaatcagagctaccagtttgttataggtt
ggaccctgctgggctctgacctcatccttattgttctctcttacttttttatcttgaaaactgtgctaaggattaagggtgagggagatatggccaaagctct
aggtacttgtggttcccacttcatcctcatcctcttcttcaccacagtcctgctggttctggtcatcactaacctggccaggaagagaattcctccggatgtc
cccatcctgctcaacatcctgcaccaccttattcccccagctctgaaccccattgtttatggtgtgagaaccaaggagatcaagcagggaatccagaacc
tgctgaagaggttgtaa SEQ ID NO: 14 OR56A5 Polypeptide MTLPSNNSTSPVFEFFLICFPSFQSWQHWLSLPLSLLFLLAMGANATLLITIYLEASLHQPLYYLLSLLSLLDIVLCLTVIPKV
LAIFWFDLRSISFPACFLQMFIMNSFLTMESCTFMIMAYDRYVAICKPLQYSSIITDQFVARAAIFVVARNGLLTMPIPILSS
RLRYCAGHIIKNCICTNVSVSKLSCDDITLNQSYQFVIGWTLLGSDLILIVLSYFFILKTVLRIKGEGDMAKALGTCGSHFI
LILFFTTVLLVLVITNLARKRIPPDVPILLNILHHLIPPALNPIVYGVRTKEIKQGIQNLLKRL

SEQ ID NO: 15

Ac-FKKSFKL-NH2

SEQ ID NO: 16

RRLIEDAEYAARG

Figure 2A: concentration dependent activation of OR52L1, measured with luciferase assay
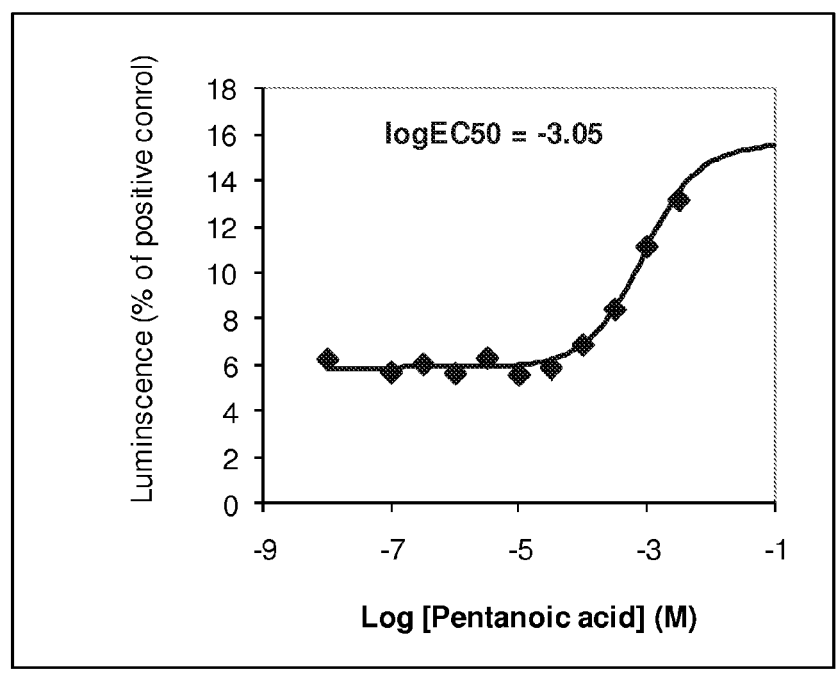

Figure 2B: concentration dependent activation of OR52E8, measured with luciferase assay
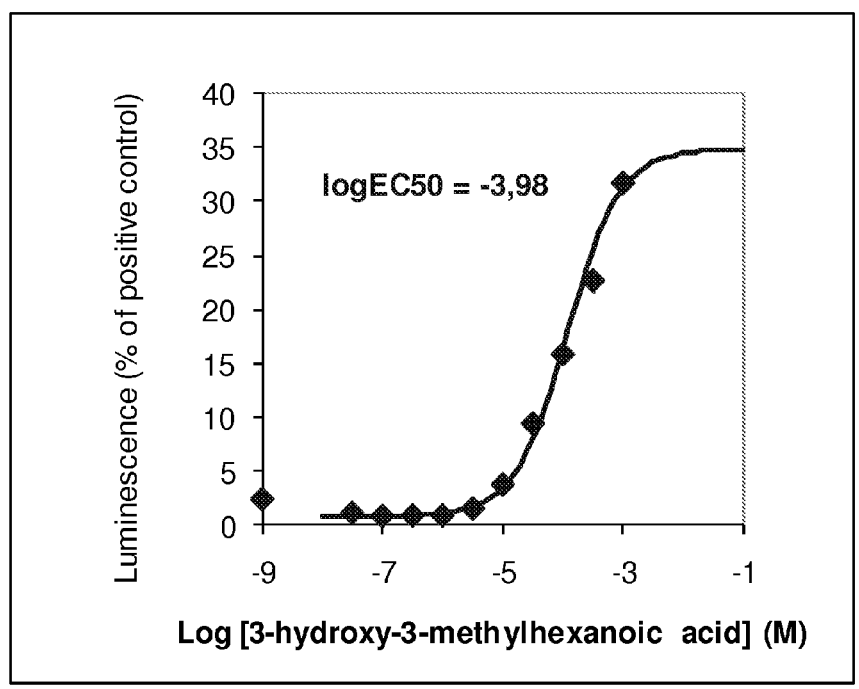

Figure 2C: concentration dependent activation of OR52E1, measured with luciferase assay
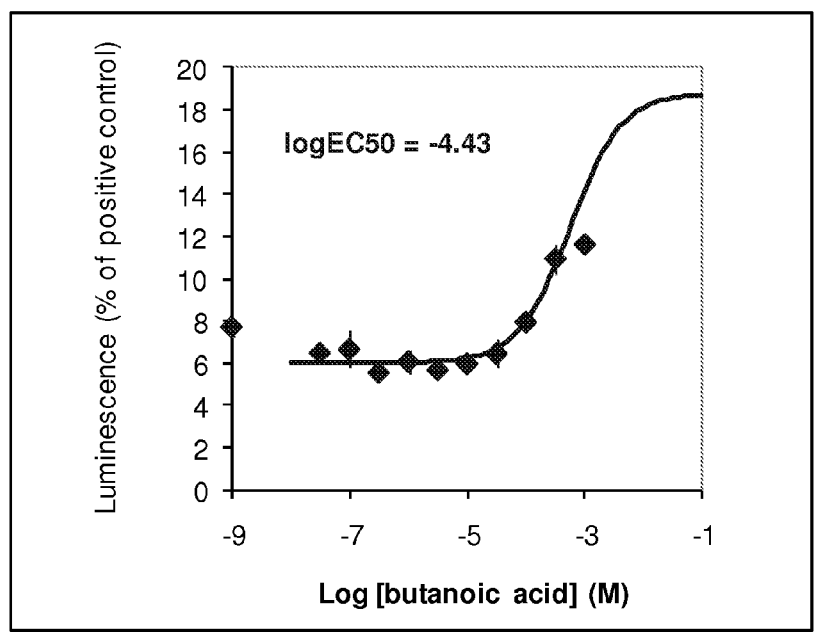

Figure 2D: concentration dependent activation of OR52A5, measured with luciferase assay
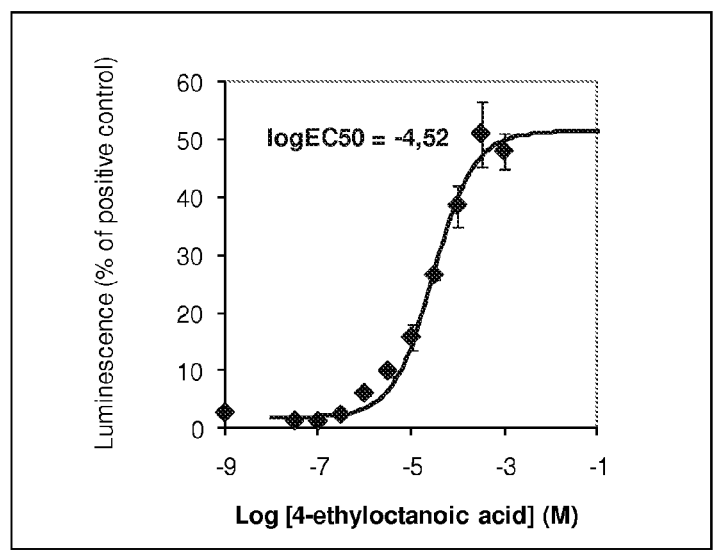

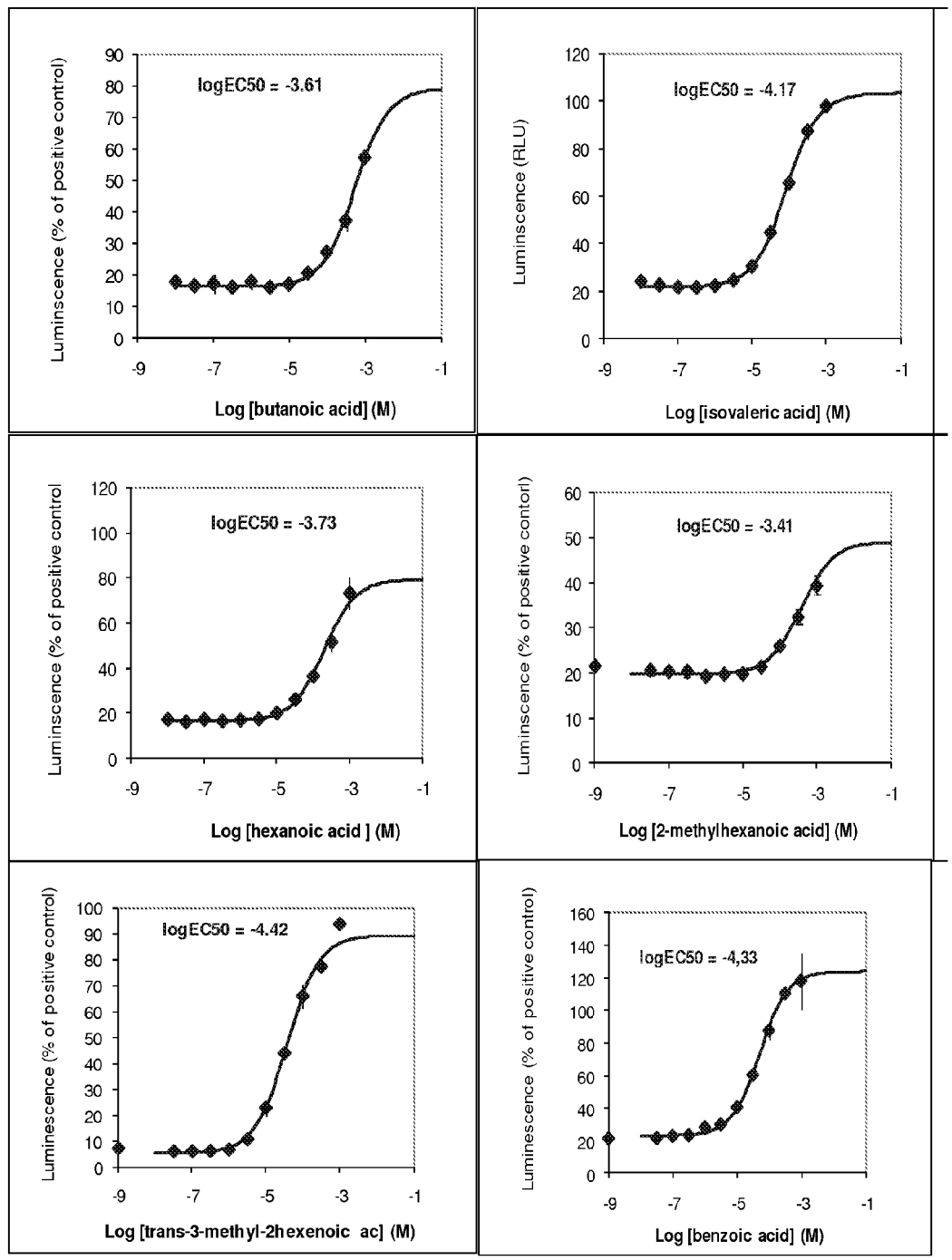
Figure 2E: concentration dependent activation of OR5I2, measured with luciferase assay

Figure 2F: concentration dependent activation of OR5I2, measured with luciferase assay
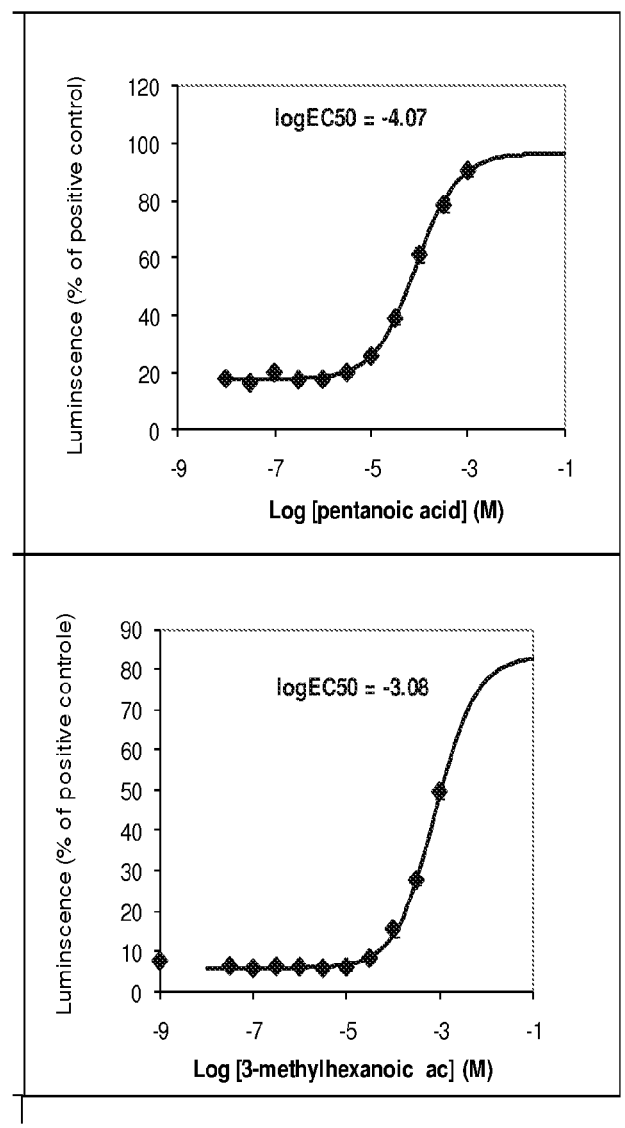

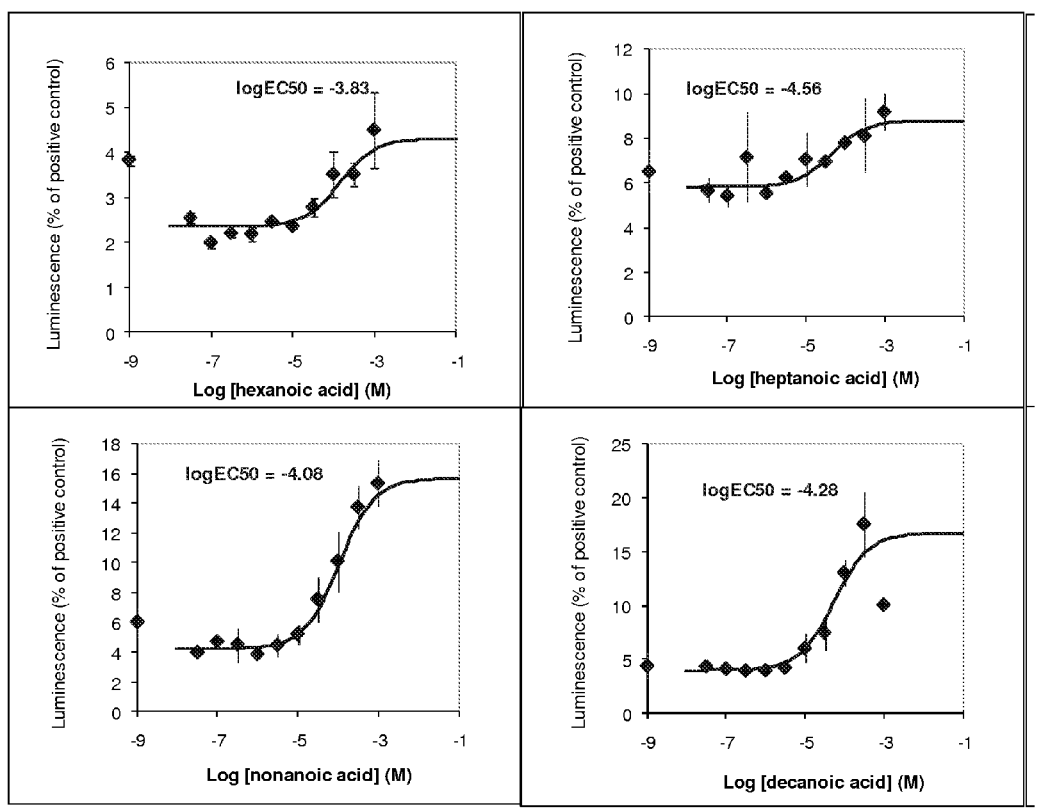
Figure 2G: concentration dependent activation of OR52B2, measured with luciferase assay

Figure 2H: concentration dependent activation of OR52B2, measured with luciferase assay
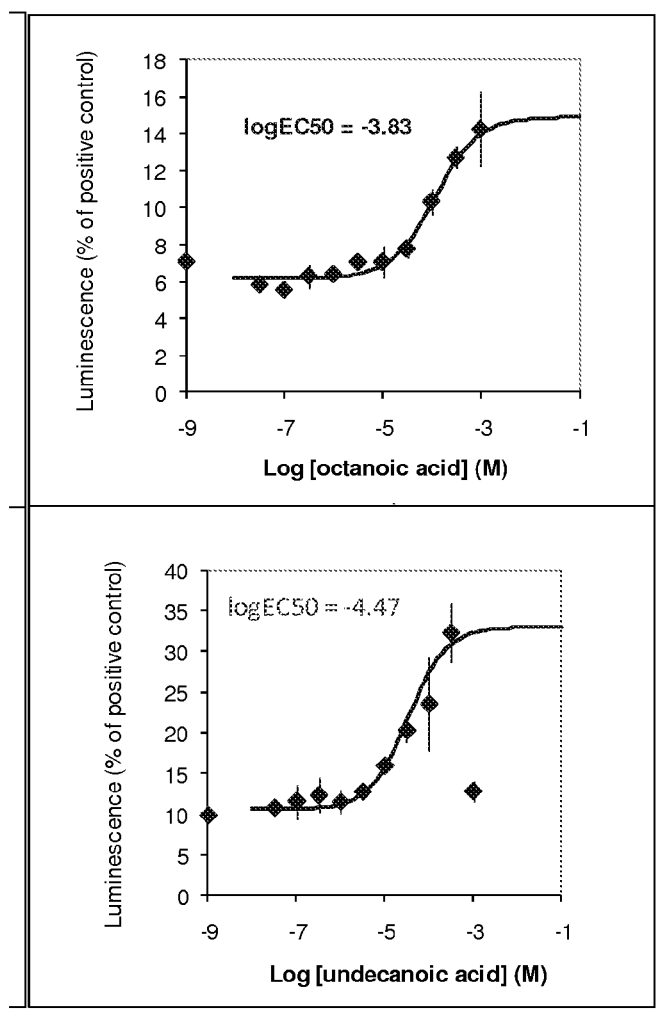

Figure 21: concentration dependent activation of OR56A5, measured with luciferase assay
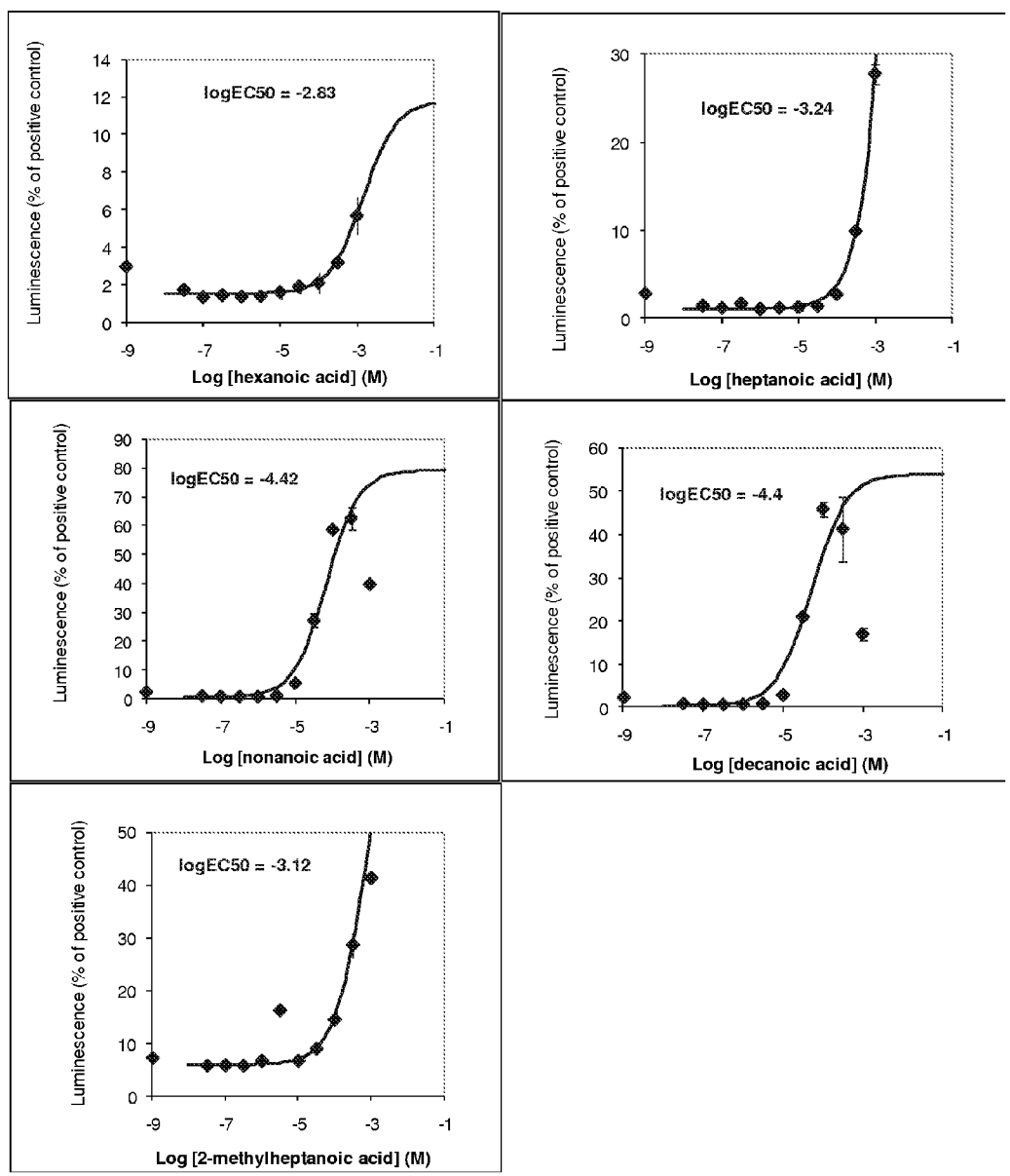

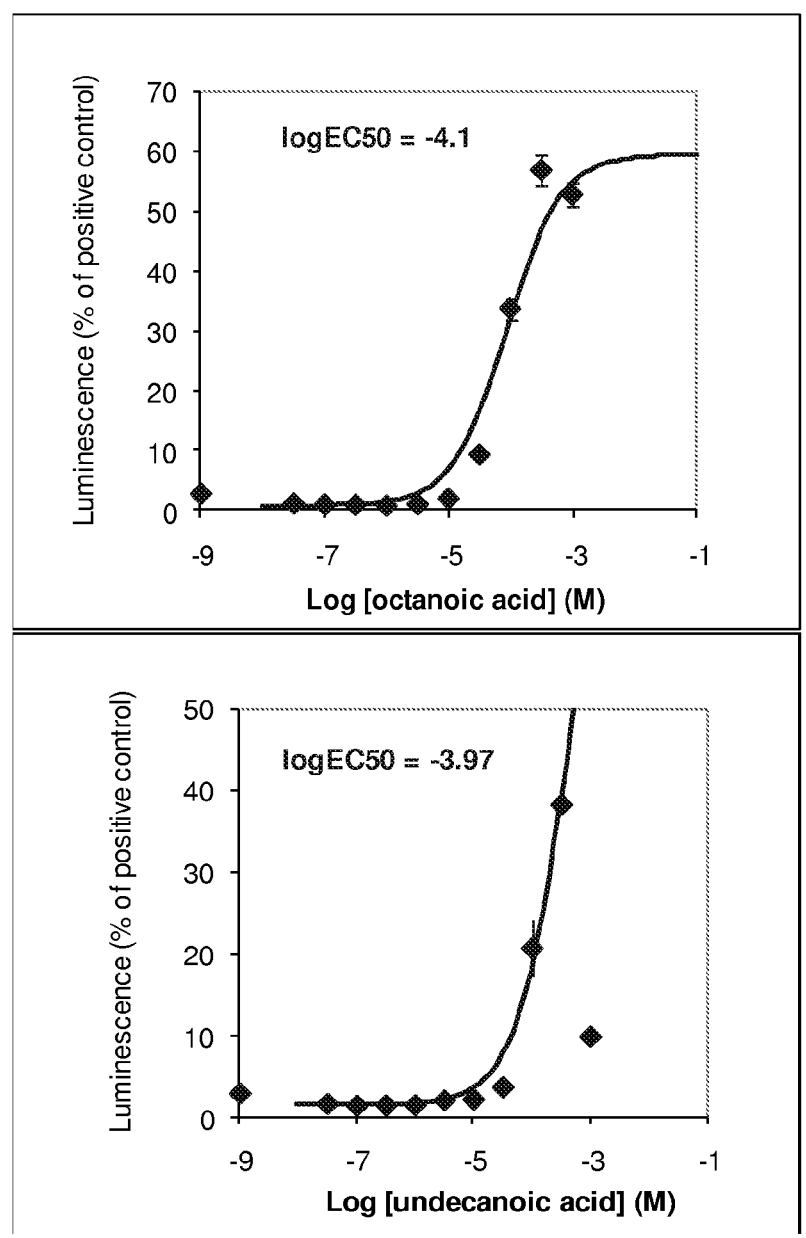
Figure 2J: concentration dependent activation of OR56A5, measured with luciferase assay

METHODS OF IDENTIFYING MODULATORS OF OLFACTORY RECEPTORS INVOLVED IN THE PERCEPTION OF SWEAT CARBOXYLIC ACIDS

FIELD OF THE INVENTION

The present invention relates to the characterization of olfactory receptors. In particular, the present invention relates to seven class 1 olfactory receptors and the identification of their natural ligands corresponding to carboxylic acids present in human sweat. The present invention provides assays and methods of screening for compounds, particularly antagonists or blockers, modulating the interaction between olfactory receptors and their respective natural ligands. The present invention further provides compositions and methods comprising the above-mentioned compounds to counteract sweat malodors.

BACKGROUND OF THE INVENTION

Olfactory Receptors

The genes coding for olfactory receptors (ORs) represent the largest family of genes (3% of the whole genome) in the human body dedicated to a single physiological function. These ORs belong to the superfamily of G protein coupled receptors (GPCRs). GPCRs are membrane receptors usually located at the surface of many different cell types. The common features of these receptors consist of seven transmembrane spans that form a barrel within the cell membrane and in their capacity to interact with heterotrimeric GTPase and thereby transducing a signal upon binding of their activators.

In the human genome, about 900 sequences containing characteristic signatures of olfactory receptors have been found. However, 60% of these appear to encode non-functional pseudogenes, thereby leaving humans with about 380 different OR proteins. ORs are characterized by 6 conserved amino acid motifs in their sequence. The first is the FILLG motif (SEQ ID No. 17) located in the extracellular N-terminal end of the receptor. It corresponds to a highly conserved phenylalanine and glycine separated by 3 variable but mostly hydrophobic amino acids. The other motifs include LHTPMY (SEQ ID No. 18) in intracellular loop 1, MAYDRYVAIC (SEQ ID No. 19) at the end of transmembrane domain 3 and the beginning of intracellular loop 2, SY (SEQ ID No. 20) at the end of transmembrane domain 5, FSTCSSH (SEQ ID No. 21) in the beginning of transmembrane domain 6, and PMLNPF (SEQ ID No. 22) in transmembrane domain 7.

The mammalian ORs are usually subdivided in two distinct classes. Class 1 ORs, also called fish-like receptors, form a homogenous group that is more closely related to ORs found in fish and are therefore assumed to represent a conserved relic maintained throughout the evolution of the vertebrates. The persistence of this group of ancestral ORs suggests that they play an important role in mammalian chemical perception. In humans, class 1 ORs encompass 68 non-pseudogenic sequences that correspond to potential functional proteins. These receptors share several characteristic domains in their sequence that allows their classification as "class 1" ORs. It is also to be noted that some amino acids located in the transmembrane domains are highly conserved within the members of the fish-like ORs. In contrast to the fish-like ORs, class 2 ORs first appeared in tetrapode vertebrates and expanded to form the majority of the OR repertoire presently known in humans. Class 2 ORs probably represent an adaptation to the terrestrial life where the detection of airborne odorants is required.

Mechanisms of Odor Perception

Each OR is able to interact with different molecules, and each odorant molecule can activate more than one OR. Thus, odor perception does not rely on the simple activation of a single OR, but rather on multiple activations of several ORs. An odor (which can be a single molecule or a mixture) is paired with a unique set of activated ORs that are sufficient for its discrimination and characterization. Odorant concentration can dramatically affect the profile of an odor as some additional ORs may be recruited (high concentration) or not activated (low concentration). Therefore, the set of activated ORs will differ for different odor concentrations, leading to varying odor perceptions. With a pool of 380 ORs, the number of possible combinations is almost infinite, thus explaining the outstanding discrimination properties of the olfactory system. Odorant receptors are expressed in specialized olfactory sensory neurons (OSNs) located at the top of the nasal cavity in a small area that constitutes the olfactory epithelium. Filiform extensions at one end of these cells contain the ORs on their surface and float in the nasal mucus where the odorants are dissolved. At the opposite end, the OSN extends its axon across the ethmoid bone at the base of the cranium to connect to the olfactory bulb a small region of the brain dedicated to the integration of the olfactory stimuli. An outstanding feature of the tens of millions of OSNs scattered throughout the olfactory epithelium is that each one expresses only one of the about 400 OR genes available in the human genome. The OSNs expressing the matching gene connect their axons to the same subregion of the olfactory bulb forming a structure called a glomerulus. It is from this organization of OSNs that the coding of an odor by a specific set of activated ORs is translated geographically in the bulb by a corresponding pattern of activated glomeruli. This information is further transmitted to the olfactory area of the cortex where it is decoded and analyzed. In OSNs, triggering of the OR promotes the activation of an olfactory-specific G protein (Galpha-olf) that stimulates a type III adenylate cyclase to produce cyclic AMP; this plays the role of a second messenger. Upon binding to a cAMP-gated cation channel, this messenger induces the entry of calcium into the cell. Calcium causes the opening of another channel that promotes the exit of chloride ions, and hence triggers an action potential of the neuron leading to a signal to the respective brain area.

Characterisation of Odorant Molecules with ORs

Cultured cell lines have been widely used to characterize and study receptors of interest in both academic and industrial contexts. This approach involves introduction of the corresponding gene into the cells, and subsequent promotion of its stable or transient overexpression. The activity of the receptor can be monitored using a functional assay. The use of easy-to-culture cell lines along with easy-to-perform functional assays facilitates several thousand measurements per day. Typically, in the pharmaceutical industry, it is common to test libraries of 1,000,000 compounds per day on non-olfactory receptors. In the aftermath of OR discovery, several attempts were made to express ORs in the cell lines suitable for the expression of non-olfactory receptors, but they remained largely unsuccessful. The reason for such a setback can be found, not in the failure of the cell to produce the receptor, but rather in its inability to send the receptor to the surface of the cell. A technique aimed at improving the functional expression of ORs requires engineering a conventional cell line to make it suitable for OR expression. In fact, it had long been suspected that correct expression and targeting of the OR at the cell surface requires an OSN-specific intracellular machinery that is absent in a non-olfactory cell line. Thorough analysis of the expression in OSNs revealed two members of a new family of proteins that are specific to this sensory cell. When co-introduced into a conventional cell line along with a model OR, the so-called receptor transport proteins 1 and 2 (RTP1 and RTP2) enhanced both the cell surface expression and the response of the receptor to its cognate odorants. The production of cAMP arising in the cell upon activation of the OR by its odorant molecules may be detected by an indirect approach that consists of the use of a reporter gene, as described in (Saito et al., 2004 *Cell* Vol. 119, 679-691). This gene is placed under the control of a cAMP inducible promoter and is expressed only upon induction by cAMP. Different genes can be used for this purpose, but one of the most popular ones encodes the light-producing protein luciferase. While cleaving its substrate, luciferin, this enzyme releases light that is readily detected and quantified. The intensity of light emitted reflects the amount of luciferase produced, which is proportional to the cAMP increase and therefore directly related to the activity of the receptor. One of the advantages of reporter gene assays is dependent upon the signal amplification between receptor activation and reporter production. This makes the assay particularly sensitive to weak responses that can hardly be detected by other functional assays.

Other functional assays have also been used to demonstrate the activation of an OR by its odorant ligand. One of these assays consists in monitoring the increase in cytosolic calcium that occurs upon activation of the receptor intracellular calcium increase (Krautwurtz D. et al. 1998. *Cell* 95, 917-26).

So far, the identification of odorant activators has only been reported for few mouse odorant ORs. Example of mouse OR deorphanization are given in Malnic et al., 1999, *Cell* 96, 713-23; Saito H. et al. 2009. *Sci. Signal.* 2, 1-14).

The identification of human OR activators has also been reported. Examples of deorphanized human ORs are e.g. given in Fujita Y et al. 2007. *J. Recept. Signal. Transduct. Res.* 27, 323-34; Keller A. et al. 2007. *Nature* 449, 468-72; Matarazzo V. et al. 2005. *Chem. Senses* 30, 195-207; Saito H. et al. 2009. *Sci. Signal.* 2, 1-14; Sanz G. et al. 2005. *Chem. Senses* 30, 69-80; Schmiedeberg K. et al. 2007. *J Struct. Biol.* 159, 400-12.; Shirokova E. et al. 2004. *J. Biol. Chem.* 280, 11807-15.; Spehr M. et al. 2003. *Science* 299, 2054-58.; Wetzel, K. et al. 1999. *J. Neurosci.* 19, 7426-33; Sallmann et al. PCT No. WO2006/094704.

For several of the receptors, more than one ligand has been identified. Odorants activating the same OR can belong to different odorant families such as alcohol, aldehyde, esters, etc (Sanz G. et al. 2005. *Chem. Senses* 30, 69-80; Saito H. et al. 2009. *Sci. Signal.* 2, 1-14).

Body Malodors

In our modern society, odors released by the human body, and more precisely in the sweat, are often considered as unpleasant or even offensive. Significant efforts have been made by the cosmetic industry to counteract the perception of these odors. Amongst the various categories of molecule present in human sweat, short chain carboxylic acids are of particular importance. Indeed, more than 50 different acids have been identified in sweat. A series of acids is assumed to participate in or to be important for the genesis of malodour (Table 1). For example, 3-hydroxy-3-methylhexanoic acid or (E)-3-methyl-2-hexenoic possess a pungent odor and both are known to be important contributors to axillary malodor (Zeng et al. 1991; *J. Chem. Ecolog.* Vol. 17 pp 1469-1492; Gautschi et al., 2007, *Chimia*, Vol. 61 pp 27-32). Isovaleric acid, another short chain carboxylic acid, has been identified as the major molecule responsible for the characteristic cheesy odor released by sweating feet (Ara et al. 2006. *Can. J. Microbiol. Vol.* 52 pp 357-364). Acids are not directly produced by the apocrine glands. They appear under the form of glutamine conjugates and are released under the action of skin bacteria enzymes. The abundance of several malodorants may therefore vary from one individual to another, depending on the composition of his bacterial flora.

TABLE 1

Carboxylic acids contributing to sweat malodor

| Molecule | References | Odor descriptor |
| --- | --- | --- |
| acetic acid | 1, 2, 3 | sharp pungent sour vinegar |
| propanoic acid | 2, 3 | pungent acidic cheesy vinegar |
| butanoic acid | 1, 2, 3 | sharp acetic cheese butter fruit |
| Isovaleric acid | 2, 3 | sour stinky feet sweaty cheese tropical |
| pentanoic acid | 3 | sickening putrid acidic sweaty rancid |
| hexanoic acid | 2, 3, 4, 5 | sour fatty sweat cheese |
| 2-methylhexanoic acid | 4 | acid, animalic, honey, civet, sweet |
| 3-methylhexanoic acid | 4 | sweaty, butyric |
| (E)-3-methyl-2-hexenoic acid | 4, 6 | acid, sweaty, fruity, fatty, labdanum, hay, soupy |
| 3-hydroxy-3-methylhexanoic acid | 6 | pungent sweaty |
| Heptanoic acid | 4, 5 | rancid sour cheesy sweat |
| 2-methylheptanoic acid | 4 | sour-fruity, sweet, slightly fatty-oily |
| Octanoic acid | 2, 3, 4, 5 | fatty waxy rancid oily vegetable cheesy |
| 4-ethyloctanoic acid | 4, 6 | costus, fatty, greasy |
| nonanoic acid | 4 | waxy dirty cheese cultured dairy |
| decanoic acid | 3, 4 | acid, hot iron, metallic, waxy, soapy, metal, candle |
| Undecanoic acid | 5 | waxy creamy cheese fatty coconut |
| benzoic acid | 2 | sweet; benzoin; powdery |
| phenylacetic acid | 6 | sweet, animal-honey |

1. Yamazaki et al. (2010) Anti-Aging Medicine. 7(6): 60-652.
2. Gallagher et al. (2008) Br. J. Dermatol. 159(4): 780-7913.
3. Ara et al. (2006) Can. J. Microbiol. 52: 357-3644.
4. Zeng et al. (1991) J. Chem. Ecol. 17(7): 1469-14925.
5. Labows et al. (1999) Antiperspirants and Deodorants, 2nd Edition ed K. Laden, Cosmetic Science and Technology Series Vol. 20 Marcel Dekker Inc, New York, 59-826.
6. Natsch et al (2006) Chem. & Biodiv. 3: 1-20

Different strategies have been developed to counteract sweat malodors. The most conventional ones consist in overpowering the malodor with a pleasant fragrance. In a more sophisticated approach, the fragrance is designed to harmonize well with the malodor and to shift the perception to a more pleasant character. In this case, the fragrance does not need to be a strong odorant by itself.

An alternative way for reducing malodor consists of limiting the production of odorant molecules. This can be achieved either by limiting the skin bacteria population with bacteriostatic agents or by blocking the enzymes responsible for the malodorant release. The development of antagonists and/or blockers that would specifically block the receptors for a malodor molecule can also be considered. An ideal blocker would have no odor per se, would not affect the bouquet and therefore would give a full creative freedom to perfumers.

In the present invention it has surprisingly been discovered that seven olfactory receptors belonging to class 1 of ORs are activated by carboxylic acids present in human sweat. This unexpected discovery allows the identification of compounds, which is of interest for the perfumer and flavorist companies. Indeed, the identified natural ligands of these seven olfactory receptors are known to be important constituents of sweat malodor. The identification and the use of blockers or antagonists of these olfactory receptors in a fragrance composition in order to modify the perception of sweat malodor represents an original concept that can open a new possibility for deodorant development.

SUMMARY OF THE INVENTION

The present invention relates to the identification of seven Olfactory Receptors (ORs) belonging to class 1 of ORs, namely, OR52L1, OR52E8, OR52B2, OR51I2, OR52E1, OR52A5 and OR56A5 (the ORs of the invention), as natural receptors for carboxylic acids present in human sweat. The invention encompasses the use of the interaction of these OR polypeptides and carboxylic acids as the basis of screening assays for agents that modulate the activity of the ORs of the invention.

The invention also encompasses kits for performing screening methods based upon the interaction of the 7 ORs invention with carboxylic acids.

The invention encompasses a method of identifying an agent that modulates the activity of one or more of the ORs of the invention, said method comprising: a) contacting an OR polypeptide with a carboxylic acid in the presence and in the absence of a candidate modulator under conditions permitting the binding of said carboxylic acid to said OR polypeptide; and b) measuring the binding of said OR polypeptide to said carboxylic acid, wherein a decrease in binding in the presence of said candidate modulator, relative to the binding in the absence of the candidate modulator, identifies the candidate modulator as an agent that modulates the activity of OR of the invention.

The invention thus provides for a method for identifying an agent that modulates the function of one or more Olfactory Receptors (ORs) selected from the group consisting of: OR52L1, OR52E8, OR52B2, OR51I2, OR52E1, OR52A5 and OR56A5 comprising the steps of:

a) contacting said one or more ORs with one or more carboxylic acid(s) selected from the group of consisting of: butanoic acid, isovaleric acid, pentanoic acid, hexanoic acid, 2-methylhexanoic acid, 3-methylhexanoic acid, (E)-3-methly-2-hexenoic acid, 3-hydroxy-3-methylhexanoic acid, heptanoic acid, 2-methylheptanoic acid, octanoic acid, 4-ethyloctanoic acid, nonanoic acid, decanoic acid, undecanoic acid and benzoic acid, in the presence and in the absence of said agent under conditions permitting the binding of said carboxylic acid(s) to said ORs or permitting the activation of said ORs by said carboxylic acid(s), b) comparing the binding of said one or more ORs to said one or more carboxylic acid(s), or the activity of said one or more ORs, in the presence and in the absence of said agent, wherein a difference in binding or activity in the presence of said agent, relative to the binding or activity in the absence of the agent, identifies the agent as an agent that modulates the function of said one or more ORs in response to said one or more carboxylic acid(s).

In a preferred embodiment, said agent is tested for influencing the binding of said carboxylic acids to all 7 ORs listed therein, or for influencing the activation of all 7 ORs listed therein by said carboxylic acids.

In a further embodiment, said agent is tested for influencing the binding of pentanoic acid to OR52L1, or for influencing the activation of OR52L1 by pentanoic acid.

In another embodiment said agent is tested for influencing the binding of 3-hydroxy-3-methylhexanoic acid to OR52E8, or for influencing the activation of OR52E8 by 3-hydroxy-3-methylhexanoic acid.

In a next embodiment, said agent is tested for influencing the binding of hexanoic acid, heptanoic acid, octanoic acid, nonanoic acid, decanoic acid, or undecanoic acid to OR52B2, or for influencing the activation of OR52B2 by hexanoic acid, heptanoic acid, octanoic acid, nonanoic acid, decanoic acid, or undecanoic acid.

In another embodiment said agent is tested for influencing the binding of butanoic acid, isovaleric acid, pentanoic acid, hexanoic acid, 2-methylhexanoic acid, 3-methylhexanoic acid, (E)-3-methyl-2-hexanoic acid, or benzoic acid to OR51I2, or for influencing the activation of OR51I2 by butanoic acid, isovaleric acid, pentanoic acid, hexanoic acid, 2-methylhexanoic acid, 3-methylhexanoic acid, (E)-3-methyl-2-hexanoic acid, or benzoic acid In a further embodiment said agent is tested for influencing the binding of butanoic acid to OR52E1, or for influencing the activation of OR52E1 by butanoic acid.

In yet another embodiment said agent is tested for influencing the binding of 4-ethyloctanoic acid to OR52A5, or for influencing the activation of OR52A5 by 4-ethyloctanoic acid.

In another embodiment, said agent is tested for influencing the binding of hexanoic acid, heptanoic acid, 2-methylheptanoic acid, octanoic acid, nonanoic acid, decanoic acid, or undecanoic acid to OR56A5, or for influencing the activation of OR56A5 by hexanoic acid, heptanoic acid, 2-methylheptanoic acid, octanoic acid, nonanoic acid, decanoic acid, or undecanoic acid.

Preferably, said one or more OR polypeptides is defined by the amino acid sequence of SEQ ID NOs. 2, 4, 6, 8, 10, 12 or 14. The invention further encompasses a method of detecting in a sample the presence of an agent that modulates the activity of the OR of the invention in a sample, said method comprising a) contacting an OR polypeptide with carboxylic acid in the presence and in the absence of said sample under conditions permitting the binding of said carboxylic acid to said OR polypeptide; and b) measuring the binding of said OR polypeptide to said carboxylic acid, wherein a decrease in binding in the presence of the sample, relative to the binding in the absence of the candidate modulator, indicates the presence, in the sample of an agent that modulates the activity of an OR in said sample.

The invention further encompasses a method of identifying an agent that modulates the function of the OR of the invention said method comprising: a) contacting an OR polypeptide with a carboxylic acid in the presence and in the absence of a candidate modulator, under conditions permitting activation of said OR polypeptide by carboxylic acid; and b) measuring a signaling activity of said OR polypeptide, wherein a change in the activity in the presence of said candidate modulator relative to the activity in the absence of said candidate modulator identifies said candidate modulator as an agent that modulates the function of said OR.

The invention further encompasses a method of identifying an agent that modulates the function of the OR of the invention, said method comprising: a) contacting an OR polypeptide with a candidate modulator; b) measuring a signaling activity of said OR polypeptide in the presence of said candidate modulator; and c) comparing the activity measured in the presence of said candidate modulator to said activity measured in a sample in which said OR polypeptide is contacted with carboxylic acid at its $EC_{50}$, wherein said candidate modulator is identified as an agent that modulates the function of the OR when the amount of the activity measured in the presence of the candidate modulator is at least 10% of the amount induced by said carboxylic acid present at its $EC_{50}$.

The invention further encompasses a method of detecting in a sample the presence of an agent that modulates the function of an OR of the invention, said method comprising: a) contacting an OR polypeptide with carboxylic acid in the presence and in the absence of said sample; b) measuring a signaling activity of said OR polypeptide; and c) comparing the amount of said activity measured in a reaction containing OR and carboxylic acid without said sample to the amount of said activity measured in a reaction containing OR, carboxylic acid and said sample, wherein a change in said activity in the presence of said sample relative to the activity in the absence of said sample indicates the presence of an agent that modulates the function of OR in said sample.

The invention further encompasses a method of detecting in a sample the presence of an agent that modulates the function of an OR of the invention, said method comprising: a) contacting an OR polypeptide with said sample; b) measuring a signaling activity of said OR polypeptide in the presence of said sample; and c) comparing said activity measured in the presence of said sample to said activity measured in a reaction in which said OR polypeptide is contacted with carboxylic acid present at its $EC_{50}$, wherein an agent that modulates the function of the OR is detected if the amount of the activity measured in the presence of said sample is at least 10% of the amount induced by the carboxylic acid present at its $EC_{50}$.

According to the present invention, when using binding methods the carboxylic acid may be detectably labeled. In said methods, the carboxylic acid may be detectably labeled with a moiety selected from the group consisting of a radioisotope, a fluorophore, and a quencher of fluorescence.

In one embodiment of any one of the preceding methods, the contacting is performed in or on a cell expressing said OR polypeptide. According to the present invention, said cell may be, but is not limited to, Human embryonic kidney cells (Hek293), Chinese hamster cells (CHO), Monkey cells (COS), primary olfactory cells, *Xenopus* cells, insect cells, yeast or bacteria.

In another embodiment of any one of the preceding methods, the contacting is performed in or on synthetic liposomes (see Tajib et al., 2000, Nature Biotechnology 18: 649-654, which is incorporated herein by reference) or virus-induced budding membranes containing an OR polypeptide (see WO0102551, 2001, incorporated herein by reference).

In another embodiment of any one of the preceding methods, the method is performed using a membrane fraction from cells expressing said OR polypeptide.

In a preferred embodiment of either one of the preceding methods, the method is performed on a protein chip.

In another preferred embodiment of either one of the preceding methods, the measuring is performed using a method selected from label displacement, surface plasmon resonance, fluorescence resonance energy transfer, fluorescence quenching, and fluorescence polarization.

In another embodiment of either one of the preceding methods, the agent is selected from the group consisting of a peptide, a polypeptide, an antibody or antigen-binding fragment thereof, a lipid, a carbohydrate, a nucleic acid, and a small organic molecule.

According to the present invention, when a functional assay is used, the step of measuring a signaling activity of the OR of the invention may comprise detecting a change in the level of a second messenger.

In another embodiment, the step of measuring a signaling activity comprises measurement of guanine nucleotide binding/coupling or exchange, adenylate cyclase activity, cAMP, Protein Kinase C activity, Protein Kinase A activity phosphatidylinositol breakdown, diacylglycerol, inositol triphosphate, intracellular calcium, calcium flux, arachidonic acid, MAP kinase activity, tyrosine kinase activity, melanophore assay, receptor initialization assay, or reporter gene expression. When the G-protein binding/coupling or exchange is measured, of all Ga subunits possible preferably the behaviours of GTP-binding protein G protein alpha-olf subunit (olfactory), also G-olf, is studied. The sequence of the human G-olf subunit has been deposited previously at the Genebank under accession number L10665. However, G-olf subunits of other species may be used and studied.

In a preferred embodiment, the measuring of the signaling activity comprises using a fluorescence or luminescence assay. Fluorescence and luminescence assays may comprise the use of $Ca^{2+}$ sensitive fluorophores including fluo3, Fluo4 or Fura, (Molecular probes); Ca3-kit family (Molecular Device) and aequorin. Furthermore, said assays may apply an automated fluorometric or luminescent reader such as FDSS (Hammamatsu) or FLIPR (Molecular Device).

The invention further encompasses a method of modulating the activity of an OR of the invention in a cell, said method comprising the step of delivering to said cell, a carboxylic acid or agent that modulates the activity of an OR polypeptide, such that the activity of the OR is modulated.

In another embodiment of any one of the preceding methods, the method is a high throughput screening method.

In another embodiment of any one of the preceding methods, the agent is part of a chemical library or animal organ extracts.

According to the present invention, the agent identified or detected by any of the preceeding methods, or the composition comprising said agent, may be used to counteract sweat malodour. Alternatively, these may be used for the preparation of odorant blockers or odorant antagonists. For instance an OR blocker or antagonist may be used as a deodorant. An OR blocker or antagonist may be added to a fragrance or perfume formulation already used as a deodorant to reinforce its efficacy.

The present invention also encompasses a composition comprising an isolated OR polypeptide and a carboxylic acid. In a preferred embodiment, said composition encompasses all 7 ORs identified herein, or any combination thereof of 2, 3, 4, 5, or 6 receptors.

The present invention further relates to the use of carboxylic acids for the production of a kit for screening agents that modulate the signaling of OR of the invention, or in combination with OR of the invention for the production of a kit to screen odorant blockers or odorant antagonists.

In addition, the present invention encompasses the use of a carboxylic acid present in mammalian sweat as a ligand for OR of the invention.

The present invention also relates to an antibody recognizing the carboxylic acid/OR of the invention complex or fragments thereof.

The invention further encompasses a kit comprising an isolated OR polypeptide or several isolated OR polypeptides, a carboxylic acid and packaging materials therefore; an isolated polynucleotide encoding an OR polypeptide or several isolated polynucleotides encoding an OR polypeptide, a carboxylic acid, and packaging materials therefore; a kit comprising a cell expressing an OR polypeptide or membranes thereof or several cells expressing an OR polypeptide or membranes thereof, a carboxylic acid and packaging materials therefore. Said cell may be transformed with a polynucleotide encoding said OR. In a preferred embodiment, said kit encompasses all 7 ORs identified herein, or any combination thereof of 2, 3, 4, 5, or 6 receptors and their respective carboxylic acids.

BRIEF DESCRIPTION OF THE FIGURES

FIG. 1A-FIG. 1C show the DNA and corresponding polypeptide sequences encoding the seven Olfactory Receptors (ORs) of the invention.

FIGS. 2A-FIG. 2J correspond to a concentration-response analysis of the seven receptors of the invention with their different activators that are all carboxylic acids found in sweat. These analyses have been performed according to the procedure described in "Experimental procedure"

DETAILED DESCRIPTION OF THE INVENTION

Definitions

As used herein, the term "Olfactory Receptor polypeptides (ORs)" in general refers to polypeptides from the G protein coupled receptor family generated in olfactory neurons. ORs may have the ability to interact with odorant molecules and to transduce the odorant signal. The terms "Olfactory Receptors (ORs) according to the invention" or "Olfactory Receptor polypeptides according to the invention" refer to the group of 7 olfactory receptors that have been shown in the present invention to be able to selectively detect carboxylic acids. Examples of olfactory receptors according to the invention include, but are not limited to polypeptides having at least 80% amino acid identity, and preferably 90%, 95%, 96%, 97%, 98%, 99% or higher, including 100% amino acid identity, to the sequence represented in FIG. 1A-FIG. 1C (SEQ ID NOs 2, 4, 6, 8, 10, 12 and 14). Said homology may relate to the whole polypeptide or only part of the polypeptide such as CDR domain (ligand-binding domain of the receptor). According to Pilpel and Lancet (Protein Science 8:969-977, 1999) the CDR domain of a GPCR may be defined following the indications published: TM3-#4, TM3-#8, TM3-#11, TM3-#12, TM3-#15, TM4-#11, TM4-#15, TM4-#19, TM4-#22, TM4-#23, TM4-#26, TM5-#3, TM5-#6, TM5-#7, TM5-#10, TM5-#11 and TM5-#13, wherein TMx indicates the transmembrane region of said receptor, and # indicates the amino acid position whithin said region.

As used herein, the term "OR polynucleotide" refers to a polynucleotide that encodes the OR polypeptides as defined herein. Preferably, said polynucleotide has an identity of at least 80% or more, preferably 90%, 95%, 96%, 97%, 98%, 99% or higher, including 100% nucleic acid identity, to the sequence represented in FIG. 1A-FIG. 1C (SEQ ID NOs 1, 3, 5, 7, 9, 11 and 13).

As used herein, the term "OR binding" refers to specific binding of an odorant molecule by an OR polypeptide. Examples of odorant molecules include, but are not limited to carboxylic acids, esters, alcohols and amines.

As used herein, the term "OR signaling activity" refers to the initiation or propagation of signaling by an OR polypeptide. OR signaling activity is monitored by measuring a detectable step in a signaling cascade by assaying one or more of the following: stimulation of GDP for GTP exchange on a G protein and most particularly G-olf; alteration of adenylate cyclase activity; protein kinase C modulation; protein kinase A modulation; phosphatidylinositol breakdown (generating second messengers diacylglycerol, and inositol triphosphate); intracellular calcium flux; activation of MAP kinases; modulation of tyrosine kinases; internalization assay; modulation of gene or reporter gene activity; or melanophore assay. A detectable step in a signaling cascade is considered initiated or mediated if the measurable activity is altered by 10% or more above or below a baseline established in the substantial absence of a carboxylic acid relative to any of the OR activity assays described herein. The measurable activity can be measured directly, as in, for example, measurement of cAMP or diacylglycerol levels. Alternatively, the measurable activity can be measured indirectly, as in, for example, a reporter gene assay. For most of these assays, kits are commercially available.

Carboxylic acids according to the invention are carboxylic acids present in mammalian sweat, preferably human sweat, which participate in or are important for the genesis of sweat malodour (cf. e.g. Table 1).

A "blocker" or "blocking compound" according to the invention is a molecule that attenuates or abolishes the perception of an odor elicited by one or more odorant molecules. A blocker may act by interacting with an OR that transduces the said odor or by interacting with the natural ligand for the receptor. A "blocking compound" of the invention can decrease the intracellular response induced by an agonist, for example a carboxylic acid present in human sweat, by at least 10%, preferably 15-25%, more preferably 25-50% and most preferably, 50-100%. A "blocker" can also refer to a nucleotide sequence encoding a blocker of the invention. A blocker, useful according to the present invention, includes, but is not limited to an antibody, small molecule, aptamer, photoaptamer, modified natural ligand, etc. which specifically binds to at least a portion of an OR which is required for signal transduction through carboxylic acids (such as the ligand binding site), or which is capable of blocking or reducing (e.g., by at least 10%) the signal transduction pathway which is coupled to the OR. Preferably, the blocking agent is preferably volatile, or can be made volatile in combination with appropriate solvents or additives.

As used herein, an "antagonist" is a ligand which binds to a receptor and inhibits the intracellular response induced by a ligand or an agonist, for example a carboxylic acid present in human sweat, by at least 10%, preferably 15-25%, more preferably 25-50% and most preferably, 50-100%, as compared to the intracellular response in the presence of an agonist and in the absence of an antagonist. The antagonist may be competitive i.e. it binds at the same site as the agonist or ligand, but does not activate an intracellular response initiated by an active form of the receptor and therefore avoids the activation by said ligand or agonist. Alternatively, the antagonist may be non-competitive, i.e. it binds to a site other than the agonist or ligand binding site and blocks the receptor in an inactive conformation and therefore avoids the transduction of the olfactory signal by the agonist.

As used herein, "natural ligand" refers to a naturally occurring ligand which binds to a receptor in a manner that is at least equivalent to a carboxylic acid present in human sweat, such as the carboxylic acids as exemplified herein. A "natural ligand" does not refer to an engineered ligand that is not found in nature and that is engineered to bind to a receptor, where it did not formerly do so in a manner different, either in degree or kind, from that which it was engineered to do. Such an engineered ligand is no longer naturally-occurring but is "non-natural" and is derived from a naturally occurring molecule.

As used herein, a "modulator" refers to a compound that increases or decreases the cell surface expression of a receptor of the invention, increases or decreases the binding of a ligand to ORs of the invention, or any compound that increases or decreases the intracellular response initiated by an active form of the ORs of the invention, either in the presence or absence of a ligand for the receptor, for example a carboxylic acid present in human sweat. A modulator includes an antagonist, or blocker, as defined herein. A modulator can be for example, a small molecule, a polypeptide, a peptide, an antibody or antigen-binding fragment thereof, a lipid, a carbohydrate, a nucleic acid, an aptamer, a photoaptamer, or a small chemical compound or small organic molecule. Candidate modulators can be natural or synthetic compounds, including, for example, synthetic small molecules, compounds contained in extracts of animal, plant, bacterial or fungal cells, as well as conditioned medium from such cells.

As used herein, the terms "increase" and "decrease" refer to a change in amount of ligand binding to the ORs of the invention and/or cell signalling through ORs of the invention of at least 10%. An "increase" or "decrease" in binding or signalling is preferably measured in response to contacting ORs of the invention with a ligand in the presence of a candidate modulator, wherein the change in binding or signalling is relative to the binding or signalling in the absence of the candidate modulator.

As used herein, the term "small molecule" refers to a compound having a molecular mass of less than 3000 Daltons, preferably less than 2000 or 1500, still more preferably less than 1000, and most preferably less than 600 Daltons. A "small organic molecule" is a small molecule that comprises carbon.

As used herein, the terms "change", "difference", "decrease", or "increase" as applied to e.g., binding or signalling activity or amount of a substance refer to an at least 10% increase or decrease in binding, signalling activity, or for example, level of mRNA, polypeptide or ligand relative to a standard in a given assay.

As used herein, the term "conditions permitting the binding of carboxylic acid to an OR of the invention" refers to conditions of, for example, temperature, salt concentration, pH and protein concentration under which the OR binds a carboxylic acid. Exact binding conditions will vary depending upon the nature of the assay, for example, whether the assay uses viable cells or only a membrane fraction of cells. However, because the ORs of the invention are cell surface proteins, favored conditions will generally include physiological salt (90 mM) and pH (about 7.0 to 8.0). Temperatures for binding can vary from 15° C. to 37° C., but will preferably be between room temperature and about 30° C. The concentration of carboxylic acid in a binding reaction will also vary from about 0.5 to 2 µM, but will preferably be about 1 µM.

As used herein, the term "sample" refers to the source of molecules being tested for the presence of an agent or modulator compound that modulates binding to or signalling activity of an OR of the invention. A sample can be an environmental sample, a natural extract of animal, plant, yeast or bacterial cells or tissues, a clinical sample, a synthetic sample, or a conditioned medium from recombinant cells or from a fermentation process.

As used herein, a "tissue" is an aggregate of cells that perform a particular function in an organism. The term "tissue" as used herein refers to cellular material from a particular physiological region. The cells in a particular tissue can comprise several different cell types. A non-limiting example of this would be brain tissue that further comprises neurons and glial cells, as well as capillary endothelial cells and blood cells, all contained in a given tissue section or sample. In addition to solid tissues, the term "tissue" is also intended to encompass non-solid tissues, such as blood.

As used herein, the term "membrane fraction" refers to a preparation of cellular lipid membranes containing an OR of the invention. As the term is used herein, a "membrane fraction" is distinct from a cellular homogenate, in that at least a portion (i.e., at least 10%, and preferably more) of non-membrane-associated cellular constituents has been removed. The term "membrane associated" refers to those cellular constituents that are either integrated into a lipid membrane or are physically associated with a component that is integrated into a lipid membrane.

As used herein, the term "second messenger assay" preferably comprises the measurement of guanine nucleotide binding or exchange, adenylate cyclase, intra-cellular cAMP, intracellular inositol phosphate, intra-cellular diacylglycerol concentration, arachidonic acid concentration, MAP kinase(s) or tyrosine kinase(s), protein kinase C activity, or reporter gene expression or an aequorin-based assay according to methods known in the art and defined herein.

As used herein, the term "second messenger" refers to a molecule, generated or caused to vary in concentration by the activation of a G-Protein Coupled Receptor that participates in the transduction of a signal from that GPCR. Non-limiting examples of second messengers include cAMP, diacylglycerol, inositol triphosphate, arachidonic acid release, inositol triphosphate and intracellular calcium. The term "change in the level of a second messenger" refers to an increase or decrease of at least 10% in the detected level of a given second messenger relative to the amount detected in an assay performed in the absence of a candidate modulator.

As used herein, the term "aequorin-based assay" refers to an assay for GPCR activity that measures intracellular calcium flux induced by activated GPCRs, wherein intracellular calcium flux is measured by the luminescence of aequorin expressed in the cell.

As used herein, the term "binding" refers to the physical association of a molecule (e.g., a ligand such as a carboxylic acid or an antibody) with a receptor (e.g., OR of this invention). As the term is used herein, binding is "specific" if it occurs with an $EC_{50}$ or a Kd of 1 mM less, generally in the range of 1 mM to 10 nM For example, binding is specific if the $EC_{50}$ or Kd is 1 mM, 500 µM, 100 µM, 10 µM, 9.5 µM, 9 µM, 8.5 µM, 8 µM, 7.5 µM, 7 µM, 6.5 µM, 6 µM, 5.5 µM, 5 µM, 4.5 µM, 4 µM, 3.5 µM, 3 µM, 2.5 µM, 2 µM, 1.5 µM, 1 µM, 750 nM, 500 nM, 250 nM or 100 nM or less.

As used herein, the term "$EC_{50}$," refers to that concentration of a compound at which a given activity, including binding of a carboxylic acid or other ligand and a functional activity of a OR, is 50% of the maximum for that OR activity measurable using the same assay in the absence of compound. Stated differently, the "$EC_{50}$" is the concentration of compound that gives 50% activation, when 100% activation is set at the amount of activity that does not increase with the addition of more agonist.

As used herein, the term "saturation" refers to the concentration of a carboxylic acid present in human sweat or other ligand at which further increases in ligand concentration fail to increase the binding of ligand or OR-specific signalling activity.

As used herein, the term "$IC_{50}$" is the concentration of an antagonist or blocker that reduces the maximal activation of an OR of the invention by 50%.

As used herein, the term "decrease in binding" refers to a decrease of at least 10% in the amount of ligand binding detected in a given assay with a known or suspected modulator of OR of the invention relative to binding detected in an assay lacking that known or suspected modulator.

As used herein, the term "G-Protein coupled receptor," or "GPCR" refers to a membrane-associated polypeptide with 7 alpha helical transmembrane domains. Functional GPCR's associate with a ligand or agonist and also associate with and activate G-proteins. OR polypeptides of the invention are GPCRs.

As used herein, the term "antibody" is the conventional immunoglobulin molecule, as well as fragments thereof which are also specifically reactive with one of the subject polypeptides. Antibodies can be fragmented using conventional techniques and the fragments screened for utility in the same manner as described herein below for whole antibodies. For example, F(ab)2 fragments can be generated by treating antibody with pepsin. The resulting F(ab)2 fragment can be treated to reduce disulfide bridges to produce Fab fragments. The antibody of the present invention is further intended to include bispecific, single-chain, and chimeric and humanised molecules having affinity for a polypeptide conferred by at least one CDR region of the antibody. In preferred embodiments, the antibody further comprises a label attached thereto and able to be detected, (e.g., the label can be a radioisotope, fluorescent compound, chemiluminescent compound, enzyme, or enzyme co-factor). The antibodies, monoclonal or polyclonal and their hypervariable portion thereof (FAB, FAB'', etc.) as well as the hybridoma cell producing the antibodies are a further aspect of the present invention which find a specific industrial application in the field of diagnostics and monitoring of specific diseases, preferably the ones hereafter described. Inhibitors according to the invention include but are not limited to labeled monoclonal or polyclonal antibodies or hypervariable portions of the antibodies.

As used herein, the term "OR constitutive activity" refers to a measurable activity of an olfactory receptor expressed into a cell that occurs spontaneously without addition of a ligand for the said olfactory receptor.

As used herein, the term "inverse agonist" refers to a molecule that binds to and decreases or suppresses the constitutive activity of an OR.

The invention relates to the discovery that carboxylic acids present in human sweat are natural ligands for a specific groups of olfactory receptors, the OR polypeptides as defined herein. The OR/carboxylic acids interaction is useful for screening assays for agents that modulate such an interaction and thus the function of the OR. This OR/carboxylic acid interaction also provides for the identification of modulators which could be of interest in industry.

Assays for the Identification of Agents that Modulate the Activity of ORs

Agents that modulate the activity of ORs can be identified in a number of ways that take advantage of the interaction of said receptors with carboxylic acids. For example, the ability to reconstitute OR/carboxylic acid binding either in vitro, on cultured cells or in vivo provides a target for identification of agents that disrupt that binding. Assays based on disruption of binding can identify agents, such as small organic molecules, from libraries or collections of such molecules. Alternatively, such assays can identify agents in samples or extracts from natural sources, including plant, fungal, or bacterial extracts or even human tissue samples. Modulators of OR/carboxylic acid binding can then be screened using a binding assay or a functional assay that measures downstream signaling through the said receptor. Both binding assays and functional assays are validated using carboxylic acids.

Another approach that uses the OR/carboxylic acid interaction more directly to identify agents that modulate OR function measures changes in OR downstream signaling induced by candidate agents or candidate modulators. These functional assays can be performed in isolated cell membrane fractions or on cells expressing the receptor on their surfaces.

The following description provides methods for both binding and functional assays based upon the interaction of ORs and carboxylic acids.

A. OR Polypeptides.

Assays using the interaction of OR polypeptides and carboxylic acids require a source of OR polypeptides. The polynucleotide and polypeptide sequence of human ORs are presented herein in FIG. 1A-FIG. 1C. The human OR52L1, OR52E8, OR52B2, OR51I2, OR52E1, OR52A5 and OR56A5 polynucleotide sequences are also available at GenBank Accession No.s NM_001005173 (SEQ ID NO.1), NM_001005168 (SEQ ID NO.3), NM_001004052 (SEQ ID NO.5), NM_001004754 (SEQ ID NO.7), NG_033197 (SEQ ID NO:9), NM_001005160 (SEQ ID NO.11), NM_001146033 (SEQ ID NO.13), respectively. The polypeptide sequences are also recorded at accession Nos. Q8NGH7 (SEQ ID NO:2), Q61FG1 (SEQ ID NO.4), Q96RD2 (SEQ ID NO.6), Q9H344 (SEQ ID NO.8), Q8NGJ3 (SEQ ID NO.10), Q9H2C5 (SEQ ID NO.12), and P0C7T3 (SEQ ID NO.14) respectively in the Uniprot database.

One skilled in the art can readily amplify an OR sequence from a sample containing mRNA encoding the protein through basic PCR and molecular cloning techniques using primers or probes designed from the known sequences. Also, since OR genes are intron-less genes, a person skilled in the art can amplify an OR sequence from genomic DNA.

The expression of recombinant polypeptides is well known in the art. Those skilled in the art can readily select vectors and expression control sequences for the expression of OR polypeptides according to the invention in eukaryotic or prokaryotic cells. OR polypeptides are preferably associated with the cell membrane or synthetic liposomes in order to have binding or signaling function. Methods for the preparation of cellular membrane fractions are well known in the art, e.g., the method reported by Hubbard & Cohn, 1975, J. Cell Biol. 64: 461-479, which is incorporated herein by reference. In order to produce membranes comprising OR polypeptides, one can e.g. apply such membrane isolation techniques to cells endogenously or recombinantly expressing one of the OR polypeptides of the invention. Alternatively, OR polypeptides can be integrated into membrane preparations by dilution of detergent solution of the polypeptide (see, e.g., Salamon et al., 1996, Biophys. J. 71:283-294, which is incorporated herein by reference).

B. Carboxylic Acids Present in Sweat.

The structure of such carboxylic acids are well known by a skilled person. In addition, the person skilled in the art may easily derive equivalent acids from said structure and may easily test if said equivalents are able to bind and/or modulate the OR polypeptides. Carboxylic acids may be isolated from natural samples, or chemically synthesized.

Methods which can be used to quantify said acids may be, but are not limited to, a) for extraction and purification: solvent extraction, oil extraction, vapour extraction, CO2 super-critical extraction, liquid chromatography, distillation, gas chromatography; b) for quantifying: gas chromatography, liquid chromatography and mass spectrometry. Said methods are well known in the art.

Carboxylic acids may be used in purified form or used as compositions. The amounts of the acid necessary in a given binding or functional assay according to the invention will vary depending upon the assay, but will generally use 1 µM to 1000 µM of labeled and 10 µM to 10 mM of unlabeled acid per assay. If necessary for a given assay, a carboxylic acid can be labeled by incorporation or addition of radioactive labels as pointed out above.

C. Assays to Identify Modulators of ORs Activity

The discovery that carboxylic acids are ligands of seven ORs belonging to the class 1 olfactory receptor family permits the development of screening assays to identify modulators of ORs activity. The screening assays will have two general approaches.

1) Ligand binding assays, in which cells expressing one or more ORs according to the invention, membrane extracts from such cells, or immobilized lipid membranes comprising one or more ORs according to the invention are exposed to a labeled carboxylic acid known to bind said one or more ORs and a candidate compound. Following incubation, the reaction mixture is measured for specific binding of the labeled carboxylic acid to said ORs. Compounds that interfere with or displace labeled carboxylic acid from the ORs can be identified as modulators, preferably blockers or antagonists of OR activities. Functional analysis can be performed on positive compounds to determine in which of these categories they fit.

Binding of a compound may be classified into 3 main categories: competitive binding, non-competitive binding and uncompetitive binding. A competitive binding compound resembles a second (reference) compound and binds to the same binding pocket of a target molecule (here receptor). Upon addition, the competitive binding compound displaces said second compound from said target. A non-competitive binding compound does not bind to the same binding pocket of the target molecule as a second (reference) compound but may interact with the effect of said second compound on said target molecule. The second compound is not displaced upon addition of the non-competitive binding compound. An uncompetitive-binding compound binds to the target molecule when a second compound is already bound. Cooperative binding means that a compound facilitates the binding of another compound which may be a reference compound. The cooperative effect is thus seen in the analysis of the Kd of said other compound.

2) Functional assays, in which a signaling activity of ORs is measured.

a) For agonist screening, cells expressing ORs or membranes prepared from them are incubated with a candidate compound, and a signaling activity of ORs is measured. The assays are validated using a carboxylic acid as agonist, and the activity induced by compounds that modulate receptor activity is compared to that induced by the carboxylic acid. An agonist or partial agonist will have a maximal biological activity corresponding to at least 10% of the maximal activity of the carboxylic acid when the agonist or partial agonist is present at 100 µM or less, and preferably will have 50%, 75%, 100% or more, including 2-fold, 5-fold, 10-fold or more activity than the carboxylic acid.

b) For antagonist screening, cells expressing ORs or membranes isolated from them are assayed for signaling activity in the presence of a carboxylic acid with or without a candidate compound. Antagonists will reduce the level of carboxylic acid-stimulated receptor activity by at least 10%, relative to reactions lacking the antagonist.

c) For inverse agonist screening, cells expressing constitutive OR activity or membranes isolated from them are used in a functional assay that measures an activity of the receptor in the absence of carboxylic acid ligands. Inverse agonists are those compounds that reduce the constitutive activity of the OR by at least 10%. Overexpression of OR may lead to constitutive activation. OR can be overexpressed by placing it under the control of a strong constitutive promoter, e.g., the CMV early promoter. Alternatively, certain mutations of conserved GPCR amino acids or amino acid domains tend to lead to constitutive activity. See for example: Kjelsberg et al., 1992, J. Biol. Chem. 267:1430; McWhinney et al., 2000. J. Biol. Chem. 275:2087; Ren et al., 1993, J. Biol. Chem. 268:16483; Samama et al., 1993, J. Biol. Chem. 268:4625; Parma et al., 1993, Nature 365:649; Parma et al., 1998, J. Pharmacol. Exp. Ther. 286:85; and Parent et al., 1996, J. Biol. Chem. 271:7949.

Ligand Binding and Displacement Assays:

One can use OR polypeptides expressed in a cell, or isolated membranes containing receptor polypeptides, along with a carboxylic acid in order to screen for compounds that inhibit the binding of carboxylic acids to OR polypeptides. When identified in an assay that measures binding or carboxylic acid displacement alone, compounds will have to be subjected to functional testing to determine whether they act as agonists, antagonists or inverse agonists.

For displacement experiments, cells expressing an OR polypeptide (generally 25,000 cells per assay or 1 to 100 µg of membrane extracts) are incubated in binding buffer (e.g., 50 mM Hepes pH 7.4; 1 mM $CaCl_2$; 0.5% Bovine Serum Albumin (BSA) Fatty Acid-Free; and 0.5 mM $MgCl\,2$) for 1.5 hrs (at, for example, 27° C.) with labeled carboxylic acid in the presence or in the absence of increasing concentrations of a candidate modulator. To validate and calibrate the assay, control competition reactions using increasing concentrations of unlabeled carboxylic acid can be performed. After incubation, cells are washed extensively, and bound, labeled carboxylic acid is measured as appropriate for the given label (e.g., scintillation counting, enzyme assay, fluorescence, etc.). A decrease of at least 10% in the amount of labeled carboxylic acid bound in the presence of the candidate modulator indicates displacement of binding by the candidate modulator. Candidate modulators are considered to bind specifically in this or other assays described herein if they displace 50% of the labeled carboxylic acid.

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of carboxylic acid from the aqueous phase to a OR polypeptide immobilized in a membrane on the sensor. This change in mass is measured as resonance units versus time after injection or removal of the carboxylic acid or candidate modulator and is measured using a Biacore Biosensor (Biacore AB). OR polypeptides can be immobilized on a sensor chip (for example, research grade CM5 chip; Biacore AB) in a thin film lipid membrane according to methods described by Salamon et al. (Salamon et al., 1996, Biophys J. 71: 283-294; Salamon et al., 2001, Biophys. J. 80: 1557-1567; Salamon et al., 1999, Trends Biochem. Sci. 24: 213-219, each of which is incorporated herein by reference.). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference). Conditions for carboxylic acid binding to an OR of the invention in an SPR assay can be fine-tuned by one skilled in the art using the conditions reported by Sarrio et al. as a starting point.

SPR can assay for modulators of binding in at least two ways. First, a carboxylic acid can be pre-bound to immobilized OR polypeptide, followed by injection of the candidate modulator at approximately 10 µl/min flow rate and a concentration ranging from 1 nM to 1000 µM, preferably about 100 µM. Displacement of the bound carboxylic acid can be quantified, permitting detection of modulator binding. Alternatively, the membrane-bound carboxylic polypeptide can be pre-incubated with a candidate modulator and challenged with a carboxylic acid. A difference in carboxylic acid binding to the OR exposed to the modulator relative to that on a chip not pre-exposed to the modulator will demonstrate binding. In either assay, a decrease of 10% or more in the amount of carboxylic acid bound is in the presence of candidate modulator, relative to the amount of carboxylic acid bound in the absence of candidate modulator indicates that the candidate modulator inhibits the interaction of the OR and the carboxylic acid. A Biacore system can be plugged to a system identifying candidate modulator such as mass spectrometry, or gas chromatography.

Another method of measuring inhibition of binding of carboxylic acid to OR uses fluorescence resonance energy transfer (FRET). FRET is a quantum mechanical phenomenon that occurs between a fluorescence donor (D) and a fluorescence acceptor (A) in close proximity to each other (usually <100 A of separation) if the emission spectrum of D overlaps with the excitation spectrum of A. The molecules to be tested, e.g., a carboxylic acid and an OR polypeptide, are labeled with a complementary pair of donor and acceptor fluorophores. While close to each other due to the OR/carboxylic acid interaction, fluorescence emitted upon excitation of the donor fluorophore will have a different wavelength from that emitted in response to the excitation wavelength when the molecules are not bound, thus allowing quantification of bound versus unbound polypeptides by measurement of emission intensity at each wavelength. Donor/acceptor pairs of fluorophores with which to label the target molecules are well known in the art.

A variation on FRET uses fluorescence quenching to monitor molecular interactions. One molecule in the interacting pair can be labeled with a fluorophore, and the other with a molecule that quenches the fluorescence of the fluorophore when brought into close apposition with it. A change in fluorescence upon excitation is indicative of a change in the association of the molecules tagged with the fluorophore:quencher pair. Generally, an increase in fluorescence of the labeled OR polypeptide is indicative that carboxylic acid bearing the quencher has been displaced. For quenching assays, a 10% or greater increase in the intensity of fluorescent emission in samples containing a candidate modulator, relative to samples without the candidate modulator, indicates that the candidate modulator inhibits OR/carboxylic acid interaction.

Bioluminescence Resonance Energy Transfer (BRET) is a system for monitoring intermolecular interactions in vivo. The assay is based on non-radiative energy transfer between fusion proteins containing *Renilla* luciferase (Rluc) and e.g. Yellow Fluorescent Protein (YPF) or Green Fluorescent Protein (GFP). The BRET signal is generated by the oxidation of a coelenterazine derivative substrate. Said system may apply a cell-permeable and non-toxic coelenterazine derivative substrate DeepBleuC™ (DBC) and a mutant of the Green Fluorescent Protein (GFP) as acceptor. When the donor and acceptor are in close proximity the energy resulting from the catalytic degradation of the DBC is transferred from Rluc to GFP which will then emit fluorescence at its characteristic wavelength. This method allows higher distance between the two tested molecules and is fluorophore-angle independent.

In addition to the surface plasmon resonance, FRET and BRET methods, fluorescence polarization measurement is useful for quantification of carboxylic acid-receptor binding. The fluorescence polarization value for a fluorescently-tagged molecule depends on the rotational correlation time or tumbling rate. Protein complexes, such as those formed by an OR associating with a fluorescently labeled carboxylic acid, have higher polarization values than uncomplexed, labeled carboxylic acid. The inclusion of a candidate inhibitor of the OR/carboxylic acid interaction results in a decrease in fluorescence polarization, relative to a mixture without the candidate inhibitor, if the candidate inhibitor disrupts or inhibits the interaction of the OR with the carboxylic acid. Fluorescence polarization is well suited for the identification of small molecules that disrupt the formation of polypeptide or protein complexes. A decrease of 10% or more in fluorescence polarization in samples containing a candidate modulator, relative to fluorescence polarization in a sample lacking the candidate modulator, indicates that the candidate modulator inhibits the OR/carboxylic acid interaction.

Another alternative for monitoring OR/carboxylic acid interactions uses a biosensor assay. ICS biosensors have been described by AMBRI (Australian Membrane Biotechnology Research Institute; http//www.ambri.com.au/). In this technology, the association of molecules such as an OR and a carboxylic acid, is coupled to the closing of gramacidin-facilitated ion channels in suspended membrane bilayers and thus to a measurable change in the admittance (similar to impedance) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of OR and carboxylic acid.

It is important to note that in assays of acid-protein interaction, it is possible that a modulator of the interaction need not necessarily interact directly with the domain(s) of the proteins that physically interact. It is also possible that a modulator will interact at a location removed from the site of acid-protein interaction and cause, for example, a conformational change in the OR polypeptides. Modulators (inhibitors or agonists) that act in this manner are nonetheless of interest as agents to modulate the activity of ORs.

Any of the binding assays described can be used to determine the presence of an agent in a sample, e.g., a tissue sample, that binds to OR molecule, or that affects the binding of carboxylic acid to ORs. To do so, OR polypeptides are reacted with carboxylic acid or another ligand in the presence or in the absence of the sample, and carboxylic acid or ligand binding is measured as appropriate for the binding assay being used. A decrease of 10% or more in the binding of carboxylic acid or other ligand indicates that the sample contains an agent that modulates carboxylic acid or ligand binding to OR polypeptides.

Proteins Chips

The methods of the present invention may be applied on protein chips. Said protein chip may be, but is not limited to, a glass slide or a nitrocellulose membrane. Array-based methods for protein chips are well known in the art. The protein arrays preferably comprise one or more OR polypeptides according to the invention or fragments thereof that are responsible for the binding with carboxylic acids. The protein chip preferably comprises all 70R polypeptides according to the invention, or fragments thereof that are responsible for the binding with carboxylic acids.

Functional Assays of Receptor Activity i. GTPase/GTP Binding Assays:

For GPCRs such as OR polypeptides, a measure of receptor activity is the binding of GTP by cell membranes containing receptors. In the method described by Traynor and Nahorski, 1995, Mol. Pharmacol. 47: 848-854, incorporated herein by reference, one essentially measures G-protein coupling to membranes by measuring the binding of labeled GTP to the membrane. For GTP binding assays, membranes isolated from cells expressing the receptor are incubated in a buffer containing 20 mM HEPES, pH 7.4, 100 mM NaCl, and 10 mM MgCl2, 80 µM 35S-GTPγ5 and 3 µM GDP. The assay mixture is incubated for 60 minutes at 30° C., after which unbound labeled GTP is removed by filtration onto GF/B filters. Bound, labeled GTP is measured by liquid scintillation counting. In order to assay for modulation of carboxylic acid-induced OR activity, membranes prepared from cells expressing an OR polypeptide are mixed with a carboxylic acid, and the GTP binding assay is performed in the presence and in the absence of a candidate modulator of OR activity. A decrease of 10% or more in labeled GTP binding as measured by scintillation counting in an assay of this kind containing the candidate modulator, relative to an assay without the modulator, indicates that the candidate modulator inhibits OR activity.

A similar GTP-binding assay can be performed without the carboxylic acid to identify compounds that act as agonists. In this case, the carboxylic acid-stimulated GTP binding is used as a standard. A compound is considered an agonist if it induces at least 50% of the level of GTP binding induced by the carboxylic acid when the compound is present at 1 mM or less, and preferably will induce a level the same as or higher than that induced by the carboxylic acid.

GTPase activity is measured by incubating the membranes containing an OR polypeptide with gamma-32P-GTP. Active GTPase will release the label as inorganic phosphate, which is detected by separation of free inorganic phosphate in a 5% suspension of activated charcoal in 20 mM $H_3PO_4$, followed by scintillation counting. Controls include assays using membranes isolated from cells not expressing OR (mock-transfected), in order to exclude possible non-specific effects of the candidate compound.

In order to assay for the effect of a candidate modulator on OR-regulated GTPase activity, membrane samples are incubated with carboxylic acid, with and without the modulator, followed by the GTPase assay. A change (increase or decrease) of 10% or more in the level of GTP binding or GTPase activity relative to samples without modulator is indicative of carboxylic modulation by a candidate modulator.

ii. Downstream Pathway Activation Assays:
    a. Calcium Flux—the Aequorin-Based Assay.

The aequorin assay takes advantage of the responsiveness of mitochondrial or cytoplasmic apoaequorin to intracellular calcium release or calcium flux (entrance) induced by the activation of GPCRs (Stables et al., 1997, Anal. Biochem. 252:115-126; Detheux et al., 2000, J. Exp. Med., 192 1501-1508; both of which are incorporated herein by reference). Briefly, OR-expressing clones are transfected to coexpress mitochondrial or cytoplasmic apoaequorin and G-alpha-16 or G-olf. Cells are incubated with 5 µM Coelenterazine H or derivates (Molecular Probes) for 4 hours at room temperature, washed in DMEM-F12 culture medium and resuspended at a concentration of 0.5×106 cells/ml. Cells are then mixed with test agonist peptides and light emission by the aequorin is recorded with a luminometer for 30 sec. Results are expressed as Relative Light Units (RLU). Controls include assays using membranes isolated from cells not expressing C356 (mock-transfected), in order to exclude possible non-specific effects of the candidate compound.

Aequorin activity or intracellular calcium levels are "changed" if light intensity increases or decreases by 10% or more in a sample of cells, expressing an OR polypeptide and treated with a candidate modulator, relative to a sample of cells expressing the OR polypeptide but not treated with the candidate modulator or relative to a sample of cells not expressing the OR polypeptide (mock-transfected cells) but treated with the candidate modulator.

When performed in the absence of a carboxylic acid, the assay can be used to identify an agonist or inverse agonist of an OR activity. When the assay is performed in the presence of a carboxylic acid, it can be used to assay for an antagonist.

1) a Fluo3, 4, Fura2, and Calcium3 (Molecular Device) Based-Assay.

Fluorescence-based assays take advantage of calcium fluxes triggered by receptor activation: either calcium entrance through CNG for instance or calcium release from endoplasmic reticulum. Some fluorophores including but not limited to Fluo3, Fluo4 and Fura2 (Molecular Probes) and Calcum3 kit series (Molecular Device) are known to bind calcium. Such fluorophore-calcium complexes emit fluorescence at specific wavelengths. Thereby, upon activation of a G-protein coupled receptor, calcium released from endoplasmic reticulum or entered through CNG binds to fluorophore leading to specific fluorescence emission. OR-overexpressing cells are incubated for 30 to 60 minutes with a solution of 1 to 8 µM fluorophore at 37° C. After thorough washing with saline buffer, 50 µl of the same buffer is poored into each well containing cells (6 to 1536). Tested agonists are then injected into such loaded cells and activation of an OR is followed by fluorescence measurement.

Intracellular calcium levels are "changed" if fluorescence intensity increases or decreases by 10% or more in a sample of cells, expressing an OR polypeptide and treated with a candidate modulator, relative to a sample of cells expressing an OR polypeptide but not treated with the candidate modulator or relative to a sample of cells not expressing an OR polypeptide (mock-transfected cells) but treated with the candidate modulator.

2) Depolarization/Hyperpolarization Membrane Assay (DiBac Fluorophore for Instance).

The principle of this assay is to follow depolarization of the cell membrane. The anionic probe DiBAC4(3) partitions between intra- and extracellular compartments in a membrane potential-dependent manner. With increasing membrane potential (depolarization), the probe further partitions into the cell resulting in an increase of fluorescence. Conversely, hyperpolarization leads to a decrease of fluorescence due to dye extrusion.

The DiBAC4(3) probe is excited with a wavelength of 488 nm, and emits at a wavelength of 540 nm.

On the day of the experiment, add the glucose to the assay buffer (saline buffer) to a final concentration of 10 mM and the DiBAC4(3) probe to a final concentration of 5 µM. Maintain the assay buffer at 37° C. Remove the cell culture medium and rinse twice each well containing OR-overexpressing cells with 200 µl of pre-heated assay buffer. Place 180 µl of Assay buffer containing DiBAC4(3) and incubate the cells for 30 min at the appropriate temperature. Cell plates will be ready for assay after these 30 mins. incubation. Collect baseline for 2 mins. prior any addition. Add 20 µl of candidate modulators to the appropriate well and collect the data for an additional 25 mins.

Membrane polarization is "changed" if fluorescence intensity increases or decreases by 10% or more in a sample of cells, expressing an OR polypeptide and treated with a candidate modulator, relative to a sample of cells expressing an OR polypeptide but not treated with the candidate modulator or relative to a sample of cells not expressing an OR polypeptide (mock-transfected cells) but treated with the candidate modulator.

3) Melanophore Assay.

The melanophore assay is a color-based assay. Basically cells used for this assay are derived from skin of the frog *Xenopus Laevis*. These immortalized cells contain melanosomes, which are organelles containing dark pigment. Activation of endogenous or recombinant GPCR that trigger activation of adenylate cyclase or phospholipase C lead to melanosome dispersion and therefore cell darkening. Alternatively, a GPCR that inhibits adenylate cyclase or phospholipase C leads to cell lightening. Thereby, instead of measuring concentrations of second messenger, one can easily pinpoint hit observing cell coloration change. This color change can easily be quantified on a microplate reader measuring absorbance at 650 nM or by examination on a video imaging system.

b. Adenylate Cyclase Assay:

Assays for adenylate cyclase activity are described by Kenimer & Nirenberg, 1981, Mol. Pharmacol. 20: 585-591, incorporated herein by reference. That assay is a modification of the assay taught by Solomon et al., 1974, Anal. Biochem. 58: 541-548, also incorporated herein by reference. Briefly, 100 μl reactions contain 50 mM Tris-Hcl (pH 7.5), 5 mM MgCl2, 20 mM creatine phosphate (disodium salt), 10 units (71 μg of protein) of creatine phosphokinase, 1 mM α-32P-ATP (tetrasodium salt, 2 μCi), 0.5 mM cyclic AMP, G-3H-labeled cyclic AMP (approximately 10,000 cpm), 0.5 mM Ro20-1724, 0.25% ethanol, and 50-200 μg of protein homogenate to be tested (i.e., homogenate from cells expressing or not expressing an OR polypeptide, treated or not treated with carboxylic acid with or without a candidate modulator). Reaction mixtures are generally incubated at 37° C. for 6 minutes. Following incubation, reaction mixtures are deproteinized by the addition of 0.9 ml of cold 6% trichloroacetic acid. Tubes are centrifuged at 1800×g for 20 minutes and each supernatant solution is added to a Dowex AG50W-X4 column. The cAMP fraction from the column is eluted with 4 ml of 0.1 mM imidazole-HCl (pH 7.5) into a counting vial. Assays should be performed in triplicate. Control reactions should also be performed using protein homogenate from cells that do not express an OR polypeptide.

Assays should be performed using cells or extracts of cells expressing an OR, treated or not treated with a carboxylic acid with or without a candidate modulator. Control reactions should be performed using mock-transfected cells, or extracts from them in order to exclude possible non-specific effects of some candidate modulators According to the invention, adenylate cyclase activity is "changed" if it increases or decreases by 10% or more in a sample taken from cells treated with a candidate modulator of OR activity, relative to a similar sample of cells not treated with the candidate modulator or relative to a sample of cells not expressing an OR polypeptide (mock-transfected cells) but treated with the candidate modulator. Alternatively, a decrease of activity by 10% or more by the candidate modulator of OR polypeptides in a sample treated with a reference compound may be tested.

c. cAMP Assay:

Intracellular cAMP is measured using a cAMP radioimmunoassay (RIA) or cAMP binding protein according to methods widely known in the art. For example, Horton & Baxendale, 1995, Methods Mol. Biol. 41: 91-105, which is incorporated herein by reference, describes an RIA for cAMP.

A number of kits for the measurement of cAMP are commercially available, such as the High Efficiency Fluorescence Polarization-based homogeneous assay marketed by LJL Biosystems and NEN Life Science Products. Control reactions should be performed using extracts of mock-transfected cells to exclude possible non-specific effects of some candidate modulators.

Assays should be performed using cells or extracts of cells expressing an OR polypeptide, treated or not treated with a carboxylic acid with or without a candidate modulator. Control reactions should be performed using mock-transfected cells, or extracts from them in order to exclude possible non-specific effects of some candidate modulators The level of cAMP is "changed" if the level of cAMP detected in cells, expressing an OR polypeptide and treated with a candidate modulator of OR activity (or in extracts of such cells), using the RIA-based assay of Horton & Baxendale, 1995, supra, increases or decreases by at least 10% relative to the cAMP level in similar cells not treated with the candidate modulator.

d. Phospholipid Breakdown, DAG Production and Inositol Triphosphate Levels:

Receptors that activate the breakdown of phospholipids can be monitored for changes due to the activity of known or suspected modulators of an OR by monitoring phospholipid breakdown, and the resulting production of second messengers DAG and/or inositol triphosphate (IP3). Methods of measuring each of these are described in Phospholipid Signaling Protocols, edited by Ian M. Bird. Totowa, N.J., Humana Press, 1998, which is incorporated herein by reference. See also Rudolph et al., 1999, J. Biol. Chem. 274: 11824-11831, incorporated herein by reference, which also describes an assay for phosphatidylinositol breakdown. Assays should be performed using cells or extracts of cells expressing an OR, treated or not treated with carboxylic acid with or without a candidate modulator. Control reactions should be performed using mock-transfected cells, or extracts from them in order to exclude possible non-specific effects of some candidate modulators.

According to the invention, phosphatidylinositol breakdown, and diacylglycerol and/or inositol triphosphate levels are "changed" if they increase or decrease by at least 10% in a sample from cells expressing an OR polypeptide and treated with a candidate modulator in the presence or in the absence of carboxylic acid, relative to the level observed in a sample from cells expressing a carboxylic polypeptide that is not treated with the candidate modulator.

e. PKC Activation Assays:

Growth factor receptor tyrosine kinases tend to signal via a pathway involving activation of Protein Kinase C(PKC), which is a family of phospholipid- and calcium-activated protein kinases. PKC activation ultimately results in the transcription of an array of proto-oncogene transcription factor-encoding genes, including c-fos, c-myc and c-jun, proteases, protease inhibitors, including collagenase type I and plasminogen activator inhibitor, and adhesion molecules, including intracellular adhesion molecule I (ICAM I). Assays designed to detect increases in gene products induced by PKC can be used to monitor PKC activation and thereby receptor activity. In addition, activity of receptors that signal via PKC can be monitored through the use of reporter gene constructs driven by the control sequences of genes activated by PKC activation. This type of reporter gene-based assay is discussed in more detail below.

For a more direct measure of PKC activity, the method of Kikkawa et al., 1982, J. Biol. Chem. 257: 13341, incorporated herein by reference, can be used. This assay measures phosphorylation of a PKC substrate peptide, which is subsequently separated by binding to phosphocellulose paper. This PKC assay system can be used to measure activity of purified kinase, or the activity in crude cellular extracts. Protein kinase C sample can be diluted in 20 mM HEPES/2 mM DTT immediately prior to assay.

The substrate for the assay is the peptide Ac-FKKSFKL-NH2 (SEQ ID NO: 15), derived from the myristoylated alanine-rich protein kinase C substrate protein (MARCKS). The Km of the enzyme for this peptide is approximately 50 µM. Other basic, protein kinase C-selective peptides known in the art can also be used, at a concentration of at least 2-3 times their Km. Cofactors required for the assay include calcium, magnesium, ATP, phosphatidylserine and diacylglycerol. Depending upon the intent of the user, the assay can be performed to determine the amount of PKC present (activating conditions) or the amount of active PCK present (non-activating conditions). For most purposes according to the invention, non-activating conditions will be used, such that the PKC that is active in the sample when it is isolated is measured, rather than measuring the PKC that can be activated. For non-activating conditions, calcium is omitted in the assay in favor of EGTA.

The assay is performed in a mixture containing 20 mM HEPES, pH 7.4, 1-2 mM DTT, 5 mM MgCl2, 100 µM ATP, ~1 µCi γ-32P-ATP, 100 µg/ml peptide substrate (~100 µM), 140 µM/3.8 µM phosphatidylserine/diacylglycerol membranes, and 100 µM calcium (or most preferably 500 µM EGTA). 48 µl of sample, diluted in 20 mM HEPES, pH 7.4, 2 mM DTT is used in a final reaction volume of 80 µl. Reactions are performed at 30° C. for 5-10 minutes, followed by addition of 25 µl of a solution containing 100 mM ATP and 100 mM EDTA with a pH value of 8.0, which stops the reactions.

After the reaction is stopped, a portion (85 µl) of each reaction is spotted onto a Whatman P81 cellulose phosphate filter, followed by washes: four times 500 ml of 0.4% phosphoric acid, (5-10 min. per wash); and a final wash in 500 ml 95% EtOH, for 2-5 min. Bound radioactivity is measured by scintillation counting. Specific activity (cpm/nmol) of the labeled ATP is determined by spotting a sample of the reaction onto P81 paper and counting without washing. Units of PKC activity, defined as nmol phosphate transferred per min, are calculated as follows:

The activity, in UNITS (nmol/min) is: =_(cpm on paper)×(105 µl total/85 µl spotted)_(assay time, min)(specific activity of ATP cpm/nmol).

An alternative assay can be performed using a Protein Kinase C Assay Kit sold by PanVera (Cat. # P2747).

Assays are performed on extracts from cells expressing an OR polypeptide, treated or not treated with a carboxylic acid with or without a candidate modulator. Control reactions should be performed using mock-transfected cells, or extracts from them in order to exclude possible non-specific effects of some candidate modulators.

According to the invention, PKC activity is "changed" by a candidate modulator when the units of PKC measured by either assay described above increase or decrease by at least 10%, in extracts from cells expressing an OR and treated with a candidate modulator, relative to a reaction performed on a similar sample from cells not treated with a candidate modulator.

f. PKA Activation Assays

PKA activity can be assayed using any of several kits available commercially, for example from molecular device IMAP PKA assay kit, or from promega ProFluor PKA assay kit.

Assays should be performed using cells or extracts of cells expressing an OR, treated or not treated with a carboxylic acid with or without a candidate modulator. Control reactions should be performed using mock-transfected cells, or extracts from them in order to exclude possible non-specific effects of some candidate modulators PKA activity activity is "changed" if the level of activity is increased or decreased by 10% or more in a sample from cells, expressing an OR polypeptide, treated with a candidate modulator relative to PKA kinase activity in a sample from similar cells not treated with the candidate modulator.

g. Kinase Assays:

MAP kinase activity can be assayed using any of several kits available commercially, for example, the p38 MAP Kinase assay kit sold by New England Biolabs (Cat #9820) or the FlashPlate™ MAP Kinase assays sold by Perkin-Elmer Life Sciences.

Assays should be performed using cells or extracts of cells expressing an OR, treated or not treated with a carboxylic acid with or without a candidate modulator. Control reactions should be performed using mock-transfected cells, or extracts from them in order to exclude possible non-specific effects of some candidate modulators MAP Kinase activity is "changed" if the level of activity is increased or decreased by 10% or more in a sample from cells, expressing an OR polypeptide, treated with a candidate modulator relative to MAP kinase activity in a sample from similar cells not treated with the candidate modulator.

Direct assays for tyrosine kinase activity using known synthetic or natural tyrosine kinase substrates and labeled phosphate are well known, as are similar assays for other types of kinases (e.g., Ser/Thr kinases). Kinase assays can be performed with both purified kinases and crude extracts prepared from cells expressing an OR polypeptide, treated with or without a carboxylic acid, with or without a candidate modulator. Control reactions should be performed using mock-transfected cells, or extracts from them in order to exclude possible non-specific effects of some candidate modulators. Substrates can be either full length protein or synthetic peptides representing the substrate. Pinna & Ruzzene (1996, Biochem. Biophys. Acta 1314: 191-225, incorporated herein by reference) list a number of phosphorylation substrate sites useful for measuring kinase activities. A number of kinase substrate peptides are commercially available. One that is particularly useful is the "Src-related peptide," (RRLIEDAEYAARG (SEQ ID NO: 16); available from Sigma # A7433), which is a substrate for many receptor and nonreceptor tyrosine kinases. Because the assay described below requires binding of peptide substrates to filters, the peptide substrates should have a net positive charge to facilitate binding. Generally, peptide substrates should have at least 2 basic residues and a free amino terminus. Reactions generally use a peptide concentration of 0.7-1.5 mM.

Assays are generally carried out in a 25 µl volume comprising 5 µl of 5× kinase buffer (5 mg/mL BSA, 150 mM Tris-Cl (pH 7.5), 100 mM MgCl2; depending upon the exact kinase assayed for, MnCl2 can be used in place of or in addition to the MgCl2), 5 µl of 1.0 mM ATP (0.2 mM final concentration), gamma-32P-ATP (100-500 cpm/µmol), 3 µl of 10 mM peptide substrate (1.2 mM final concentration), cell extract containing kinase to be tested (cell extracts used for kinase assays should contain a phosphatase inhibitor (e.g. 0.1-1 mM sodium orthovanadate)), and H2O to 25 µl. Reactions are performed at 30° C., and are initiated by the addition of the cell extract.

Kinase reactions are performed for 30 seconds to about 30 minutes, followed by the addition of 45 µl of ice-cold 10% trichloroacetic acid (TCA). Samples are spun for 2 minutes in a microcentrifuge, and 35 µl of the supernatant is spotted onto Whatman P81 cellulose phosphate filter circles. The filters are washed three times with 500 ml cold 0.5% phosphoric acid, followed by one wash with 200 ml of acetone at room temperature for 5 minutes. Filters are dried and incorporated $^{32}P$ is measured by scintillation counting. The specific activity of ATP in the kinase reaction (e.g., in cpm/pmol) is determined by spotting a small sample (2-5 µl) of the reaction onto a P81 filter circle and counting directly, without washing. Counts per minute obtained in the kinase reaction (minus blank) are then divided by the specific activity to determine the moles of phosphate transferred in the reaction.

Assays should be performed using cells or extracts of cells expressing an OR, treated or not treated with a carboxylic acid with or without a candidate modulator. Control reactions should be performed using mock-transfected cells, or extracts from them in order to exclude possible non-specific effects of some candidate modulators.

Tyrosine kinase activity is "changed" if the level of kinase activity is increased or decreased by 10% or more in a sample from cells, expressing an OR polypeptide, treated with a candidate modulator relative to kinase activity in a sample from similar cells not treated with the candidate modulator.

h. Transcriptional Reporters for Downstream Pathway Activation:

The intracellular signal initiated by binding of a modulator to a receptor, e.g., an OR polypeptide of the invention, sets in motion a cascade of intracellular events, the ultimate consequence of which is a rapid and detectable change in the transcription and/or translation of one or more genes. The activity of the receptor can therefore be monitored by measuring the expression of a reporter gene driven by control sequences responsive to OR activation.

As used herein "promoter" refers to the transcriptional control elements necessary for receptor-mediated regulation of gene expression, including not only the basal promoter, but also any enhancers or transcription-factor binding sites necessary for receptor-regulated expression. By selecting promoters that are responsive to the intracellular signals resulting from agonist binding, and operatively linking the selected promoters to reporter genes whose transcription, translation or ultimate activity is readily detectable and measurable, the transcription based reporter assay provides a rapid indication of whether a given receptor is activated.

Reporter genes such as luciferase, Chloramphenicol Acetyl Transferase (CAT), Green Fluorescent Protein (GFP), beta-lactamase or beta-galactosidase are well known in the art, as are assays for the detection of their products.

Genes particularly well suited for monitoring receptor activity are the "immediate early" genes, which are rapidly induced, generally within minutes of contact between the receptor and the effector protein or ligand. The induction of immediate early gene transcription does not require the synthesis of new regulatory proteins. In addition to rapid responsiveness to ligand binding, characteristics of preferred genes useful to make reporter constructs include: low or undetectable expression in quiescent cells; induction that is transient and independent of new protein synthesis; subsequent shut-off of transcription requires new protein synthesis; and mRNAs transcribed from these genes have a short half-life. It is preferred, but not necessary that a transcriptional control element have all of these properties for it to be useful.

In order to assay OR activity with carboxylic acid-responsive transcriptional reporter construct, cells that stably express an OR polypeptide are stably transfected with the reporter construct. To screen for agonists, untreated cells are exposed to candidate modulators, or exposed to a carboxylic acid, and expression of the reporter is measured. The carboxylic acid-treated cultures serve as a standard for the level of transcription induced by a known agonist. An increase of at least 10% in reporter expression in the presence of a candidate modulator compared to reporter expression in the absence of any modulator indicates that the candidate is a modulator of OR activity. An agonist will induce at least as much, and preferably the same amount or more reporter expression than the carboxylic acid. Partial agonists may activate the receptor less compared to the carboxylic acid. This approach can also be used to screen for inverse agonists where cells express an OR polypeptide at levels such that there is an elevated basal activity of the reporter in the absence of carboxylic acid or other agonists. A decrease in reporter activity of 10% or more in the presence of a candidate modulator, relative to its absence, indicates that the compound is an inverse agonist.

To screen for antagonists, the cells expressing an OR and carrying the reporter construct are exposed to a carboxylic acid (or another agonist) in the presence and absence of a candidate modulator. A decrease of 10% or more in reporter expression in the presence of candidate modulator, relative to the absence of the candidate modulator, indicates that the candidate is an antagonist of OR activity.

Controls for transcription assays include cells not expressing an OR of the invention but carrying the reporter construct, as well as cells with a promoter less reporter construct. Compounds that are identified as modulators of OR-regulated transcription should also be analyzed to determine whether they affect transcription driven by other regulatory sequences and by other receptors, in order to determine the specificity and spectrum of their activity.

The transcriptional reporter assay, and most cell-based assays, are well suited for screening chemical libraries of chemical compounds for those that modulate OR activity. The libraries can be, for example, libraries from natural sources, e.g., plants, animals, bacteria, etc.

Candidate Modulators Useful According to the Invention

Candidate modulators can be screened from large libraries of synthetic or natural compounds. Numerous means are currently used for random and directed synthesis of various kinds of compounds. Synthetic compound libraries are commercially available from a number of companies including, for example, Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries of small organic molecules are available and can be prepared. Alternatively, libraries of natural compounds in the form of bacterial, fungal, plant and animal extracts are available from e.g., Pan Laboratories (Bothell, Wash.) or MycoSearch (NC), or are readily produceable by methods well known in the art. Additionally, natural and synthetically produced libraries and compounds are readily modified through conventional chemical, physical, and biochemical means.

EXAMPLES

The invention is further illustrated by the following non-limiting examples.

Experimental Procedure

Cell Culture and Cell Line Generation

Cells were maintained in minimal essential medium (EMEM, Lonza) containing 10% fetal bovine serum (M10). HEK293T-RTP1A1/RTP2 cells were generated by transfecting HEK293T with an expression vector containing the sequences of the chaperone proteins RTP1A1 and RTP2 and a resistance gene to puromycin, using Lipofectamine 2000. A recombinant cell population was selected by adding 10 µg/ml of puromycin into the culture medium. Monoclonal populations were further obtained by limit dilution procedure. Briefly, a cell suspension was diluted to contain 1 cell per ml and this dilution was dispatched in poly-D-lysine-coated 96 wells plates (200 µl of dilution per well). After 5 days of culture, the presence and number of cell colonies per well was checked under a phase contrast microscopic. After 5 additional days of culture, wells containing a single colony were harvested and each collected population was amplified independently.

Odorant Molecule Dilution

Odorant molecules were diluted at a concentration of 1 mole/liter (M) into dimethyl sulfoxide (DMSO) to generate stock solutions.

For screening experiments, stock solutions of odorant molecules were diluted in EMEM disposed in 96-well plates. Plates containing the tested molecules (1 molecule/well) at a concentration of 2 mM, at a concentration of 632 µM and at a concentration of 200 µM were prepared.

For concentration-response analysis, serial dilutions of the tested molecules were prepared from stock solutions in EMEM plated into 96-well plates.

Luciferase Assay.

For the initial deorphanisation screening and dose-response analysis, a Luciferase-based gene reporter assay (Promega, Leiden, The Nederlands) was used as described in Saito et al. (2004). Briefly, cells were platted on poly-D-lysine-coated 96-well plates (BD Bioscience, Erembodegem-Dorp, Belgium) and transfected with a plasmid containing the CRE-luciferase and a plasmid containing the olfactory receptor. Sixteen hours after transfection, the culture medium was replaced by serum-free EMEM containing the tested ligand at a determined concentration. After four hours of incubation at 37° C. degree, cells were lysed and processed for luminescence measurement according to the manufacturer's protocols. Luminescene emission was recorded on a Spectra Max M5 reader (Molecular Devices, Sunnyvale, Calif.). Results were expressed as percentage of the response induced by 10 µM of the adenylate cyclase activator Forskolin.

Example 1

Screening of Odorant Molecule Libraries

Odorant molecule libraries containing carboxylic acids and other types of molecules were used to identify activators of the seven ORs of the invention. The deorphanisation campaign was performed on the seven olfactory receptors with a series of 148 odorant molecules. Sixteen carboxylic acids present in sweat were included within the 148 tested odorants. Black squares correspond to a response of a receptor to one odorant molecule. The part of the table corresponding to carboxylic acids has been boxed in bold. The seven tested class 1 receptors have all responded specifically and exclusively to carboxylic acids.

Each molecule was tested at 3 different concentrations (1 mM, 316 µM, 100 µM). The different molecules of the tested libraries were disposed at the same concentration into 96 well plates (1 well/molecule) containing cells expressing the receptor of interest. The activity of the tested molecules was measured using the luciferase activity as explained above. The median luciferase activity induced by the tested molecules and the associated standard deviation were determined. Putatively active molecules (hits) were defined as molecules inducing a luciferase activity higher or equal to the median+2 standard deviations.

Table 2 summarizes the results of this deorphanization. Each OR-activating molecule couple is indicated by a black square at the intersection of the column corresponding to the receptor and the row corresponding to the molecule. The results clearly show that the seven ORs of the invention are activated by carboxylic acids which are present in human sweat.

The 7 ORs of the invention were further included in a large screening campaign aiming to test different molecule libraries that do not contain carboxylic acids. These screenings were performed as described above. A total of 823 molecules were tested on OR52L1, OR52E8, OR51I2, OR52A5 and OR56A6. A total of 592 molecules were tested on OR52B2 and a total of 777 were tested on OR52E1. The complete list of the tested molecules is given in Table 3. None of the molecules gave a hit on any of the 7 ORs of the invention. This result confirms the very high selectivity of the 7 ORs of the invention to carboxylic acid ligands.

The 7 tested ORs from class 1, (corresponding to the ORs of the invention, namely: OR52L1, OR52E8, OR52B2, OR51I2, OR52E1, OR52A5 and OR56A5) were therefore found to respond specifically and exclusively to carboxylic acids.

Example 2

Dose-Response Analysis of Ligand-OR Interaction

The hits were validated by concentration-response analysis. Semi-logarithmic serial dilutions of hit molecules, from 1 mM to 316 nM, were tested on the responding ORs using the luciferase assay as described above.

Results are given in Table 2. Full results are given in FIG. 2A-FIG. 2J.

We observed that each of the 7 ORs tested respond to at least one molecule containing a carboxylic function. A careful comparison of these activators with the known carboxylic acids occurring in human sweat revealed that each of the receptors responds to at least one carboxylic acid released in sweat. Some of these acids, such as hexanoic acid, 3-methylhexanoic acid, (E)-3-methyl-2-hexenoic acid, 3-hydroxy-3-methylhexanoic acid, heptanoic acid, octanoic acid, 4-ethyloctanoic acid, (Zeng et al. 1991; J. Chem. Ecolog. Vol. 17 pp 1469-1492; Natsch et al. 2006 Chem. & Biodiv. Vol. 3 pp 1-20) are known to be important promoters of human sweat malodor.

These 7 ORs of the invention are therefore involved in the perception of sweat malodor elicited by carboxylic acids and constitute valuable candidate receptors for the identification of antagonists and/or blockers that would block the perception of malodor.

TABLE 2

Activation of ORs according to the invention by carboxylic acids originating from sweat.

| | OR52L1 | OR52E8 | OR52B2 | OR51I2 | OR52E1 | OR52A5 | OR56A5 |
|---|---|---|---|---|---|---|---|
| butanoic acid | | | | ■ | ■ | | |
| Isovaleric acid | ■ | | | ■ | | | |
| pentanoic acid | ■ | | | ■ | | | |
| hexanoic acid | | | ■ | ■ | | | ■ |
| 2-methylhexanoic acid | | | | ■ | | | |
| 3-methylhexanoic acid | | | | ■ | | | |
| (E)-3-methyl-2-hexenoic acid | | | | ■ | | | |
| 3-hydroxy-3-methylhexanoic acid | | ■ | | | | | |
| heptanoic acid | | | ■ | | | | ■ |
| 2-methylheptanoic acid | | | ■ | | | | |
| octanoic acid | | | ■ | | | | ■ |
| 4-ethyloctanoic acid | | | | | | ■ | ■ |
| nonanoic acid | | | ■ | | | | ■ |
| decanoic acid | | | ■ | | | | ■ |
| undecanoic acid | | | ■ | | | | ■ |
| benzoic acid | | | | ■ | | | |
| (R)-(+)-Citronellal | | | | | | | |
| (R)-(+)-Pulegone | | | | | | | |
| (S)-(-)-Citronellol | | | | | | | |
| 1,4-Butanedithiol | | | | | | | |
| 1-amino-2-phenylethane | | | | | | | |
| 1-Butaneethiol | | | | | | | |
| 1-cyclohexylethanol | | | | | | | |
| 1-Furfurylpyrrole | | | | | | | |
| 1-hepten-3-ol | | | | | | | |
| 1-Propanol | | | | | | | |
| 2,6-Dimethylthiophenol | | | | | | | |
| 2-Butanone | | | | | | | |
| 2-cyclohexylethanol | | | | | | | |
| 2-Methylbutyl acetate | | | | | | | |
| 2-Methylpyridine | | | | | | | |
| 2-Nonanone | | | | | | | |
| 3,4-Dimethoxyphenyl acetone | | | | | | | |
| 3-Octanone | | | | | | | |
| 4-(4-Methoxyphenyl)-2-butanone | | | | | | | |
| 4-(methylthio)butanol | | | | | | | |
| -Hydroxy-3-methoxyphenylacetone | | | | | | | |
| 4-Hydroxybenzaldehyde | | | | | | | |
| 4-Propylphenol | | | | | | | |
| 5-Hexen-1-ol | | | | | | | |
| Acetophenone | | | | | | | |
| a-ionone | | | | | | | |
| Allyl cyclohexylpropionate | | | | | | | |
| Allyl mercaptan | | | | | | | |
| Allyl sulfide | | | | | | | |
| alpha-Methylbenzyl alcohol | | | | | | | |
| AMYL BENZOATE | | | | | | | |
| Amyl salicylate | | | | | | | |
| Androstanolone | | | | | | | |
| Anisyl acetate | | | | | | | |

TABLE 2-continued

Activation of ORs according to the invention by carboxylic acids originating from sweat.

| |  |  |  |  |  |  |  |
|---|---|---|---|---|---|---|---|
| a-pinene | | | | | | | |
| a-terpineol | | | | | | | |
| Benzophenone | | | | | | | |
| Benzyl acetate | | | | | | | |
| Benzyl mercaptan | | | | | | | |
| Butyraldehyde | | | | | | | |
| Carvacrol | | | | | | | |
| Caryophyllene | | | | | | | |
| Cinnamyl acetate | | | | | | | |
| cis-6-Nonenal | | | | | | | |
| CITRAL DIMETHYL ACETAL | | | | | | | |
| Coumarin | | | | | | | |
| Cyclamal | | | | | | | |
| Cyclopentadecanone | | | | | | | |
| D-Carvone | | | | | | | |
| DECALACTONE DELTA | | | | | | | |
| DECYL ACETATE | | | | | | | |
| dihexyl fumarate | | | | | | | |
| Dihydroanethole | | | | | | | |
| Dihydroeugenol | | | | | | | |
| Dimethyl sulfide | | | | | | | |
| DIONE | | | | | | | |
| Ethyl 2-mercaptopropionate | | | | | | | |
| Ethyl p-anisate | | | | | | | |
| Ethyl phenylacetate | | | | | | | |
| Ethylvanillin | | | | | | | |
| Eucalyptol | | | | | | | |
| floridile | | | | | | | |
| Frutonile | | | | | | | |
| Furfuryl butyrate | | | | | | | |
| FurFuryl methyl sulfide | | | | | | | |
| Gamma-jasmolactone | | | | | | | |
| gamma-undcalactone | | | | | | | |
| Geranyl acetate | | | | | | | |
| Guaiacol | | | | | | | |
| Heptaldehyde | | | | | | | |
| Hexanal | | | | | | | |
| Hexyl octanoate | | | | | | | |
| Isoanyl laurate | | | | | | | |
| Isobornylcyclohexanol | | | | | | | |
| Jasmacyclene | | | | | | | |
| Jasmatone | | | | | | | |
| JASMOLACTONE | | | | | | | |
| Jessate | | | | | | | |
| Lauryl alcohol | | | | | | | |
| L-Nicotine | | | | | | | |
| Lyral | | | | | | | |
| Menthalactone | | | | | | | |
| Menthol | | | | | | | |
| Methyl 3-nonenoate | | | | | | | |
| Methyl anthranilate | | | | | | | |
| METHYL HEPTENONE PURE | | | | | | | |
| Methyl Laitone | | | | | | | |
| methyl salicylate | | | | | | | |
| Nectaryl | | | | | | | |
| NONADIENOL-2,6 | | | | | | | |

TABLE 2-continued

Activation of ORs according to the invention by carboxylic acids originating from sweat.

| | | | | | | | |
|---|---|---|---|---|---|---|---|
| Nonanal | | | | | | | |
| Nonyl Alcohol | | | | | | | |
| n-Valeraldehyde | | | | | | | |
| Ocimene | | | | | | | |
| o-cresol | | | | | | | |
| Octanal | | | | | | | |
| Octyl propionate | | | | | | | |
| OXYOCTALINE FORMATE | | | | | | | |
| Para-methoxyacetophenone | | | | | | | |
| p-cresyl methyl ether | | | | | | | |
| p-Dimethoxybenzene | | | | | | | |
| Phenethyl 2-furoate | | | | | | | |
| Phenyl acetate | | | | | | | |
| Phenylethanol | | | | | | | |
| Piperonyl acetate | | | | | | | |
| Piperonyl isobutyrate | | | | | | | |
| p-Mentha-8-thiol-3-one | | | | | | | |
| PRENYL BENZOATE | | | | | | | |
| Propenylguaethol | | | | | | | |
| PROPYLIDENE PHTHALIDE | | | | | | | |
| Pyrrole | | | | | | | |
| Raspberry ketone | | | | | | | |
| rossitol | | | | | | | |
| stemone | | | | | | | |
| Terpinen-4-ol | | | | | | | |
| Tetrahydrogeraniol | | | | | | | |
| Tetrahydromyrcenol | | | | | | | |
| Thymol | | | | | | | |
| tridecenenitrile | | | | | | | |
| undecanal | | | | | | | |
| UNDECATRIENE | | | | | | | |
| Undecavertol | | | | | | | |
| Undecene-2-nitrile | | | | | | | |
| Vanillin | | | | | | | |
| Verdyl propionate | | | | | | | |
| Vetiveryl Acetate | | | | | | | |

TABLE 3

Complete list of odorant molecules tested on the 7 ORs of the invention.

gamma Dodecalactone (natural)
Hexyl isobutyrate
3-Acetyl-2,5-dimethylthiophene
Acetaldehyde ethyl phenylethyl acetal
Methyl isoeugenol
4-Isopropylcyclohexanol
Ethyl maltol
Prenyl benzoate
2-Methyl-3-(p-methoxyphenyl)propanal
(+)-Camphene
Ethyl acetoacetate ethylene glycol ketal
Acetanisole
4,5-Dihydro-3(2H)thiophenone
Styrene
Benzyl alcohol
Benzaldehyde
Benzyl mercaptan
2-Ethylpyridine
alpha,alpha-Dimethylphenethyl alcohol
Dimethyl benzyl carbinyl butyrate
alpha-Methylcinnamaldehyde
Methyl phenylacetate
Phenylacetaldehyde dimethyl acetal
Diphenyl ether
alpha-Amylcinnamyl alcohol
alpha-Hexylcinnamaldehyde
p-Tolyl phenylacetate
Isobutyl phenylacetate
Benzyl phenylacetate
Anisyl phenylacetate
Triacetin
2-Methyl-4-phenyl-2-butanol
Methyl cinnamate
Benzyl isobutyrate
Ethyl cinnamate
Benzyl butyrate
Benzyl cinnamate
Phenethyl acetate
Benzyl ether
Phenethyl cinnamate
Cinnamyl acetate
2-Phenoxyethyl isobutyrate
1-Bromo-2-phenylethylene
2,2-Dimethyl-3-(3-methylphenyl)propanol
2-Methyl-3-(p-isopropylphenyl)propionaldehyde
p-Tolylacetaldehyde
1-Phenyl-3-methyl-3-pentanol
Anisyl acetate
p-Propyl anisole
gamma-Octalactone
Cinnamic alcohol
Cinnamaldehyde
gamma-Nonalactone
2-Cyclohexyliden-2-phenylacetonitrile TABLE 3-continued Complete list of odorant molecules tested on the 7 ORs of the invention.

Phenethyl formate
gamma-Undecalactone
(−)-α-Terpineol
4-Methylanisole
Ethyl 6-acetoxyhexanoate
Anisyl alcohol
3-Decen-2-one
gamma-Heptalactone
Ethyl propionate
Diethyl malonate
Ethyl butyrate
Acetal
Geranyl acetate
Ethylene brassylate
omega-Pentadecalactone
Butyl laurate
3,7-Dimethyl-1-octanol
Citronellol
(±)-Citronellal
Geraniol
Nerol
Isoamyl butyrate
Ethyl heptanoate
Ethyl octanoate
p-Cresol
Dimethyl succinate
2,6-Dimethyl-5-heptenal
1-Propanethiol
Hydroxycitronellal
Isopentylamine
Ethyl isovalerate
Benzenethiol
3-Methylpyridine
2-Methylpyridine
2-Methylpyrazine
Octyl isobutyrate
1,16-Hexadecalactone
Butyl 10-undecenoate
Butylamine
1-Butanethiol
1,3-Propanedithiol
Pyrrole
Isopropyl myristate
Diethyl sebacate
Methyl decanoate
2-Heptanone
Isoamyl formate
n-Valeraldehyde
Pyridine
Piperidine
6-Methyl-5-hepten-2-one
Methyl 2-octynoate
Hexylamine
Hexyl alcohol
Ethyl octadecanoate
Heptaldehyde
Hexyl octanoate
Methyl 2-nonenoate
Methyl 2-nonynoate
Methyl 10-undecenoate
Methyl laurate
Myrcenyl acetate
2-Undecanone
Octyl acetate
Decyl acetate
2-Acetylpyridine
Decanal
10-Undecen-1-ol
Undecanal
10-Undecenal
Dodecyl aldehyde
Methyl stearate
Methyl linoleate
Dihydrojasmone
Linalyl acetate
Linalyl formate
(2,6,6-Trimethylcyclohexa-1,3-dienyl)methanal
2(2,4-Dimethylcyclohex-3-en-1-yl)-5-methyl-5-(1-methylpropy-)

TABLE 3-continued

Complete list of odorant molecules tested on the 7 ORs of the invention.

Benzyl salicylate
Maltol
2,6-Dimethylthiophenol
1,4-Butanedithiol
Prenyl acetate
1,8-Octanedithiol
2-Furyl methyl ketone
Methyl salicylate
2-Acetyl-5-methylfuran
Fenchone
Benzophenone
Styrallyl propionate
Isobutyl benzoate
Benzyl benzoate
Heliotropin
Indole
Ethyl vanillin
Vanillin
Ammonium sulfide
Ethyl 3-phenylglycidate
Triethylamine
Methyl p-anisate
4'-Methylacetophenone
Cuminaldehyde
1,3,4,6,7,8-Hexahydro-4,6,6,7,8,8-hexamethylcyclopenta[g]-2-benzopyran Solution
alpha-Amylcinnamaldehyde
Benzyl propionate
Cinnamyl cinnamate
3-Phenylpropyl acetate
Phenylacetaldehyde
3-Phenyl-1-propanol
Phenoxyethanol
4-Ethylphenol
4-Hydroxybenzaldehyde
p-Anisaldehyde
4-Heptanone
Ethyl nonanoate
2,5-Dimethylpyrazine
Myrcene
Propionaldehyde
Isoamyl alcohol
Ethyl hexanoate
Allyl hexanoate
Pyrrolidine
Butyl acetate
Isoamyl acetate
Ethyl myristate
Isobornyl acetate
alpha-Ionone
3 methyl 4 (2,6,6 trimethyl 2 cyclohex-1-yl-3 buten 2 one)/alpha-isomethyl ionone
Butylated hydroxytoluene
9-Decen-1-ol
2-Hexylcyclopentanone
2,4,-Dimethyl-2-(1,1,4,4-tetramethyltetralinyl)-1,3-dioxolan
2,6-Dimethyl-2-heptanol
Menthalactone
Amyl 2-furoate
Methyl anthranilate
Guaicwood acetate
3-Carene
Methyl 3-nonenoate
3,5-Dimethyl-1,2-cyclopentadione
Syringaldehyde
Methyl 3-(methylthio)propionate
6-Isopropylquinoline
Furfuryl 3-methylbutanoate
2-n-Heptylcyclopentanone
Cuminyl nitrile
cis-4-(1-Methylethyl)cyclohexanemethanol
1,3,3-Trimethyl-2-norbornanyl acetate
3,7-Dimethyl-1,3,6-octatriene
d,l-Limonene
2-t-Butylcyclohexyloxy-2-butanol
Benzyl acetate
Phenethyl isovalerate
p-Methylphenyl acetate

TABLE 3-continued

Complete list of odorant molecules tested on the 7 ORs of the invention.

4-Allylanisole
(−)-Menthone
Ethyl acrylate
2,6,10-Trimethyl-9-undecenal
Citronellyl propionate
Hydroxycitronellal dimethyl acetal
Ethyl acetoacetate
Allyl heptanoate
Octyl propionate
Hexyl acetate
Nonyl alcohol
Nonyl acetate
Furfuryl methyl sulfide
1-Furfurylpyrrole
Methyl 2,5,10-trimethyl-2,5,9-cyclododecatrien-1-yl ketone
Linalyl propionate
2-sec-Butylcyclohexanone
beta-Ionone
7-Acetyl-1,1,3,4,4,6-hexamethyltetralin
p-Dimethoxybenzene
Citronellyl acetate
alpha,alpha-Dimethylphenethyl acetate
2-Ethyl-3-methylpyrazine
(1R)-(+)-Fenchyl alcohol
1,3,5-Undecatriene
Tetrahydro-4-methyl-2-(2-methyl-1-propenyl)-(2H)pyran
cis-3-Hexenyl butyrate
4-tert-Amylcyclohexanone
1,1-Diethoxycyclohexane
Hexyl tiglate
Dihydro-beta-ionone
Methyl undecanoate
3-Propylidenephthalide
Tricyclodecenyl propionate
Methyl trans-cinnamate
1,8,12-Bisabolatriene
Bourgeonal
(1S)-(−)-β-Pinene
Androstenone
trans-3-Octen-2-one
1,2-Dihydrolinalool
Tetrahydromyrcenol
2,6-Dimethyl-7-octen-2-ol
2-Isobutylthiazole
beta-Farnesene
trans-2-Heptenal
3-Pentyltetrahydro[2H]pyranyl acetate
Hexyl trans-2-butenoate
Dihexyl fumarate
1,10-Dimethyl-9-decalol
Ethyl 2-mercaptopropionate
Cedryl methyl ether
4 Methyl-4-mercaptopentan-2-one
Isoamyl octanoate
trans-2-Dodecen-1-al
Isoamyl benzoate (natural)
Amyl salicylate
Butyl levulinate
4-(Methylthio)butanol
Vanillin isobutyrate
Citronellyl 3-methylbut-2-enoate
Tetrahydrolavandulyl acetate
2-Pentanethiol
cis-4-Decenal
Cyclohexaneethyl acetate
Methyl 2-methylpentanoate
Methyl propyl disulfide
5-Methyl-2-phenyl-2-hexenal
2-Acetylpyrazine
(−)-Menthol
D-Carvone
5-Methyl-3-heptanone oxime
2-Tridecenonitrile
Nerolidyl acetate
Geranyl isobutyrate
Damascenone
b-Damascone
(5H)-5-Methyl-6,7-dihydrocyclopenta(b)pyrazine

TABLE 3-continued

Complete list of odorant molecules tested on the 7 ORs of the invention.

2,3 or 10-Mercaptopinane
Ethyl 3-hexenoate
2,6,10-Trimethylundeca-5,9-dienal
2-Methoxy-3-(1-methylpropyl)pyrazine
1,3-Butanedithiol
2-Heptyltetrahydrofuran
Dodecane nitrile
Hexyl propionate
2-Methylbutyl isovalerate
2-Isobutyl-3-methoxypyrazine
3,7-Dimethyl-6-octenyl 2-methylcrotonate
alpha-Damascone
Phenethyl 2-methylbutyrate
Methyl dihydrojasmonate
4-Hexen-3-one
Ethyl 2-cyclohexylpropionate
trans,trans-2,4-Decadienal
cis-3-Hexenyl benzoate
a,3,3-Trimethylcyclohexylmethyl formate
Dihydromyrcenyl formate
Diacetin
2,5-Dimethyl-2-octen-6-one
4-Phenylbutane-2-one
Hexyl butyrate
4-Methyl-2-phenyl-2-pentenal
Allyl cyclohexanepropionate
2-Methoxy-4-propylphenol
trans-2,cis-6-Nonadien-1-ol
Acetaldehyde ethyl (Z)-3-hexenyl acetal
2-Methyl-4-(2,2,3-trimethyl-3-cyclopenten-1-yl)but-2-en-1-ol
2-Ethyl-4-(2,2,3-trimethyl-3-cyclopenten-1-yl)-2-buten-1-ol
2-Methoxy-3-methylpyrazine
2-Methyl-3-furanthiol
4,5-Dimethyl-3-hydroxy-2,5-dihydrofuran-2-one
Thiazole
Watermelon ketone
Ethyl 2-hexylacetoacetate
Hexahydro-1,1,5,5-tetramethyl[2H]-2,4a-methanonaphthalen-8[5H]one
Phenylacetaldehyde glyceryl acetal
2-Acetyl-2-thiazoline
4(Octahydro-4,7-methano[5H]inden-5-ylidene)butanal
Ethyl 2-trans-4-cis-decadienoate
2-Methoxypyrazine
4-(4-Hydroxy-4-Methylpentyl)-3-cyclohexene-1-carboxaldehyde
4-t-Butylcyclohexyl acetate
Acetylcedrene
6,10-Dimethyl-5,9-undecadien-2-yl acetat (cis & trans)
3-(Methylthio)propionaldehyde
6-(3-Pentenyl)tetrahydro[2H]pyran-2-one
delta-Nonalactone
(Z)-3-Hexenylpropionate
Dihydro-4-methyl-5-pentylfuran-2(3H)one
6,7-Dihydro-1,1,2,3,3-pentamethyl-4(5H)indanone
6,6-Dimethyl-2-norpinenepropionaldehyde
1-Octen-3-ol
4-(Methylthio)-2-butanone
6-Isopropyl-2[1H]octahydronaphthalenone
5,6,7,8-Tetrahydroquinoxaline
3,5,5-Trimethyl-1-hexanol
1,9-Nonanedithiol
Ethyl dehydrocyclogeranate
2-Isopropyl-5-methyl-2-hexenal
Methyl phenethyl ether
3,3,5,5-Tetramethyl-4-(1-ethoxyethenyl)cyclohexanone
2,5-Dimethyl-4-hydroxy-3(2H)-furanone Solution
cis-3-Hexen-1-yl acetate
trans-3-Hexenyl acetate
1-Vinyl-2-(1-methylpropyl)cyclohexyl acetate
Dodecahydrotetramethylnaphthofuran
5-Cyclohexadecen-1-one
Isohexenyltetrahydrobenzaldehyde
2-Heptylfuran
(E)-6,10-Dimethylundeca-5,9-dien-2-one
2,4-Dimethyl-5-acetylthiazole
5-Methyl-3-butyltetrahydropyran-4-yl acetate
p-Mentha-8-thiol-3-one
Methyl (p-tolyloxy)acetate
3-Propylbicyclo-(2.2.1)hept-5-en-2-carboxaldehyde

TABLE 3-continued

Complete list of odorant molecules tested on the 7 ORs of the invention.

Octyl 2-furoate
alpha-Furfuryl octanoate
Ethyl 2-methylpentanoate
Furfuryl heptanoate
9-Decenal
3,7-Dimethyl octanenitrile
trans-Nerolidol
2,5-Dimethyl-4-methoxy-3(2H)furanone
Acetaldehyde ethyl linalyl acetal
(Z)-3-Hexenyl isobutyrate
Octahydro-7-methyl-1,4-methanonaphthalen-6-[2H]-one
Anethol
3,7-Dimethyl-7-methoxyoctan-2-ol
Diisopropyl disulfide
p-Menthane-3,8-diol
Diacetyl
2-Ethylhexanal ethylene glycol acetal
Cinnamyl nitrile
2-Phenyl-2-butenal
Octahydrocoumarin
2,2'-(Dithiodimethylene)difuran
3,4-Hexanedione
Farnesol
NOOTKATONE
d-Fenchone
ALPHA CEDRENE ((−)-a-Cedrene;1S,2R,5S)-2,6,6,8-
Tetramethyltricyclo[5.3.1.01.5]undec-8-ene)
1,4-Cineole
Methyl atrarate
Eucalyptol
2-Pentylcyclopentanone
cis-Jasmone
Acetovanillone
Dihydro-alpha-terpineol
Cyclopentadecanone
1,4-Dithiane
Borneol
n-Amyl phenylacetate
Acetoin
3,7-Dimethyl-2,6-octadienenitrile
l-Citronellyl nitrile
3-(Methylthio)-1-hexanol
2,4,6-Trimethyl-4-phenyl-1,3-dioxane
Ethyl (±)-2-hydroxycaproate
Methyl 3,3-dimethylbicyclo[2.2.1]heptan-3-carboxylate
Phenylethyl n-butyl ether
trans-2-Undecenal
4-Isopropylbenzyl alcohol
3-Ethylpyridine
Methyl benzyl ether
Ethyl valerate
Amyl hexanoate
Isobutyl propionate
Ethyl 3-hydroxybutyrate
Tricyclodecenyl acetate
3-Methyl-1-cyclopentadecanone
Hexyl phenylacetate
2-Acetyl-3,5(6)-dimethylpyrazine
3,5,5-Trimethylhexanal
Octahydro-2,3,8,8-tetramethyl-2-acetonaphthone
2-Butyl-4,4,6-trimethyl-1,3-dioxane
Thujone
4-(4-Hydroxyphenyl)-2-butanone
Ethylene dodecanedioate
3-Methyl-5-phenyl-1-pentanol
3-Methyl-5-phenyl-1-pentanal
3-Butylidenephthalide
2-Coumaranone
Methyl isovalerate
3-Methyl-2-buten-1-ol
2,6-Nonadienal (trans, cis)
Phenylethyl isoamyl ether
4-Carvomenthenol
Caryophyllene acetate
2-Methyl-3-tetrahydrofuranthiol
delta-Damascone
2,6-Xylenol
1-Phenyl-1,2-propanedione
Ethyl 2-ethyl-6,6-dimethyl-2-cyclohexenecarboxylate
Ethyl tiglate
3,5,5-Trimethylhexyl acetate
Formaldehyde cyclododecyl ethyl acetal
Terpinolene
D-(+)-Xylose
Isobutyl 2-butenoate
3-Heptanol
Menthanyl acetate
Acetoxymethyl-isolongifolene
2,3-Dimethylpyrazine
Ethyl 2-methyl-6-pentyl-4-oxocyclohex-2-enecarboxylate
Butyl formate
Allyl sulfide
Tetrahydrogeranial
d-Limonene
2,3-Pentanedione
Tributyrin
Phenethyl alcohol
2-Pentyl butyrate
Methyl 2-furoate
cis-3-Hexenyl cis-3-hexenoate
L-Menthyl lactate
Isobutyl tiglate
Ethyl pyruvate
3,7-Dimethyl-2,6-nonadienenitrile
Dihydrocarveol
Cyclohexyl acetate
Furfuryl acetate
Furfuryl butyrate
Methyl butyrate
Ethyl trans-2-butenoate
2-Methylbutyl acetate
6-Methylheptan-3-one
Ethyl methyl sulfide
Dimethyl disulfide
3-Penten-2-one
Hexyl salicylate
Diethyl malate
Propyl hexanoate
Ethyl undecanoate
Ethyl palmitate
Butyl 2-methylvalerate
Isoamyl laurate
2-Isobutyl-4-hydroxy-4-methyltetrahydropyran
Isopropyl butyrate
Amyl octanoate
Phenethylamine
Propyl isobutyrate
4-Propylphenol
L-Carvone
5-(2,2,3-Trimethylcyclopent-3-en-1-yl)-3-methylpentan-2-ol
trans-4-Decenal
2,5,9,10-Tetramethyl-5,6-dehydro-1-decalyl formate
Maltol isobutyrate
2,2,5-Trimethyl-5-pentylcyclopentanone
4-Methyl-5-thiazoleethanol acetate
Isoamyl isovalerate
Methyl tiglate
Hexanal
4-Allyl-2,6-dimethoxyphenol
Isopropyl 2-methylbutyrate
p-lsobutyl-alpha-methylhydrocinnamaldehyde
trans-2-Hexen-1-al
4-Heptenal
3,5,5-Trimethylhexyl formate
3,3,5-Trimethylcyclohexylethylether
Isopropyl alcohol
cis-3-Hexenyl methyl carbonate
Allyl amylglycolate
para-Ethyl-alpha,alpha-dimethyldihydrocinnamaldehyde
Hydratropaldehyde propylene glycol acetal
Phenethyl pivalate
1,1-Dimethoxy-2,2,5-trimethyl-4-hexene
Methyl sulfoxide
Ethyl-2-t-butylcyclohexylcarbonate
7-Formyl-5-isopropyl-2-methylbicyclo[2,2,2]oct-2-ene
Amylcyclohexyl acetate (mixed isomers)

TABLE 3-continued

Complete list of odorant molecules tested on the 7 ORs of the invention.

cis-3-Hexenyl tiglate
Hexyl benzoate
(−)-Ambroxide
Isolongifolene epoxide
Phenylethyl isopropyl ether
4-Methyl-4-phenyl-2-pentyl acetate
Grisalva
2-Ethoxy-9-methylene-2,6,6-trimethylbicyclo[3.3.1.]nonane
Methyl 1-methyl-4-isopropylbicyclo[2.2.2]oct-5-enecarboxylate
Methyl sorbate
Cyclomugual
2-Methyldecanonitrile
6- or 7-Ethylideneoctahydro-5,8-methano[2H]-1-benzopyran-2-one
5-Ethyl-3-hydroxy-4-methyl-2(5H)furanone
delta-Decalactone
gamma-Decalactone
1-(2,2,6-Trimethylcyclohexyl)-3-hexanol
2-methoxyphenol reaction products with hydrogenated 2,2-dimethyl-3-methylenebicyclo[2.2.1]heptane
delta-Undecalactone
1-p-Menthene-8-thiol
1-Propanol
delta-Dodecalactone
Phenethyl 2-furoate
2,5,5-Trimethyloctahydro-2-naphthol
2-Methyl-4-(2,6,6-trimethyl-2-cyclohexenyl)butanal
Methyl trans-2-octenoate
2,2,6-Trimethyl-6-vinyltetrahydropyran
2,2-Dimethyl-5-(1-methylpropen-1-yl)tetrahydrofuran
Ethyl 2-methylbutyrate
Citronellyloxyacetaldehyde
Butyl butyryllactate
Acetaldehyde phenethyl propyl acetal
Allyl phenoxyacetate
Ethylamine
Acetaldehyde
Ethanethiol
1,5-Dimethyl bicyclo(3.2.1)octan-8-one oxime
Dimethyl sulfide
Citral dimethyl acetal
(±)-Camphor
Cedarwood oil alcohols
Cedryl acetate
Terpinyl isobutyrate
3-Methyl-3-pentanol
ω-6-Hexadecenlactone
Isoamyl cinnamate
Isobutyl acetoacetate
Isobutyl benzyl carbinol
Ethyl 3-methyl-3-phenylglycidate
(1S)-(−)-α-Pinene
L-Fenchone
Triethyl citrate
Linalyl isobutyrate
Linalyl cinnamate
Linalool
Isobutylamine
Isobutyl alcohol
Isobutyraldehyde
2-Butanol
2-Butanone
Pyruvaldehyde
Methyl acetate
alpha-Irone
Allyl alpha-ionone
Geranium bourbon
1,3-Dimethylbut-3-enyl isobutyrate
Cognac oil, green
alpha-Terpinyl acetate
p-tert-Butyl-alpha-methyldihydrocinnamic aldehyde
alpha-Pinene
Ethyl octahydro-4,7-methano[3aH]indene-3a-carboxylate
Musk ketone
Musk xylol
4-Methyl-3-decen-5-ol
2,4,4,7-Tetramethyl-6,8-nonadien-3-one oxime
Acetyl diisoamylene
3,5,6,6-Tetramethyl-4-methylene-2-heptanol TABLE 3-continued Complete list of odorant molecules tested on the 7 ORs of the invention.

2-Nonanone
2,4-Dimethyl-4-phenyltetrahydrofuran
Skatole
N-Methyl-N-phenyl-2-methylbutyramide
Diethyl phthalate
3-Methyldodecanonitrile
Isobornyl isobutyrate
2-Methoxybiphenyl
Methyl 2-methylbutyrate
Allyl mercaptan
Isoamyl salicylate
Caryophyllene
p-Methoxybenzonitrile
Tetrahydrolinalool
Diethyl L-tartrate
o-t-Butylcyclohexyl acetate
2-Isopropylphenol
Isopulegyl acetate
(−)-Isopulegol
Menthone
Thymol
Salicylaldehyde
1-Methylnaphthalene
Trichloromethyl phenyl carbinyl acetate
2-Methylpentyl 2-methylpentanoate
2-Phenylpropionaldehyde dimethyl acetal
Naphthalene
2-Naphthalenethiol
Coumarin
trans-Isoeugenyl benzyl ether
trans-2-Hexen-1-ol
cis-3-Hexen-1-ol
Methyl beta-naphthyl ketone
4-Allyl-1,2-dimethoxybenzene
beta-Naphthyl ethyl ether
2-Phenylpropionaldehyde
Methyl benzoate
Methyl nicotinate
Ethyl benzoate
alpha-Methylbenzyl acetate
1-Ethylhexyl tiglate
Ethyl p-anisate
Isoamyl benzoate
Geranyl benzoate
Piperine
Propenylguaethol
2-Hexyl-2-cyclopenten-1-one
o-Cresol
2,5-Xylenol
2-(2-(4-Methyl-3-cyclohexen-1-yl)propyl)cyclopentanone
2,3-Heptanedione
Eugenol
Isoeugenol
Ethyl isobutyrate
Isobutyl isobutyrate
Citronellyl isobutyrate
Tetrahydrofurfuryl alcohol
alpha-Terpineol
alpha-Methylbenzyl alcohol
alpha-Phellandrene
gamma-Terpinene
alpha-Terpinene
p-Cymene
Composé Inconnu
Forskolin
Sodium Sulfide hydrate
sodium methanethiolate
3-mercapto-1-pentanol
3-mercapto-2-methyl-1-butanol
3-Mercapto-3-methyl-1-hexanol
trimethylamine HCL
putrescine
cadaverine
morpholine
4-methylmorpholine
Urea
Androstadienol
geovertol TABLE 3-continued Complete list of odorant molecules tested on the 7 ORs of the invention.

methylgeosmin
1,3,5-trichloro-2-methoxybenzene
N-ethyl pyrrol
2,3,5-trimethyl pyridine
ammonium hydroxyde
1-cyclohexylethanol
1-cyclohexylethyl acetate
1-cyclohexylethyl butyrate
1-cyclohexylethyl propionate
Agarbois
Anapear
Anjeruk
Azurone
Belambre
Camonal
cis-3-hexenyl salicylate
cosmone
Dihydrofarnesal
Dihydromyrcenyl acetate
Ethylene Glycol Monophenoxyacetate
Florymoss
Georgywood
Heliotropin
nirvanolide
opalal
paradisamide
Pepperwood
Pharaone
rossitol
serenolide
(E)-6-ethyl-3-methyl-oct-6-en-1-ol
Tanaisone
tonkarose
ultravanil
undecanol
yara yara
methyl 1,3-dimethylcyclohexane-1-carboxylate
methyl 1,4-dimethylcyclohexane-1-carboxylate
undec-10-enenitrile
(9Z)-undec-9-enenitrile
(9E)-undec-9-enenitrile
1-{spiro[4.5]dec-7-en-7-yl}pent-4-en-1-one
1-{spiro[4.5]dec-7-en-7-yl}pent-4-en-1-one
tricyclo decenylacetate
Tricyclodecenyl propionate
2 ethyl 3,5 dimethyl pyrazine
2 ethyl 3,6 dimethyl pyrazine
Tetrahydro-4-methyl-2-(2-methyl-1-propenyl)-(2H)pyran
Helional
6-ethyl-3-methyl-oct-5-en-1-ol
Galaxolide
Ambrettolide
Habanolide
Muscenone
Traseolide
Moxalone
Florhydral
Furnisal
Polysantol
Ebanol
Javanol
Marenil
Indoclear
Pivacyclene
Neocaspirene
Herbanate
Methyl laitone
Ethyl laitone
Amber ketal
Ambermax (composé 1)
Ambermax (composé 2)
Ambrocenide
Metambrate
Spirambrene
1-(3,3-dimethylcyclohex-1-en-1-yl)pent-4-en-1-one
1-(5,5-dimethylcyclohex-1-en-1-yl)pent-4-en-1-one
Reseda Body
Ligustral Verdoracine
Vethymine
Alicate
Undecene-2-nitrile
Methyl diantilis
Toscanol
Safraleine
Levistamel
Dihydroisojasmonate
Carvacrol
Violet nitrile
4-methylidene-2-phenyloxane
4-methyl-2-phenyl-3,6-dihydro-2H-pyran
Pelargene
Dispirone
Gyrane
Glycolierral
Gardocyclene
Felvinone
Azarbre
PTBCHA high cis
Isobutylquinolene
Tetrahydronaphthol
Methyl epijasmonate
1(R)-2(S) Methyl epijasmonate
4-cyclohexyl-2-methylbutan-2-ol
methyl 2-(methylamino)benzoate
2-[2-(3,3,5-trimethylcyclohexyl)acetyl]cyclopentan-1-one
[4-(4-methylpent-3-en-1-yl)cyclohex-3-en-1-yl]methyl acetate
NEROLIONE
1-{10,10-dimethyl-2,6-dimethylidenebicyclo[7.2.0]undecan-5-yl}ethan-1-one
1-(4-tert-butylphenyl)-3-(4-methoxyphenyl)propane-1,3-dione
methyl 2-[(E)-(7-hydroxy-3,7-dimethyloctylidene)amino]benzoate
2-(2-methylphenyl)ethan-1-ol
2-phenylethyl 2-hydroxybenzoate
4-(2H-1,3-benzodioxol-5-yl)butan-2-one
(8E)-1,5,9-trimethyl-13-oxabicyclo[10.1.0]trideca-4,8-diene
2-ethoxy-4-[(propan-2-yloxy)methyl]phenol
3,4'-dimethylspiro[oxirane-2,9'-tricyclo[6.2.1.0^{2,7}]undecan]-4'-ene
3,4'-dimethylspiro[oxirane-2,9'-tricyclo[6.2.1.0^{2,7}]undecan]-4'-ene
3,4'-dimethylspiro[oxirane-2,9'-tricyclo[6.2.1.0^{2,7}]undecan]-4'-ene
(9E)-9-ethylidene-3-oxatricyclo[6.2.1.0^{2,7}]undecane
2,4,4,7-tetramethyloct-6-en-3-one
Cyclohexyl 2-hydroxybenzoate
(6E)-3,7-dimethylnona-1,6-dien-3-ol
(6Z)-3,7-dimethylnona-1,6-dien-3-yl acetate
ethyl 2-hydroxybenzoate
1-(3,3-dimethylcyclohexyl)pent-4-en-1-one
2-methyl-5-phenylpentan-1-ol
9-methoxytricyclo[5.2.1.0^{2,6}]decane-3-carbaldehyde
8-methoxytricyclo[5.2.1.0^{2,6}]dec-3-ene
methyl 2-{[(1E)-3-(4-tert-butylphenyl)-2-methylprop-1-en-1-yl]amino}benzoate
methyl 1,4a-dimethyl-7-(propan-2-yl)-1,2,3,4,4a,4b,5,6,7,8,10,10a-dodecahydrophenanthrene-1-carboxylate
1-methyl-4-(4-methylpentyl)cyclohex-3-ene-1-carbaldehyde
(4Z)-cyclooct-4-en-1-yl methyl carbonate
methyl 2-{[(1E)-2-(2H-1,3-benzodioxol-5-ylmethyl)prop-1-en-1-yl]amino}benzoate
2-methyldodecanal
4,4,8-trimethyltricyclo[6.3.1.0^{2,5}]dodecan-1-ol
2H,4H,4aH,5H,9bH-indeno[1,2-d][1,3]dioxine
8,8-bis(1H-indol-3-yl)-2,6-dimethyloctan-2-ol
ethyl 2-phenylbutanoate
(1E)-1-(2,6,6-trimethylcyclohex-2-en-1-yl)pent-1-en-3-one
3,5,5-trimethylhexyl propanoate
2-methylpropyl 2-hydroxybenzoate
methyl 2-{[(1E)-2-methylpent-1-en-1-yl]amino}benzoate
2,4,6-trimethylcyclohex-3-ene-1-carbaldehyde
3-(4-ethylphenyl)-2,2-dimethylpropanenitrile
8-(propan-2-yl)-1-oxaspiro[4.5]decan-2-one
2-(5-ethenyl-5-methyloxolan-2-yl)propan-2-ol TABLE 3-continued Complete list of odorant molecules tested on the 7 ORs of the invention.

2,4-dimethyl-2H,4H,4aH,5H,9bH-indeno[1,2-d][1,3]dioxine
1-[1-(3,3-dimethylcyclohexyl)ethoxy]-2-methylpropan-2-yl propanoate
2-[1-(3,3-dimethylcyclohexyl)ethoxy]-2-methylpropyl propanoate TABLE 3-continued Complete list of odorant molecules tested on the 7 ORs of the invention.

(3aR,5aS,9aS,9bS)-3a,6,6,9a-tetramethyl-2,4,5,5a,7,8,9,9b-octahydro-1H-benzo[e]benzofuran

The invention claimed is:
1. A method for identifying an agent that modulates the function of one or more Olfactory Receptor polypeptide(s) (ORs) selected from the group consisting of: OR52L1, OR52E8, OR52B2, OR51I2, OR52E1, OR52A5 and OR56A5 comprising the steps of:
   a) contacting said one or more ORs with one or more carboxylic acid(s) selected from the group of consisting of: butanoic acid, isovaleric acid, pentanoic acid, hexanoic acid, 2-methylhexanoic acid, 3-methylhexanoic acid, (E)-3-methly-2-hexenoic acid, 3-hydroxy-3-methylhexanoic acid, heptanoic acid, 2-methylheptanoic acid, octanoic acid, 4-ethyloctanoic acid, nonanoic acid, decanoic acid, undecanoic acid and benzoic acid, in the presence and in the absence of said agent under conditions permitting the binding of said carboxylic acid(s) to said ORs or permitting the activation of said ORs by said carboxylic acid(s),
   b) comparing the binding of said one or more ORs to said one or more carboxylic acid(s), or the activity of said one or more ORs, in the presence and in the absence of said agent, wherein a difference in binding or activity in the presence of said agent, relative to the binding or activity in the absence of the agent, identifies the agent as an agent that modulates the function of said one or more ORs in response to said one or more carboxylic acid(s).

2. The method according to claim 1, wherein said agent is tested for influencing the binding of said carboxylic acids to all 7 ORs listed therein, or for influencing the activation of all 7 ORs listed therein by said carboxylic acids.

3. The method according to claim 1, wherein said agent is tested for influencing the binding of pentanoic acid to OR52L1, or for influencing the activation of OR52L1 by pentanoic acid.

4. The method according to claim 1, wherein said agent is tested for influencing the binding of 3-hydroxy-3-methylhexanoic acid to OR52E8, or for influencing the activation of OR52E8 by 3-hydroxy-3-methylhexanoic acid.

5. The method according to claim 1, wherein said agent is tested for influencing the binding of hexanoic acid, heptanoic acid, octanoic acid, nonanoic acid, decanoic acid, or undecanoic acid to OR52B2, or for influencing the activation of OR52B2 by hexanoic acid, heptanoic acid, octanoic acid, nonanoic acid, decanoic acid, or undecanoic acid.

6. The method according to claim 1, wherein said agent is tested for influencing the binding of butanoic acid, isovaleric acid, pentanoic acid, hexanoic acid, 2-methylhexanoic acid, 3-methylhexanoic acid, (E)-3-methyl-2-hexenoic acid, or benzoic acid to OR51I2, or for influencing the activation of OR51I2 by butanoic acid, isovaleric acid, pentanoic acid, hexanoic acid, 2-methylhexanoic acid, 3-methylhexanoic acid, (E)-3-methyl-2-hexenoic acid, or benzoic acid.

7. The method according to claim 1, wherein said agent is tested for influencing the binding of butanoic acid to OR52E1, or for influencing the activation of OR52E1 by butanoic acid.

8. The method according to claim 1, wherein said agent is tested for influencing the binding of 4-ethyloctanoic acid to OR52A5, or for influencing the activation of OR52A5 by 4-ethyloctanoic acid.

9. The method according to claim 1, wherein said agent is tested for influencing the binding of hexanoic acid, heptanoic acid, 2-methylheptanoic acid, octanoic acid, nonanoic acid, decanoic acid, or undecanoic acid to OR56A5, or for influencing the activation of OR56A5 by hexanoic acid, heptanoic acid, 2-methylheptanoic acid, octanoic acid, nonanoic acid, decanoic acid, or undecanoic acid.

10. The method according to claim 1, wherein said one or more OR polypeptides is defined by the amino acid sequence of SEQ ID NOs: 2, 4, 6, 8, 10, 12 or 14.

11. The method according to claim 1, wherein said one or more carboxylic acid(s) may be detectably labeled with a moiety selected from the group comprising: a radioisotope, a fluorophore, and a quencher of fluorescence.

12. The method according to claim 1, used for detecting the presence of an agent that modulates the activity of one or more ORs detecting carboxylic acids present in human sweat in a sample.

13. The method according to claim 1, wherein said agent is present in a sample.

14. The method according to claim 1, in which said one or more OR polypeptide(s) is contacted with said one or more carboxylic acid(s) at their EC50 concentration.

15. The method according to claim 1, wherein said agent is identified as an agent that modulates the function of ORs according to the invention, when said agent decreases the intracellular response induced by said carboxylic acid(s), by at least 10%.

16. The method according to claim 1, wherein the contacting is performed in or on a cell expressing said OR polypeptide.

17. The method according to claim 16, wherein said cell is selected from: Human embryonic kidney cells (Hek293), Chinese hamster cells (CHO), Monkey cells (COS), primary olfactory cells, *Xenopus* cells, insect cells, yeast or bacteria.

18. The method according to claim 1, wherein said contacting is performed using synthetic liposomes or virus-induced budding membranes containing said OR polypeptide.

19. The method according to claim 1, wherein said method is performed using a membrane fraction from cells expressing said OR polypeptide.

20. The method according to claim 1, wherein said method is performed on a protein chip.

21. The method according to claim 1, wherein said measuring is performed using a method selected from label displacement, surface plasmon resonance, fluorescence resonance energy transfer, fluorescence quenching, and fluorescence polarization.

22. The method according to claim 1, wherein said agent is selected from the group consisting of a peptide, a polypeptide, an antibody or antigen-binding fragment thereof, a lipid, a carbohydrate, a nucleic acid, and a small organic molecule.

23. The method according to claim 1, wherein the activity of said OLR polypeptide is measured by detecting a change in the level of a second messenger.

24. The method according to claim 1, wherein the activity of said OR polypeptide is measured by measurement of guanine nucleotide binding/coupling or exchange, adenylate cyclase activity, cAMP, Protein Kinase C activity, Protein Kinase A activity phosphatidylinosotol breakdown, diacylglycerol, inositol triphosphate, intracellular calcium, calcium flux, arachidonic acid, MAP kinase activity, tyrosine kinase activity, a melanophore assay, a receptor initialization assay, or reporter gene expression.

25. The method according to claim 1, wherein the activity of said ORs is measured using a fluorescence or luminescence assay.

26. The method according to claim 25, wherein said fluorescence and luminescence assays comprise the use of $Ca^{2+}$-sensitive fluorophores including Fluo3, Fluo4 or Fura; Ca3-kit family or aequorin.

27. The method according to claim 26, wherein said assays apply an automated fluorometric or luminescent reader such as Functional Drug Screening System (FDSS) or Fluorometric Imaging Plate Reader (FLIPR).

28. The method according to claim 1, which is a high-throughput screening method.

29. The method according to claim 1, wherein the agent is part of a chemical library or animal organ extracts.

30. A kit for performing screening methods for modulators of Olfactory Receptors (ORs) detecting carboxylic acid(s) present in human sweat, comprising:
   a) isolated OR polypeptides: OR52L1, OR52E8, OR52B2, OR51I2, OR52E1, OR52A5 and OR56A5;
   b) one or more carboxylic acid(s) selected from the group of consisting of: butanoic acid, isovaleric acid, pentanoic acid, hexanoic acid, 2-methylhexanoic acid, 3-methylhexanoic acid, (E)-3-methly-2-hexenoic acid, 3-hydroxy-3-methylhexanoic acid, heptanoic acid, 2-methylheptanoic acid, octanoic acid, 4-ethyloctanoic acid, nonanoic acid, decanoic acid, undecanoic acid and benzoic acid; and
   c) packaging materials therefore.

31. A kit for performing screening methods for modulators of Olfactory Receptors (ORs) detecting carboxylic acid(s) present in human sweat, comprising:
   a) isolated polynucleotide's encoding the OR polypeptides: OR52L1, OR52E8, OR52B2, OR51I2, OR52E1, OR52A5 and OR56A5;
   b) carboxylic acid(s) selected from the group consisting of: butanoic acid, isovaleric acid, pentanoic acid, hexanoic acid, 2-methylhexanoic acid, 3-methylhexanoic acid, (E)-3-methly-2-hexenoic acid, 3-hydroxy-3-methylhexanoic acid, heptanoic acid, 2-methylheptanoic acid, octanoic acid, 4-ethyloctanoic acid, nonanoic acid, decanoic acid, undecanoic acid and benzoic acid; and
   c) packaging materials therefore.

32. A kit for performing screening methods for modulators of Olfactory Receptors (ORs) detecting carboxylic acid(s) present in human sweat, comprising:
   a) a cell, several cells or membranes thereof expressing one or more of the OR polypeptides OR52L1, OR52E8, OR52B2, OR51I2, OR52E1, OR52A5 and OR56A5;
   b) carboxylic acid(s) selected from the group of consisting of: butanoic acid, isovaleric acid, pentanoic acid, hexanoic acid, 2-methylhexanoic acid, 3-methylhexanoic acid, (E)-3-methly-2-hexenoic acid, 3-hydroxy-3-methylhexanoic acid, heptanoic acid, 2-methylheptanoic acid, octanoic acid, 4-ethyloctanoic acid, nonanoic acid, decanoic acid, undecanoic acid and benzoic acid; and
   c) packaging materials therefore.

33. A kit for performing screening methods for modulators of Olfactory Receptors (ORs) detecting carboxylic acid(s) present in human sweat, comprising:
   a) a cell, several cells or membranes thereof expressing one or more of the OR polypeptides OR52L1, OR52E8, OR52B2, OR51I2, OR52E1, OR52A5 and OR56A5;
   b) carboxylic acid(s) selected from the group of consisting of: butanoic acid, isovaleric acid, pentanoic acid, hexanoic acid, 2-methylhexanoic acid, 3-methylhexanoic acid, (E)-3-methly-2-hexenoic acid, 3-hydroxy-3-methylhexanoic acid, heptanoic acid, 2-methylheptanoic acid, octanoic acid, 4-ethyloctanoic acid, nonanoic acid, decanoic acid, undecanoic acid and benzoic acid; and
   c) packaging materials therefore, wherein said cell is transformed with a polynucleotide encoding said one or more OR(s).

* * * * *

SEQUENCE LISTING

<160> NUMBER OF SEQ ID NOS: 22

<210> SEQ ID NO 1
<211> LENGTH: 990
<212> TYPE: DNA
<213> ORGANISM: Homo sapiens

<400> SEQUENCE: 1

```
atgactttgg tttctttttt ctctttcctc tccaagccat tgataatgct ccttagcaat      60
tcaagctgga ggctatccca gccttctttt ctcctggtag ggattccagg tttagaggaa     120
agccagcact ggattgcact gcccctgggc atcctttacc tccttgcttt agtgggcaat     180
gttaccattc tcttcatcat ctggatggac ccatccttgc accaatctat gtacctcttc     240
ctgtccatgc tagctgccat cgacctggtt ctggcctcct ccactgcacc caaagccctt     300
gcagtgctcc tggttcatgc ccacgagatt gggtacatcg tctgcctgat ccagatgttc     360
ttcatccatg cattctcctc catggagtta ggggtacttg tggccatggc tctggattgc     420
tatgtagcca tttgtcaccc cttgcaccat tccacaatcc tgcatccagg ggtcataggg     480
cgcatcggaa tggtggtgct ggtgagggga ttactactcc ttatcccctt ccccattttg     540
ttgggaacac ttatcttctg ccaagccacc atcataggcc atgcctattg tgaacatatg     600
gctgttgtga acttgcctg ctcagaaacc acagtcaatc gagcttatgg gctgactatg     660
gccttgcttg tgattgggct ggatgttctg gccattggtg tttcctatgc ccacatcctc     720
caggcagtgc tgaaggtacc agggagtgag gcccgactta aggcgtttag cacatgtggc     780
tctcatattt gtgtcatcct ggtcttctat gtccctggaa ttttctcctt cctcactcac     840
cgctttggtc atcatgtacc ccatcatgtc catgttcttc tggccacacg gtatctcctc     900
atgccacctg cgctcaatcc tcttgtctat ggagtgaaga ctcagcagat ccgccagcga     960
gtgctcagag tgtttacaca aaaggattaa                                      990
```

<210> SEQ ID NO 2
<211> LENGTH: 329
<212> TYPE: PRT
<213> ORGANISM: Homo sapiens

<400> SEQUENCE: 2

```
Met Thr Leu Val Ser Phe Phe Ser Phe Leu Ser Lys Pro Leu Ile Met
1               5                   10                  15

Leu Leu Ser Asn Ser Ser Trp Arg Leu Ser Gln Pro Ser Phe Leu Leu
            20                  25                  30

Val Gly Ile Pro Gly Leu Glu Glu Ser Gln His Trp Ile Ala Leu Pro
        35                  40                  45

Leu Gly Ile Leu Tyr Leu Leu Ala Leu Val Gly Asn Val Thr Ile Leu
    50                  55                  60

Phe Ile Ile Trp Met Asp Pro Ser Leu His Gln Ser Met Tyr Leu Phe
65                  70                  75                  80

Leu Ser Met Leu Ala Ala Ile Asp Leu Val Leu Ala Ser Ser Thr Ala
```

|   |   |   |   |   | 85 |   |   |   | 90 |   |   |   |   | 95 |   |
|---|---|---|---|---|---|---|---|---|---|---|---|---|---|---|---|

Pro Lys Ala Leu Ala Val Leu Leu Val His Ala His Glu Ile Gly Tyr
        100               105           110

Ile Val Cys Leu Ile Gln Met Phe Phe Ile His Ala Phe Ser Ser Met
        115               120           125

Glu Leu Gly Val Leu Val Ala Met Ala Leu Asp Cys Tyr Val Ala Ile
        130               135           140

Cys His Pro Leu His His Ser Thr Ile Leu His Pro Gly Val Ile Gly
145             150              155            160

Arg Ile Gly Met Val Val Leu Val Arg Gly Leu Leu Leu Ile Pro
        165               170           175

Phe Pro Ile Leu Leu Gly Thr Leu Ile Phe Cys Gln Ala Thr Ile Ile
        180               185           190

Gly His Ala Tyr Cys Glu His Met Ala Val Val Lys Leu Ala Cys Ser
        195               200           205

Glu Thr Thr Val Asn Arg Ala Tyr Gly Leu Thr Met Ala Leu Leu Val
210             215              220

Ile Gly Leu Asp Val Leu Ala Ile Gly Val Ser Tyr Ala His Ile Leu
225             230              235            240

Gln Ala Val Leu Lys Val Pro Gly Ser Glu Ala Arg Leu Lys Ala Phe
        245               250           255

Ser Thr Cys Gly Ser His Ile Cys Val Ile Leu Val Phe Tyr Val Pro
        260               265           270

Gly Ile Phe Ser Phe Leu Thr His Arg Phe Gly His His Val Pro His
        275               280           285

His Val His Val Leu Leu Ala Thr Arg Tyr Leu Leu Met Pro Pro Ala
        290               295           300

Leu Asn Pro Leu Val Tyr Gly Val Lys Thr Gln Gln Ile Arg Gln Arg
305             310              315            320

Val Leu Arg Val Phe Thr Gln Lys Asp
        325

<210> SEQ ID NO 3
<211> LENGTH: 954
<212> TYPE: DNA
<213> ORGANISM: Homo sapiens

<400> SEQUENCE: 3

```
atggcaggaa gaatgtctac gtctaatcac acccagttcc atccttcttc attcctactg      60
ctgggtatcc cagggctaga agatgtgcac atttggattg gtgtcccttt tttctttgtg     120
tatcttgttg cactcctggg aaacactgct ctcttgtttg tgatccagac tgagcagagt     180
ctccatgagc ctatgtacta cttcctggcc atgttggatt ccattgacct gggcttgtct     240
acagccacca tccccaaaat gttgggcatc ttctggttca ataccaaaga aatatctttt     300
ggaggctgcc tttctcacat gttcttcatc catttcttca ctgctatgga gagcattgtg     360
ttggtggcca tggcctttga ccgctacatt gccatttgca aacctcttcg gtacaccatg     420
atcctcacca gcaaaatcat cagcctcatt gcaggcattg ctgtcctgag agcctgtac     480 atggttgttc cactggtgtt tctccttctg aggctgccct ctgtgggca tcgtatcatc     540 cctcatactt attgtgagca catgggcatt gcccgtctgg cctgtgccag catcaaagtc     600
aacattaggt ttggccttgg caacatatct ctccttgttac tggatgttat cctattatt     660 ctctcctatg tcaggatcct gtatgctgtc ttctgcctgc cctcctggga agctcgactc     720
aaagctctca cacctgtggg ttctcatatt ggtgttatct tagccttttt tacaccagca     780
```

```
tttttttcat tcttgacaca tcgttttggc cataatatcc cacagtatat acatattata    840
ttagccaacc tgtatgtggt tgtcccacca gccctcaatc ctgtaatcta tggagtcagg    900
acaaagcaga ttcgagagag agtgctgagg attttctca agaccaatca ctaa          954
```

<210> SEQ ID NO 4
<211> LENGTH: 317
<212> TYPE: PRT
<213> ORGANISM: Homo sapiens

<400> SEQUENCE: 4

```
Met Ala Gly Arg Met Ser Thr Ser Asn His Thr Gln Phe His Pro Ser
1               5                   10                  15

Ser Phe Leu Leu Leu Gly Ile Pro Gly Leu Glu Asp Val His Ile Trp
            20                  25                  30

Ile Gly Val Pro Phe Phe Val Tyr Leu Val Ala Leu Leu Gly Asn
        35                  40                  45

Thr Ala Leu Leu Phe Val Ile Gln Thr Glu Gln Ser Leu His Glu Pro
    50                  55                  60

Met Tyr Tyr Phe Leu Ala Met Leu Asp Ser Ile Asp Leu Gly Leu Ser
65                  70                  75                  80

Thr Ala Thr Ile Pro Lys Met Leu Gly Ile Phe Trp Phe Asn Thr Lys
                85                  90                  95

Glu Ile Ser Phe Gly Gly Cys Leu Ser His Met Phe Phe Ile His Phe
            100                 105                 110

Phe Thr Ala Met Glu Ser Ile Val Leu Val Ala Met Ala Phe Asp Arg
        115                 120                 125

Tyr Ile Ala Ile Cys Lys Pro Leu Arg Tyr Thr Met Ile Leu Thr Ser
    130                 135                 140

Lys Ile Ile Ser Leu Ile Ala Gly Ile Ala Val Leu Arg Ser Leu Tyr
145                 150                 155                 160

Met Val Val Pro Leu Val Phe Leu Leu Leu Arg Leu Pro Phe Cys Gly
                165                 170                 175

His Arg Ile Ile Pro His Thr Tyr Cys Glu His Met Gly Ile Ala Arg
            180                 185                 190

Leu Ala Cys Ala Ser Ile Lys Val Asn Ile Arg Phe Gly Leu Gly Asn
        195                 200                 205

Ile Ser Leu Leu Leu Leu Asp Val Ile Leu Ile Leu Ser Tyr Val
    210                 215                 220

Arg Ile Leu Tyr Ala Val Phe Cys Leu Pro Ser Trp Glu Ala Arg Leu
225                 230                 235                 240

Lys Ala Leu Asn Thr Cys Gly Ser His Ile Gly Val Ile Leu Ala Phe
                245                 250                 255

Phe Thr Pro Ala Phe Phe Ser Phe Leu Thr His Arg Phe Gly His Asn
            260                 265                 270

Ile Pro Gln Tyr Ile His Ile Ile Leu Ala Asn Leu Tyr Val Val Val
        275                 280                 285

Pro Pro Ala Leu Asn Pro Val Ile Tyr Gly Val Arg Thr Lys Gln Ile
    290                 295                 300

Arg Glu Arg Val Leu Arg Ile Phe Leu Lys Thr Asn His
305                 310                 315
```

<210> SEQ ID NO 5
<211> LENGTH: 972
<212> TYPE: DNA
<213> ORGANISM: Homo sapiens

<400> SEQUENCE: 5

```
atgagtcaca ccaatgttac catcttccat cctgcagttt ttgtccttcc tggcatccct      60
gggttggagg cttatcacat ttggctgtca atacctcttt gcctcattta catcactgca     120
gtcctgggaa acagcatcct gatagtggtt attgtcatgg aacgtaacct tcatgtgccc     180
atgtatttct tcctctcaat gctggccgtc atggacatcc tgctgtctac caccactgtg     240
cccaaggccc tagccatctt ttggcttcaa gcacataaca ttgcttttga tgcctgtgtc     300
acccaaggct tctttgtcca tatgatgttt gtggggagt cagctatcct gttagccatg     360
gcctttgatc gctttgtggc catttgtgcc ccactgagat atacaacagt gctaacatgg     420
cctgttgtgg ggaggattgc tctggccgtc atcacccgaa gcttctgcat catcttccca     480
gtcatattct tgctgaagcg gctgcccttc tgcctaacca acattgttcc tcactcctac     540
tgtgagcata ttggagtggc tcgtttagcc tgtgctgaca tcactgttaa catttggtat     600
ggcttctcag tgcccattgt catggtcatc ttggatgtta tcctcatcgc tgtgtcttac     660
tcactgatcc tccgagcagt gtttcgtttg ccctcccagg atgctcggca aaggccctc     720
agcacttgtg gctcccacct ctgtgtcatc cttatgtttt atgttccatc cttctttacc     780
ttattgaccc atcattttgg gcgtaatatt cctcaacatg tccatatctt gctggccaat     840
ctttatgtgg cagtgccacc aatgctgaac cccattgtct atggtgtgaa gactaagcag     900
atacgtgagg gtgtagccca ccggttcttt gacatcaaga cttggtgctg tacctcccct     960
ctgggctcat aa                                                         972
```

<210> SEQ ID NO 6
<211> LENGTH: 323
<212> TYPE: PRT
<213> ORGANISM: Homo sapiens

<400> SEQUENCE: 6

```
Met Ser His Thr Asn Val Thr Ile Phe His Pro Ala Val Phe Val Leu
1               5                   10                  15

Pro Gly Ile Pro Gly Leu Glu Ala Tyr His Ile Trp Leu Ser Ile Pro
            20                  25                  30

Leu Cys Leu Ile Tyr Ile Thr Ala Val Leu Gly Asn Ser Ile Leu Ile
        35                  40                  45

Val Val Ile Val Met Glu Arg Asn Leu His Val Pro Met Tyr Phe Phe
    50                  55                  60

Leu Ser Met Leu Ala Val Met Asp Ile Leu Leu Ser Thr Thr Thr Val
65                  70                  75                  80

Pro Lys Ala Leu Ala Ile Phe Trp Leu Gln Ala His Asn Ile Ala Phe
                85                  90                  95

Asp Ala Cys Val Thr Gln Gly Phe Phe Val His Met Met Phe Val Gly
            100                 105                 110

Glu Ser Ala Ile Leu Leu Ala Met Ala Phe Asp Arg Phe Val Ala Ile
        115                 120                 125

Cys Ala Pro Leu Arg Tyr Thr Thr Val Leu Thr Trp Pro Val Val Gly
    130                 135                 140

Arg Ile Ala Leu Ala Val Ile Thr Arg Ser Phe Cys Ile Ile Phe Pro
145                 150                 155                 160

Val Ile Phe Leu Leu Lys Arg Leu Pro Phe Cys Leu Thr Asn Ile Val
                165                 170                 175

Pro His Ser Tyr Cys Glu His Ile Gly Val Ala Arg Leu Ala Cys Ala
            180                 185                 190
```

Asp Ile Thr Val Asn Ile Trp Tyr Gly Phe Ser Val Pro Ile Val Met
195                 200                 205

Val Ile Leu Asp Val Ile Leu Ile Ala Val Ser Tyr Ser Leu Ile Leu
210                 215                 220

Arg Ala Val Phe Arg Leu Pro Ser Gln Asp Arg His Lys Ala Leu
225                 230                 235                 240

Ser Thr Cys Gly Ser His Leu Cys Val Ile Leu Met Phe Tyr Val Pro
                245                 250                 255

Ser Phe Phe Thr Leu Leu Thr His His Phe Gly Arg Asn Ile Pro Gln
                260                 265                 270

His Val His Ile Leu Leu Ala Asn Leu Tyr Val Ala Val Pro Pro Met
275                 280                 285

Leu Asn Pro Ile Val Tyr Gly Val Lys Thr Lys Gln Ile Arg Glu Gly
            290                 295                 300

Val Ala His Arg Phe Phe Asp Ile Lys Thr Trp Cys Cys Thr Ser Pro
305                 310                 315                 320

Leu Gly Ser

<210> SEQ ID NO 7
<211> LENGTH: 939
<212> TYPE: DNA
<213> ORGANISM: Homo sapiens

<400> SEQUENCE: 7

```
atggggttgt tcaatgtcac tcaccctgca ttcttcctcc tgactggtat ccctggtctg      60
gagagctctc actcctggct gtcagggccc ctctgcgtga tgtatgctgt ggcccttggg     120
ggaaatacag tgatcctgca ggctgtgcga gtggagccca gctccatga gcccatgtac     180
tacttcctgt ccatgttgtc cttcagtgat gtggccatat ccatggccac actgcccact     240
gtactccgaa ccttctgcct caatgcccgc aacatcactt ttgatgcctg tctaattcag     300
atgtttctta ttcacttctt ctccatgatg aatcaggta ttctgctggc catgagtttt     360
gaccgctatg tggccatttg tgacccccttg cgctatgcag ctgtgctcac cactgaagtc     420
attgctgcaa tgggtttagg tgcagctgct cgaagcttca tcacccttttt ccctcttccc     480
tttcttatta gaggctgcc tatctgcaga tccaatgttc tttctcactc ctactgcctg     540
cacccagaca tgatgaggct tgcctgtgct gatatcagta tcaacagcat ctatggactc     600
tttgttcttg tatccacctt tggcatggac ctgttttta tcttcctctc ctatgtgctc     660
attctgcgtt ctgtcatggc cactgcttcc cgtgaggaac gcctcaaagc tctcaacaca     720
tgtgtgtcac atatcctggc tgtacttgca ttttatgtgc caatgattgg ggtctccaca     780
gtgcaccgct ttgggaagca tgtcccatgc tacatacatg tcctcatgtc aaatgtgtac     840
ctatttgtgc ctcctgtgct caaccctctc atttatagcg ccaagacaaa ggaaatccgc     900
cgagccattt tccgcatgtt tcaccacatc aaaatatga                             939
```

<210> SEQ ID NO 8
<211> LENGTH: 312
<212> TYPE: PRT
<213> ORGANISM: Homo sapiens

<400> SEQUENCE: 8

Met Gly Leu Phe Asn Val Thr His Pro Ala Phe Phe Leu Leu Thr Gly
1               5                   10                  15

Ile Pro Gly Leu Glu Ser Ser His Ser Trp Leu Ser Gly Pro Leu Cys
            20                  25                  30

Val Met Tyr Ala Val Ala Leu Gly Gly Asn Thr Val Ile Leu Gln Ala
             35                  40                  45

Val Arg Val Glu Pro Ser Leu His Glu Pro Met Tyr Tyr Phe Leu Ser
 50                  55                  60

Met Leu Ser Phe Ser Asp Val Ala Ile Ser Met Ala Thr Leu Pro Thr
 65                  70                  75                  80

Val Leu Arg Thr Phe Cys Leu Asn Ala Arg Asn Ile Thr Phe Asp Ala
                 85                  90                  95

Cys Leu Ile Gln Met Phe Leu Ile His Phe Phe Ser Met Met Glu Ser
                100                 105                 110

Gly Ile Leu Leu Ala Met Ser Phe Asp Arg Tyr Val Ala Ile Cys Asp
            115                 120                 125

Pro Leu Arg Tyr Ala Ala Val Leu Thr Thr Glu Val Ile Ala Ala Met
        130                 135                 140

Gly Leu Gly Ala Ala Ala Arg Ser Phe Ile Thr Leu Phe Pro Leu Pro
145                 150                 155                 160

Phe Leu Ile Lys Arg Leu Pro Ile Cys Arg Ser Asn Val Leu Ser His
                165                 170                 175

Ser Tyr Cys Leu His Pro Asp Met Met Arg Leu Ala Cys Ala Asp Ile
            180                 185                 190

Ser Ile Asn Ser Ile Tyr Gly Leu Phe Val Leu Val Ser Thr Phe Gly
        195                 200                 205

Met Asp Leu Phe Phe Ile Phe Leu Ser Tyr Val Leu Ile Leu Arg Ser
210                 215                 220

Val Met Ala Thr Ala Ser Arg Glu Glu Arg Leu Lys Ala Leu Asn Thr
225                 230                 235                 240

Cys Val Ser His Ile Leu Ala Val Leu Ala Phe Tyr Val Pro Met Ile
                245                 250                 255

Gly Val Ser Thr Val His Arg Phe Gly Lys His Val Pro Cys Tyr Ile
            260                 265                 270

His Val Leu Met Ser Asn Val Tyr Leu Phe Val Pro Pro Val Leu Asn
        275                 280                 285

Pro Leu Ile Tyr Ser Ala Lys Thr Lys Glu Ile Arg Arg Ala Ile Phe
    290                 295                 300

Arg Met Phe His His Ile Lys Ile
305                 310

<210> SEQ ID NO 9
<211> LENGTH: 927
<212> TYPE: DNA
<213> ORGANISM: Homo sapiens

<400> SEQUENCE: 9
atgaatacca ctctatttca tccttactct ttccttcttc tgggaattcc tgggctggaa      60
agtatgcatc tctggttggt tttcctttc tttgctgtgt tcctgacagc tgtccttggg     120
aatatcacca tcctttttgt gattcagact gacagtagtc tccatcatcc catgttctac     180
ttcctggcca ttctgtcatc tattgacccg ggcctgtcta catccaccat ccctaaaatg     240
cttggcacct tctggtttac cctgagagaa atctcctttg aaggatgcct acccagatg     300 ttcttcatcc acctgtgcac tggcatggaa tcagctgtgc ttgtggccat ggctatgat     360 tgctatgtgg ccatctgtga ccctcttttgc tacacgttgg tgctgacaaa caaggtggtg     420
tcagttatgg cactggccat cttctctgaga cccttagtct ttgtcatacc ctttgttcta     480
tttatcctaa ggcttccatt tgtggacac caaattattc ctcatactta cggtgagcac     540

```
atgggcattg cccgcctgtc ttgtgccagc atcagggtta acatcatcta tggcttatgt    600
gccatctcta tcctggtctt tgacatcata gcaattgtca tttcctatgt acagatcctt    660
tgtgctgtat ttctactctc ttcacatgat gcacgactca aggcattcag cacctgtggc    720
tctcatgtgt gtgtcatgtt gactttctat atgcctgcat tgttctcatt catgacccat    780
aggtttggtc ggaatatacc tcactttatc cacattcttc tggctaattt ctgtgtagtc    840
attccacctg ctctcaactc tgtaatttat ggtgtcagaa ccaaacagat tagagcacaa    900
gtgctgaaaa tgttttcaa taaataa    927
```

```
<210> SEQ ID NO 10
<211> LENGTH: 308
<212> TYPE: PRT
<213> ORGANISM: Homo sapiens

<400> SEQUENCE: 10
```

```
Met Asn Thr Thr Leu Phe His Pro Tyr Ser Phe Leu Leu Gly Ile
  1               5                  10                  15

Pro Gly Leu Glu Ser Met His Leu Trp Val Gly Phe Pro Phe Phe Ala
                 20                  25                  30

Val Phe Leu Thr Ala Val Leu Gly Asn Ile Thr Ile Leu Phe Val Ile
             35                  40                  45

Gln Thr Asp Ser Ser Leu His His Pro Met Phe Tyr Phe Leu Ala Ile
         50                  55                  60

Leu Ser Ser Ile Asp Pro Gly Leu Ser Thr Ser Thr Ile Pro Lys Met
 65                  70                  75                  80

Leu Gly Thr Phe Trp Phe Thr Leu Arg Glu Ile Ser Phe Glu Gly Cys
                 85                  90                  95

Leu Thr Gln Met Phe Phe Ile His Leu Cys Thr Gly Met Glu Ser Ala
            100                 105                 110

Val Leu Val Ala Met Ala Tyr Asp Cys Tyr Val Ala Ile Cys Asp Pro
        115                 120                 125

Leu Cys Tyr Thr Leu Val Leu Thr Asn Lys Val Val Ser Val Met Ala
    130                 135                 140

Leu Ala Ile Phe Leu Arg Pro Leu Val Phe Val Ile Pro Phe Val Leu
145                 150                 155                 160

Phe Ile Leu Arg Leu Pro Phe Cys Gly His Gln Ile Ile Pro His Thr
                165                 170                 175

Tyr Gly Glu His Met Gly Ile Ala Arg Leu Ser Cys Ala Ser Ile Arg
            180                 185                 190

Val Asn Ile Ile Tyr Gly Leu Cys Ala Ile Ser Ile Leu Val Phe Asp
        195                 200                 205

Ile Ile Ala Ile Val Ile Ser Tyr Val Gln Ile Leu Cys Ala Val Phe
    210                 215                 220

Leu Leu Ser Ser His Asp Ala Arg Leu Lys Ala Phe Ser Thr Cys Gly
225                 230                 235                 240

Ser His Val Cys Val Met Leu Thr Phe Tyr Met Pro Ala Leu Phe Ser
                245                 250                 255

Phe Met Thr His Arg Phe Gly Arg Asn Ile Pro His Phe Ile His Ile
            260                 265                 270

Leu Leu Ala Asn Phe Cys Val Val Ile Pro Pro Ala Leu Asn Ser Val
        275                 280                 285

Ile Tyr Gly Val Arg Thr Lys Gln Ile Arg Ala Gln Val Leu Lys Met
    290                 295                 300
```

Phe Phe Asn Lys
305

<210> SEQ ID NO 11
<211> LENGTH: 945
<212> TYPE: DNA
<213> ORGANISM: Homo sapiens

<400> SEQUENCE: 11

```
atgccgacat tcaatggctc agtcttcatg ccctctgcgt ttatactaat tgggattcct      60
ggtctggagt cagtgcagtg ttggattggg attccttttct ctgccatgta tcttattggt    120
gtgattggaa attccctaat tttagttata atcaaatatg aaaacagcct ccatataccc    180
atgtacattt ttttggccat gttggcagcc acagacattg cacttaacac ctgcattctt    240
cccaaaatgt taggcatctt ctggtttcat ttgccagaga tttcttttga tgcctgtctt    300
tttcaaatgt ggcttattca ctcattccag gcaattgaat cgggtatcct tctggcaatg    360
gccctggatc gctatgtggc catctgtatc cccttgagac atgccaccat cttttcccag    420
cagttcttaa ctcatattgg acttggggtg acactcaggg ctgccattct tataatacct    480
tccttagggc tcatcaaatg ctgtctgaaa cactatcgaa ctacagtcat ctctcactct    540
tactgtgagc acatggccat cgtgaagctg gctactgaag atatccgagt caacaagata    600
tatggcctat tgttgccttt gcaatcctag ggtttgaca taatatttat aaccttgtcc    660
tatgtccaaa tttttatcac tgtctttcag ctgccccaga aggaggcacg attcaaggcc    720
tttaatacat gcattgccca catttgtgtc ttcctacagt tctacttcct tgccttcttc    780
tctttcttca cacacaggtt tggttcacac ataccaccat atattcatat cctcttgtca    840
aatctttacc tgttagtccc accttttctc aaccctattg tctatggagt gaagaccaag    900
caaattcgtg accatattgt gaaagtgttt ttcttcaaaa agtaa                    945
```

<210> SEQ ID NO 12
<211> LENGTH: 314
<212> TYPE: PRT
<213> ORGANISM: Homo sapiens

<400> SEQUENCE: 12

Met Pro Thr Phe Asn Gly Ser Val Phe Met Pro Ser Ala Phe Ile Leu
1               5                   10                  15

Ile Gly Ile Pro Gly Leu Glu Ser Val Gln Cys Trp Ile Gly Ile Pro
            20                  25                  30

Phe Ser Ala Met Tyr Leu Ile Gly Val Ile Gly Asn Ser Leu Ile Leu
        35                  40                  45

Val Ile Ile Lys Tyr Glu Asn Ser Leu His Ile Pro Met Tyr Ile Phe
    50                  55                  60

Leu Ala Met Leu Ala Ala Thr Asp Ile Ala Leu Asn Thr Cys Ile Leu
65                  70                  75                  80

Pro Lys Met Leu Gly Ile Phe Trp Phe His Leu Pro Glu Ile Ser Phe
                85                  90                  95

Asp Ala Cys Leu Phe Gln Met Trp Leu Ile His Ser Phe Gln Ala Ile
            100                 105                 110

Glu Ser Gly Ile Leu Leu Ala Met Ala Leu Asp Arg Tyr Val Ala Ile
        115                 120                 125

Cys Ile Pro Leu Arg His Ala Thr Ile Phe Ser Gln Gln Phe Leu Thr
    130                 135                 140

His Ile Gly Leu Gly Val Thr Leu Arg Ala Ala Ile Leu Ile Ile Pro
145                 150                 155                 160

Ser Leu Gly Leu Ile Lys Cys Cys Leu Lys His Tyr Arg Thr Thr Val
            165                 170                 175

Ile Ser His Ser Tyr Cys Glu His Met Ala Ile Val Lys Leu Ala Thr
        180                 185                 190

Glu Asp Ile Arg Val Asn Lys Ile Tyr Gly Leu Phe Val Ala Phe Ala
            195                 200                 205

Ile Leu Gly Phe Asp Ile Phe Ile Thr Leu Ser Tyr Val Gln Ile
    210                 215                 220

Phe Ile Thr Val Phe Gln Leu Pro Gln Lys Glu Ala Arg Phe Lys Ala
225                 230                 235                 240

Phe Asn Thr Cys Ile Ala His Ile Cys Val Phe Leu Gln Phe Tyr Leu
                245                 250                 255

Leu Ala Phe Phe Ser Phe Phe Thr His Arg Phe Gly Ser His Ile Pro
            260                 265                 270

Pro Tyr Ile His Ile Leu Leu Ser Asn Leu Tyr Leu Leu Val Pro Pro
        275                 280                 285

Phe Leu Asn Pro Ile Val Tyr Gly Val Lys Thr Lys Gln Ile Arg Asp
    290                 295                 300

His Ile Val Lys Val Phe Phe Phe Lys Lys
305                 310

<210> SEQ ID NO 13
<211> LENGTH: 942
<212> TYPE: DNA
<213> ORGANISM: Homo sapiens

<400> SEQUENCE: 13

```
atgacattac ccagcaacaa ctccacttcc ccagtctttg aattcttcct catttgtttc      60
cccagtttcc agagctggca gcactggctg tctctgcccc tcagcctcct cttcctcctg     120
gccatggggg ccaatgccac ccttctgatc accatctatc tggaagcctc tctgcaccag     180
cccctgtact acctgctcag cctcctctcc ctgctggaca tcgtactctg cctcaccgtc     240
atccccaagg tcctggccat cttctggttt gacctcagat caatcagctt ccctgcctgc     300
ttccttcaga tgttcatcat gaacagtttt ctgactatgg agtcctgcac attcatgatc     360
atggcctatg accgctatgt ggccatctgc aagcccctac agtactcatc catcatcact     420
gatcaatttg ttgctagggc tgccatcttt gttgtggcca ggaatggcct tcttactatg     480
cctatcccca cttttcttc tcgactcaga tactgtgcag acacatcat caagaactgc     540
atctgtacta acgtgtctgt gtctaaactc tcttgtgatg acatcacctt gaatcagagc     600
taccagtttg ttataggttg gaccctgctg ggctctgacc tcatccttat tgttctctct     660
tactttttta tcttgaaaac tgtgctaagg attaagggtg agggagatat ggccaaagct     720
ctaggtactt gtggttccca cttcatcctc atcctcttct tcaccacagt cctgctggtt     780
ctggtcatca ctaacctggc caggaagaga attcctccgg atgtccccat cctgctcaac     840
atcctgcacc accttattcc cccagctctg aacccattg tttatggtgt gagaaccaag     900
gagatcaagc agggaatcca gaacctgctg aagaggttgt aa                        942
```

<210> SEQ ID NO 14
<211> LENGTH: 313
<212> TYPE: PRT
<213> ORGANISM: Homo sapiens

<400> SEQUENCE: 14

Met Thr Leu Pro Ser Asn Asn Ser Thr Ser Pro Val Phe Glu Phe Phe

```
                1               5                   10                  15
Leu Ile Cys Phe Ser Phe Gln Ser Trp Gln His Trp Leu Ser Leu
                20                  25                  30

Pro Leu Ser Leu Leu Phe Leu Leu Ala Met Gly Ala Asn Ala Thr Leu
                35                  40                  45

Leu Ile Thr Ile Tyr Leu Glu Ala Ser Leu His Gln Pro Leu Tyr Tyr
                50                  55                  60

Leu Leu Ser Leu Leu Ser Leu Leu Asp Ile Val Leu Cys Leu Thr Val
65                  70                  75                  80

Ile Pro Lys Val Leu Ala Ile Phe Trp Phe Asp Leu Arg Ser Ile Ser
                85                  90                  95

Phe Pro Ala Cys Phe Leu Gln Met Phe Ile Met Asn Ser Phe Leu Thr
                100                 105                 110

Met Glu Ser Cys Thr Phe Met Ile Met Ala Tyr Asp Arg Tyr Val Ala
                115                 120                 125

Ile Cys Lys Pro Leu Gln Tyr Ser Ser Ile Ile Thr Asp Gln Phe Val
                130                 135                 140

Ala Arg Ala Ala Ile Phe Val Val Ala Arg Asn Gly Leu Leu Thr Met
145                 150                 155                 160

Pro Ile Pro Ile Leu Ser Ser Arg Leu Arg Tyr Cys Ala Gly His Ile
                165                 170                 175

Ile Lys Asn Cys Ile Cys Thr Asn Val Ser Val Ser Lys Leu Ser Cys
                180                 185                 190

Asp Asp Ile Thr Leu Asn Gln Ser Tyr Gln Phe Val Ile Gly Trp Thr
                195                 200                 205

Leu Leu Gly Ser Asp Leu Ile Leu Ile Val Leu Ser Tyr Phe Phe Ile
                210                 215                 220

Leu Lys Thr Val Leu Arg Ile Lys Gly Glu Gly Asp Met Ala Lys Ala
225                 230                 235                 240

Leu Gly Thr Cys Gly Ser His Phe Ile Leu Ile Leu Phe Phe Thr Thr
                245                 250                 255

Val Leu Leu Val Leu Val Ile Thr Asn Leu Ala Arg Lys Arg Ile Pro
                260                 265                 270

Pro Asp Val Pro Ile Leu Leu Asn Ile Leu His His Leu Ile Pro Pro
                275                 280                 285

Ala Leu Asn Pro Ile Val Tyr Gly Val Arg Thr Lys Glu Ile Lys Gln
                290                 295                 300

Gly Ile Gln Asn Leu Leu Lys Arg Leu
305                 310
```

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac
<220> FEATURE:
<223> OTHER INFORMATION: C-term NH2

<400> SEQUENCE: 15

Phe Lys Lys Ser Phe Lys Leu
1               5

<210> SEQ ID NO 16
<211> LENGTH: 13

-continued

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Arg Leu Ile Glu Asp Ala Glu Tyr Ala Ala Arg Gly
1               5                   10

<210> SEQ ID NO 17
<211> LENGTH: 5
<212> TYPE: PRT
<213> ORGANISM: Homo sapiens

<400> SEQUENCE: 17

Phe Ile Leu Leu Gly
1               5

<210> SEQ ID NO 18
<211> LENGTH: 6
<212> TYPE: PRT
<213> ORGANISM: Homo sapiens

<400> SEQUENCE: 18

Leu His Thr Pro Met Tyr
1               5

<210> SEQ ID NO 19
<211> LENGTH: 10
<212> TYPE: PRT
<213> ORGANISM: Homo sapiens

<400> SEQUENCE: 19

Met Ala Tyr Asp Arg Tyr Val Ala Ile Cys
1               5                   10

<210> SEQ ID NO 20
<211> LENGTH: 2
<212> TYPE: PRT
<213> ORGANISM: Homo sapiens

<400> SEQUENCE: 20

Ser Tyr
1

<210> SEQ ID NO 21
<211> LENGTH: 7
<212> TYPE: PRT
<213> ORGANISM: Homo sapiens

<400> SEQUENCE: 21

Phe Ser Thr Cys Ser Ser His
1               5

<210> SEQ ID NO 22
<211> LENGTH: 6
<212> TYPE: PRT
<213> ORGANISM: Homo sapiens

<400> SEQUENCE: 22

Pro Met Leu Asn Pro Phe
1               5
```